(12) United States Patent
Wyss-Coray et al.

(10) Patent No.: US 10,688,130 B2
(45) Date of Patent: Jun. 23, 2020

(54) METHODS AND COMPOSITIONS FOR TREATING AGING-ASSOCIATED CONDITIONS

(71) Applicants: The Board of Trustees of the Leland Stanford Junior University, Stanford, CA (US); U.S. GOVERNMENT AS REPRESENTED BY THE DEPARTMENT OF VETERANS AFFAIRS, Washington, DC (US)

(72) Inventors: Anton Wyss-Coray, Palo Alto, CA (US); Saul A. Villeda, Lancaster, CA (US); Joseph M. Castellano, San Mateo, CA (US); Jinte Middeldorp, Utrecht (NL); Martin S. Angst, Stanford, CA (US); Jian Luo, Palo Alto, CA (US)

(73) Assignees: THE BOARD OF TRUSTEES OF THE LELAND STANFORD JUNIOR UNIVERSITY, Stanford, CA (US); U.S. GOVERNMENT AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 194 days.

(21) Appl. No.: 14/562,401

(22) Filed: Dec. 5, 2014

(65) Prior Publication Data
US 2015/0157664 A1 Jun. 11, 2015

Related U.S. Application Data

(60) Provisional application No. 61/913,812, filed on Dec. 9, 2013, provisional application No. 62/069,044, filed on Oct. 27, 2014.

(51) Int. Cl.
*A61K 35/16* (2015.01)
*A61K 38/38* (2006.01)

(52) U.S. Cl.
CPC .................. *A61K 35/16* (2013.01)

(58) Field of Classification Search
None
See application file for complete search history.

(56) References Cited

U.S. PATENT DOCUMENTS

| | | | |
|---|---|---|---|
| 4,872,983 A | 10/1989 | Diamantoglou et al. |
| 5,240,614 A | 8/1993 | Ofsthun et al. |
| 5,916,202 A | 6/1999 | Haswell |
| 6,416,487 B1 | 7/2002 | Braverman et al. |
| 6,419,830 B2 | 7/2002 | Strom et al. |
| 6,423,024 B1 | 7/2002 | Strom et al. |
| 6,632,174 B1 | 10/2003 | Breznitz |
| 6,855,121 B1 | 2/2005 | Chan et al. |
| 6,946,546 B2 | 9/2005 | Vaughan et al. |
| 7,196,162 B2 | 3/2007 | Quirk et al. |
| 7,368,542 B2 | 5/2008 | McIntyre |
| 7,608,406 B2 | 10/2009 | Valkirs et al. |
| 7,739,056 B2 | 6/2010 | Landfield et al. |
| 7,785,601 B2 | 8/2010 | Schaebitz et al. |
| 7,851,172 B2 | 12/2010 | Lovell et al. |
| 7,908,090 B2 | 3/2011 | Kim et al. |
| 8,211,310 B2 | 7/2012 | Young et al. |
| 8,257,922 B2 | 9/2012 | Liew et al. |
| 8,272,518 B2 | 9/2012 | Fujita et al. |
| 8,349,550 B2 | 1/2013 | Brady et al. |
| 8,772,042 B2 | 7/2014 | Yalkinoglu et al. |
| 8,778,616 B2 | 7/2014 | Ambati et al. |
| 8,828,977 B2 | 9/2014 | Zahos et al. |
| 9,161,968 B2 | 10/2015 | Wyss-Coray et al. |
| 9,511,094 B2 | 12/2016 | Fraser et al. |
| 9,770,486 B2 | 9/2017 | Wyss-Coray et al. |
| 9,782,457 B2 | 10/2017 | Chandler et al. |
| 2002/0055158 A1 | 5/2002 | Greene et al. |
| 2002/0143283 A1 | 10/2002 | Braverman et al. |
| 2002/0151064 A1 | 10/2002 | Rothenberg et al. |
| 2003/0139332 A1 | 7/2003 | Noble et al. |
| 2003/0157687 A1 | 8/2003 | Greene et al. |
| 2004/0120937 A1* | 6/2004 | Wilson ................... A61K 35/16 424/93.71 |
| 2004/0127445 A1 | 7/2004 | Liew et al. |
| 2004/0141946 A1 | 7/2004 | Schaebitz et al. |
| 2004/0254152 A1 | 12/2004 | Monje et al. |
| 2005/0221348 A1 | 10/2005 | Ray et al. |
| 2005/0244448 A1 | 11/2005 | Chen et al. |
| 2006/0031951 A1 | 2/2006 | Klimanskaya et al. |
| 2006/0094064 A1 | 5/2006 | Ray et al. |
| 2006/0198851 A1 | 9/2006 | Basi et al. |
| 2006/0263759 A1* | 11/2006 | Alves-Filho ........... A61K 35/16 435/2 |
| 2007/0037200 A1 | 2/2007 | Ray et al. |
| 2007/0155725 A1 | 7/2007 | Li et al. |
| 2007/0190055 A1 | 8/2007 | Ambati |

(Continued)

FOREIGN PATENT DOCUMENTS

| | | |
|---|---|---|
| EP | 0184040 B1 | 4/1993 |
| EP | 2341138 A1 | 7/2011 |
| RU | 2428997 C1 | 9/2011 |
| RU | 2470677 C1 | 12/2012 |
| UA | 35656 C2 | 4/2001 |

(Continued)

OTHER PUBLICATIONS

Website document entitled "Plasma Protein Composition" (available at http://www.sigmaaldrich.com/life-science/metabolomics/enzyme-explorer/learning-center/plasma-blood-proteins/plasma-protein-composition.html). Downloaded from internet Jun. 27, 2017.*

(Continued)

*Primary Examiner* — Terry A McKelvey
*Assistant Examiner* — Russell G Fiebig
(74) *Attorney, Agent, or Firm* — Casimir Jones, S.C.

(57) ABSTRACT

Methods and compositions are provided for treating a subject for aging-associated conditions, e.g., cognitive impairment conditions. Aspects of the methods include administering a young plasma-comprising blood product to an individual in need thereof, e.g., an individual suffering from or at risk of developing the aging-associated condition, e.g., aging-associated cognitive impairment. Also provided are compositions and kits thereof that find use in practicing methods of the invention.

8 Claims, 27 Drawing Sheets
(20 of 27 Drawing Sheet(s) Filed in Color)

(56) References Cited

U.S. PATENT DOCUMENTS

| | | |
|---|---|---|
| 2008/0026485 A1 | 1/2008 | Hueber et al. |
| 2008/0057590 A1 | 3/2008 | Urdea et al. |
| 2008/0125354 A1 | 5/2008 | Fields et al. |
| 2009/0143394 A1 | 6/2009 | Wyss-Coray et al. |
| 2009/0181008 A1 | 7/2009 | Ray et al. |
| 2009/0209615 A1 | 8/2009 | Lipton et al. |
| 2009/0239241 A1 | 9/2009 | Ray et al. |
| 2010/0015235 A1 | 1/2010 | Watson et al. |
| 2010/0080850 A1 | 4/2010 | Hubbel et al. |
| 2010/0119496 A1 | 5/2010 | Wilkison et al. |
| 2010/0124756 A1 | 5/2010 | Ray et al. |
| 2010/0258496 A1 | 10/2010 | Hidaka et al. |
| 2010/0310609 A1 | 12/2010 | Watson et al. |
| 2010/0324079 A1 | 12/2010 | Ohyagi |
| 2011/0117100 A1 | 5/2011 | Britschgi et al. |
| 2011/0142848 A1 | 6/2011 | Chung et al. |
| 2011/0202284 A1 | 8/2011 | McReynolds et al. |
| 2011/0212854 A1 | 9/2011 | Ray et al. |
| 2011/0243947 A1 | 10/2011 | Doody et al. |
| 2012/0095000 A1 | 4/2012 | Wyss-Coray et al. |
| 2012/0230941 A1 | 9/2012 | Sing et al. |
| 2012/0258075 A1 | 10/2012 | Wyss-Coray et al. |
| 2013/0040844 A1* | 2/2013 | Wyss-Coray ........ C12Q 1/6883 506/9 |
| 2013/0302322 A1 | 11/2013 | Wong et al. |
| 2014/0011689 A1 | 1/2014 | Sandip et al. |
| 2014/0121438 A1 | 5/2014 | Long et al. |
| 2014/0255424 A1 | 9/2014 | Wyss-Coray et al. |
| 2014/0294724 A1 | 10/2014 | Chain et al. |
| 2015/0031562 A1 | 1/2015 | Kantor et al. |
| 2015/0079045 A1 | 3/2015 | Kong |
| 2015/0157664 A1 | 6/2015 | Wyss-Coray et al. |
| 2016/0143996 A1 | 5/2016 | Wyss-Coray et al. |
| 2016/0208011 A1 | 7/2016 | Wyss-Coray et al. |
| 2017/0081415 A1 | 3/2017 | Wong et al. |
| 2017/0232118 A1 | 8/2017 | Wyss-Coray et al. |

FOREIGN PATENT DOCUMENTS

| | | |
|---|---|---|
| WO | WO 1990011287 | 10/1990 |
| WO | WO 1997038314 | 10/1997 |
| WO | WO 1999006098 | 2/1999 |
| WO | WO 2000062836 | 10/2000 |
| WO | WO 2002006480 A2 | 1/2002 |
| WO | WO 2003006006 | 1/2003 |
| WO | WO 2003020403 | 3/2003 |
| WO | WO 2004019043 | 3/2004 |
| WO | WO 2004060425 | 7/2004 |
| WO | 2005052592 A2 | 6/2005 |
| WO | WO 2005106492 A2 | 11/2005 |
| WO | WO 2006102170 A2 | 9/2006 |
| WO | 2006133423 A1 | 12/2006 |
| WO | 2007059135 A2 | 5/2007 |
| WO | WO 2008014314 | 1/2008 |
| WO | WO 2008146018 | 12/2008 |
| WO | 2009023814 A2 | 2/2009 |
| WO | WO 2009055729 A1 | 4/2009 |
| WO | WO 2010017443 | 2/2010 |
| WO | WO 2010041617 | 4/2010 |
| WO | 2011094535 A2 | 8/2011 |
| WO | 2013142135 A1 | 9/2013 |
| WO | WO 2015081166 A1 | 6/2015 |
| WO | WO 2015088915 A1 | 6/2015 |
| WO | WO 2015161112 A1 | 10/2015 |
| WO | WO 2016187217 A2 | 11/2016 |
| WO | WO 2016205004 A2 | 12/2016 |
| WO | WO 2017120461 A1 | 7/2017 |

OTHER PUBLICATIONS

Adkins et al. (2002) Molecular & Cellular Proteomics 1: 947-955.*
Anderson et al. (1977) Proc. Natl. Acad. Sci. vol. 74, No. 12, pp. 5421-5425.*
Anderson et al. (2002) Molecular & Cellular Proteomics 1: 845-867.*
Jha, Alok. "Young blood can reverse some effects of ageing, study finds", The Guardian, Oct. 17, 2012, 4 pages.
Luo et al. "Colony-stimulating factor 1 receptor (CSF1R) signaling in injured neurons facilitates protection and survival.", J. Exp. Med. (2013) 210(1):157-172.
Middeldorp et al. "A young systemic environment reverses degeneration in a mouse model of Alzheimer's disease", Neuroscience 2012, Presentation Abstract, Oct. 16, 2012, 2 pages.
Ron-Harel et al. "Age-Dependent Spatial Memory Loss Can Be Partially Restored by Immune Activation", Rejuvenation Resarch (2008), 11(5):903-13.
Schwartz et al. "How Do Immune Cells Support and Shape the Brain in Health, Disease, and Aging?" The Journal of Neuroscience, Nov. 6, 2013, 33(45):17587-96.
"Young blood can reverse some effects of ageing, study finds", Author Unknown, Society for Neuroscience, The Observer, Oct. 24, 2012, 2 pages, Retrieved online: http://gonzoj.wordpress.com/tag/society-for-neuroscience/.
Thomson et al. "Young blood for a keener mind", NewScientist (2012), 216(2887): 10.
Villeda et al. "The aging systemic milieu negatively regulates neurogenesis and cognitive function", Nature, Aug. 31, 2011, 477(7362):90-4.
Villeda et al. "Young blood reverses age-related cognitive impairments", Neuroscience 2012, Presentation Abstract, Oct. 17, 2012, 2 pages.
Villeda et al. "Young blood reverses age-related impairments in cognitive function and synaptic plasticity in mice", Nat Med. (Jun. 2014), 20(6):659-63.
Bouchard et al. "Aging and brain rejuvenation as systemic events", J. Neurochem. Jan. 2015; 132(1):5-19.
Malkki, H. "Ageing: Could young blood combat age-related cognitive decline?" Nat. Rev. Neurol. Jun. 2014;10(6):307.
Conboy et al. Heterochromic parabosis for the study of the effects of aging on stem cells and their niches. Cell cycle. 2012. pp. 2260-2268.
Nikolai Krementsov, A Martian Stranded on Earth: Alexander Bogdanov, Blood Transfusions, and Proletarian Science. pp. 57-59, 85, 86, and 88. University of Chicago Press, Chicago, United States, 2011.
Bhattacharya. Study of the utility of placental cord blood in meeting the transfusion needs of beta-thalassaemic patients. Regional Health Forum, 2008. pp. 16-27.
Villeda et al. The aging systemic milieu negatively regulates neurogenesis and cognitive function. Nature. Available online Mar. 2011. Submitted pp. 1-17.
Katcher. Studies the Shed New Light on Aging. Biochemistry (Moscow), Sep. 2013. pp. 1061-1070.
Conboy et al. Rejuvenation of aged progenitor cells by exposure to a young systemic environment. Nature. 2005. pp. 760-764.
Loffredo et al. Growth Differentiation Factor 11 Is a Circulating Factor that Reverses Age-Related Cardiac Hypertrophy. Cell. May 2013. pp. 828-839.
Borlongan et al., Central Nervous System Entry of Peripherally Injected Umbilical Cord Blood Cells Is Not Required for Neuroprotection in Stroke. Stroke. 2004. pp. 2385-2389. Dallas, Texas.
Bhattacharya. Placental umbilical cord whole blood transfusion A safe and genuine blood substitute for patients of the under-resourced ares of this country at emergency. J Am Coll Surg. 2005. Submitted 34 pages.
Conboy et al. Heterochromic parabiosis: historical perspective and methodological considerations for studies of aging andlongevity, Aging Cell, available online Apr. 2013. pp. 525-530.
Adair et al., "Measurement of gelatinase B (MMP-9) in the cerebrospinal fluid of patients with vascular dementia and Alzheimer disease." Stroke. Jun. 2004;35(6):e159-62.
Baba et al., "Timp-3 deficiency impairs cognitive function in mice." Lab Invest. Dec. 2009;89(12):1340-7.
Berezovskaya et al., "Colony stimulating factor-1 potentiates neuronal survival in cerebral cortex ischemic lesion." Acta Neuropathol. Nov. 1996;92(5):479-86.

(56) References Cited

OTHER PUBLICATIONS

Boissonneault et al., "Powerful beneficial effects of macrophage colony-stimulating factor on beta-amyloid deposition and cognitive impairment in Alzheimer's disease." Brain. Apr. 2009;132(Pt 4):1078-92.
Britschgi et al., "Blood protein signature for the early diagnosis of Alzheimer disease." Arch Neurol. Feb. 2009;66(2):161-5.
Cheung et al., "Serum β-2 microglobulin predicts mortality in people with diabetes." Eur J Endocrinol. May 17, 2013;169(1):1-7.
Fedoroff e al., "Role of colony stimulating factor-1 in brain damage caused by ischemic." Neurosci Biobehav Rev. Mar. 1997;21(2):187-91.
Gowing et al., "Macrophage colony stimulating factor (M-CSF) exacerbates ALS disease in a mouse model through altered responses of microglia expressing mutant superoxide dismutase." Exp Neurol. Dec. 2009;220(2):267-75.
Kwak et al., "Aging, exercise, and extracellular matrix in the heart." J Exerc Rehabil. Jun. 30, 2013;9(3):338-47.
Lin et al., "Discovery of a cytokine and its receptor by functional screening of the extracellular proteome." Science. May 9, 2008;320(5877):807-11.
Lysaght et al., "Beta-2 microglobulin removal during continuous ambulatory peritoneal dialysis (CAPD)." Perit Dial Int. 1989;9(1):29-35.
Manzo et al., "Role of chemokines and chemokine receptors in regulating specific leukocyte trafficking in the immune/inflammatory response." Clin Exp Rheumatol. Jul.-Aug. 2003;21(4):501-8.
McLaurin et al., "Microglial pilgrimage to the brain." Nat Med. Dec. 2010;16(12):1380-1.
Mitrasinovic et al., "Microglia overexpressing the macrophage colony-stimulating factor receptor are neuroprotective in a microglial-hippocampal organotypic coculture system." J Neurosci. Apr. 25, 2007;25(17):4442-51.
Mizuno e al., "Interleukin-34 selectively enhances the neuroprotective effects of microglia to attenuate oligomeric amyloid-β neurotoxicity." Am J Pathol. Oct. 2011;179(4):2016-27.
Palop et al., "A network dysfunction perspective on neurodegenerative diseases." Nature. Oct. 19, 2006;443(7113):768-73.
Prakasam et al., "Amyloid and Neurodegeneration: Alzheimer's Disease and Retinal Degeneration" Chapter 7, Handbook of Neurochemistry and Molecular Neurobiology, Lajtha ed., 2009, 131-163. (Year: 2009).
Royer et al., "A novel antagonist of prostaglandin 02 blocks the locomotion of eosinophils and basophils." Eur J Clin nvesl. Sep. 2008;38(9):663-71.
Sellebjerg, et al., "Identification of new sensitive biomarkers for the in vivo response to interferon-beta treatment in multiple sclerosis using DNA-array evaluation." Eur J Neurol. Dec. 2009;16(12):1291-8.
Shin et al., "Association of Eotaxin gene family with asthma and serum total IgE." Hum Mol Genet. Jun. 1, 2003;12(11):1279-85.
Skovronsky et al., "Neurodegenerative diseases: new concepts of pathogenesis and their therapeutic implications." Annu Rev Pathol. 2006;1:151-70.
Smith et al., "β2-microglobulin is a systemic pro-aging factor that impairs cognitive function and neurogenesis." Nat Med. Aug. 2015;21(8):932-37.
Strobel et al., "Chicago: The Vampire Principle—Young Blood Rejuvenates Aging Brain?", Alzheimer Research Forum (Nov. 2009), pp. 1-3.
Stubbs et al., "Indomethacin causes prostaglandin 0(2)-like and eotaxin-like selective responses in eosinophils and basophils." J Bioi Chern. Jul. 19, 2002;277(29):26012-20.
Teixeira, A.L. et al, "Increased serum levels of CCL 11/eotaxin in schizophrenia", Process in Neuro-Psychopharmacology & Biological Psychiatry, vol. 32, No. 3, pp. 710-714, 2008.
Villeda et al., "Changes in the systemic milieu modulate neurogenesis during aging" Abstract, 39th Annual Neuroscience Meeting, Chicago, IL, Society for Neuroscience, Oct. 2009, 1-2. (Year: 2009).

Villeda et al., "Changes in the systemic milieu modulate neurogenesis during aging", Neuroscience (2009), Abstract Only.
Villeda et al., Meeting Date, Past and Future Meetings, 39th Annual Neuroscience Meeting, Society for Neuroscience, 2009, 1. (Year: 2009).
Vincent et al., "Macrophage colony stimulating factor prevents NMDA-induced neuronal death in hippocampal organotypic cultures." J Neurochem. Sep. 2002;82(6):1388-1397.
Wang et al., "Expression of colony stimulating factor-1 receptor (CSF-1R) by CNS neurons in mice." J Neurosci Res. Sep. 1, 1999;57(5):616-32.
Wang et al., "Matrix metalloproteinases and their multiple roles in Alzheimer's disease." Biomed Res Int. 2014;2014:908636.
Wilson et al., "Beta2-microglobulin as a biomarker in peripheral arterial disease: proteomic profiling and clinical studies." Circulation. Sep. 18, 2007;116(12):1396-403.
Yagihashi A. et al., "Macrophage colony stimulating factor (M-CSF) protects spiral ganglion neurons following auditory nerve injury: morphological and functional evidence." Exp Neurol. Mar. 2005;192(1):167-77.
Yamane et al., "CSF-1 receptor-mediated differentiation of a new type of monocytic cell with B cell-stimulating activity: its selective dependence on IL-34." J Leukoc Biol. Jan. 2014;95(1):19-31.
Ye, et al., "Haptoglobin-alpha subunit as potential serum biomarker in ovarian cancer: identification and characterization using proteomic profiling and mass spectrometry." Clinical Cancer Research (Aug. 2003), 9 (8):2904-11.
Search Report of related PCT/US2011/022916, dated Oct. 31, 2011, 11 pages.
Search Report of related PCT/US2014/068897, dated Feb. 27, 2015, 11 pages.
Search Report of related PCT/US2016/032907, dated Dec. 1, 2016, 24 pages.
Search Report of related PCT/US2016/036032, dated Feb. 21, 2017, 13 pages.
Search Report of related PCT/US2017/012521, dated Feb. 2, 2017, 12 pages.
Search Report dated Aug. 2, 2017, for related European application No. 14868769.2., 8 pages.
Adachi et al., "Intravascular lymphomatosis: a case report" No Shinkei Geka. Jul. 2001;29(7):659-65. Original in Japanese (English abstract obtained from pubmed).
Ameer et al., "A novel immunoadsorption device for removing beta2-microglobulin from whole blood." Kidney Int. Apr. 2001;59(4):1544-50.
Brew et al., "The tissue inhibitors of metalloproteinases: An ancient family with structural and functional diversity," Biochimica et Biophysica Acta (2010) 1803: 55-71).
Giorgetti et al., "beta2-Microglobulin is potentially neurotoxic, but the blood brain barrier is likely to protect the brain from its toxicity." Nephrol Dial Transplant. Apr. 2009;24(4):1176-81.
Gomez, et al., "Tissue inhibitors of metalloproteinases: structure, regulation and biological functions," European Journal of Cell Biology (1997) 74: 111-22).
Kassiri, et al., "Tissue inhibitor of metalloproteinases (TIMPs) in heart failure," Heart Failure Reviews (2012) 17: 693-706).
Komosinkska-Vassev, et al., "Age-and gender-dependent changes in connective tissue remodeling: physiological differences in circulating MMP-3, MMP-10, TIMP-1, and TIMP-2 levels," Gerontology (2011) 57: 44-52).
Lee, et al., "Effects of aging on blood brain barrier and matrix metalloproteases following controlled cortical impact in mice," Experimental Neurology (2012) 234: 50-61).
Longo "Alzheimer's Prevention, Treatment and Research-A Q&A" Stanford Health Now, 2016, 1-2.
Perez-Martinez et al. "Tissue inhibitor of metalloproteinase-2 promotes neuronal differentiation by acting as an anti-mitogenic signal." J Neurosci. May 18, 2005;25(20):4917-29.
Martino et al., "Circulating MicroRNAs Are Not Eliminated by Hemodialysis" (2012) Circulating MicroRNAs Are Not Eliminated by Hemodialysis. PLOS ONE 7(6): e38269.

(56) References Cited

OTHER PUBLICATIONS

Moore et al., "An Alternate Perspective on the Roles of TIMPs and MMPs in Pathology," The American Journal of Pathology (2012) 180: 12-16).
Murphy, "Tissue inhibitors of metalloproteinases," Genome Biology (2011) 12).
Niezgoda et al., "The effect of cladribine treatment on beta-2 microglobin in the cerebrospinal fluid and serum of patients with multiple sclerosis" Neurol Neurochir Pol. Mar.-Apr. 2000;34(2):281-7. (Abstract).
Reitz, "Toward precision medicine in Alzheimer's disease." Ann Transl Med. Mar. 2016;4(6):107.
Stetler-Sstevenson et al., "TIMP-2: an endogenous inhibitor of angiogenesis," Trends in Molecular Medicine (2005) 11: 97-103).
Stetler-Stevenson, "Tissue Inhibitors of Metalloproteinases in Cell Signaling," Science Signaling (2008) 1).
Suzuki et al., "Beta2-microglobulin-selective adsorbent column (Lixelle) for the treatment of dialysis-related amyloidosis." Ther Apher Dial. Feb. 2003;7(1):104-7.
Visse et al. "Matrix Metalloproteinases and Tissue Inhibitors of Metalloproteinases," Circulation Research (2003) 92: 827-39).
Xu, et al., "Matrix Metalloproteinase Inhibitors: A review on Bioanalytical Methods, Pharmacokinetics and Metabolism," Current Drug Metabolism (2011) 12: 395-410).
Examiner Report of 2016265648, dated May 11, 2018, 6 pages.
Examiner Report of 738184, dated Apr. 6, 2018, 4 pages.
Examiner Report of 720949, dated Jan. 18, 2019, 5 pages.
Allodi "modeling motor neuron resilience in ALS using stem cells" accessed from biorxiv (Year: 2018), 28 pages.
Archibald et al., "The retina in Parkinson's disease." Brain. May 2009;132(Pt 5):1128-45.
Cairo CW et al., Drug-Receptor Interactions, Principles of Pharmacology, (2nd ed.), Chapter 1, pp. 3-18 (2008)).
GHR "Parkinson's disease" accessed from ghr.nlm.nih.gov on Mar. 15, 2009 (Year: 2019), 10 pages.
Mayer et al., "Identification of receptor binding and activation determinants in the N-terminal and N-loop regions of the CC chemokine eotaxin."J Biol Chem. Apr. 27, 2001;276(17):13911-6.
Politis et al., "Parkinson's disease symptoms: the patient's perspective." Mov Disord. Aug. 15, 2010;25(11):1646-51.
Wikipedia A "Huntingtin" accessed on Mar. 15, 2019 (excerpt) (Year: 2019).
Wikipedia B "Huntington's disease (Genetics)" accessed Mar. 15, 2019 (excerpt) (Year: 2019).
Zheng et al., "Agonist-selective signaling of G protein-coupled receptor: mechanisms and implications." IUBMB Life. Feb. 2010;62(2):112-9.

\* cited by examiner

METHODS AND COMPOSITIONS FOR TREATING AGING-ASSOCIATED CONDITIONS

CROSS-REFERENCE TO RELATED APPLICATIONS

Pursuant to 35 U.S.C. § 119 (e), this application claims priority to the filing date of the U.S. Provisional Patent Application Ser. No. 62/069,044, filed Oct. 27, 2014, and U.S. Provisional Patent Application Ser. No. 61/913,812, filed Dec. 9, 2013; the disclosure of which is herein incorporated by reference.

STATEMENT REGARDING FEDERALLY-SPONSORED RESEARCH

This invention was made with Government support under contract AG045034 awarded by the National Institutes of Health. The Government has certain rights in the invention.

INTRODUCTION

Aging in an organism is accompanied by an accumulation of changes over time. In the nervous system, aging is accompanied by structural and neurophysiological changes that drive cognitive decline and susceptibility to degenerative disorders in healthy individuals. (Heeden, T. & Gabrieli, J. D., Insights into the ageing mind: a view from cognitive neuroscience. Nat. Rev. Neurosci. 5(2), 87-96 (2004); Raz, N. et al. Neuroanatomical correlates of cognitive aging: evidence from structural magnetic resonance imaging. Neuropsychology 12(1), 95-114 (1998); Mattson, M. P. & Magnus, T., Ageing and neuronal vulnerability. Nat. Rev. Neurosci. 7(4), 278-294 (2006); Rapp, P. R. & Heindel, W. C., Memory systems in normal and pathological aging. Curr. Opin. Neurol. 7(4), 294-298 (1994)). Included in these changes are synapse loss and the loss of neuronal function that results. Thus, although significant neuronal death is typically not observed during the natural aging process, neurons in the aging brain are vulnerable to sub-lethal age-related alterations in structure, synaptic integrity, and molecular processing at the synapse, all of which impair cognitive function.

In addition to the normal synapse loss during natural aging, synapse loss is an early pathological event common to many neurodegenerative conditions, and is the best correlate to the neuronal and cognitive impairment associated with these conditions. Indeed, aging remains the single most dominant risk factor for dementia-related neurodegenerative diseases such as Alzheimer's disease (AD) (Bishop, N. A., Lu, T., & Yankner, B. A., Neural mechanisms of ageing and cognitive decline. Nature 464(7288), 529-535 (2010); Heeden, T. & Gabrieli, J. D., Insights into the ageing mind: a view from cognitive neuroscience. Nat. Rev. Neurosci. 5(2), 87-96 (2004); Mattson, M. P. & Magnus, T., Ageing and neuronal vulnerability. Nat. Rev. Neurosci. 7(4), 278-294 (2006)).

As human lifespan increases, a greater fraction of the population suffers from aging-associated cognitive impairments, making it crucial to elucidate means by which to maintain cognitive integrity by protecting against, or even counteracting, the effects of aging (Hebert, L. E. et al. Alzheimer disease in the US population: prevalence estimates using the 2000 census. Arch. Neurol. 60(8), 1119-1122 (2003); Bishop, N. A., et al., Neural mechanisms of ageing and cognitive decline. Nature 464(7288), 529-535 (2010)).

SUMMARY

Methods and compositions are provided for treating a subject for aging-associated conditions, e.g., cognitive impairment conditions or age-related dementia. Aspects of the methods include administering a young plasma-comprising blood product to an individual in need thereof, e.g., an individual suffering from or at risk of developing the aging-associated condition, e.g., aging-associated cognitive impairment or age-related dementia. Also provided are compositions and kits thereof that find use in practicing methods of the invention.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION

Figure 1:
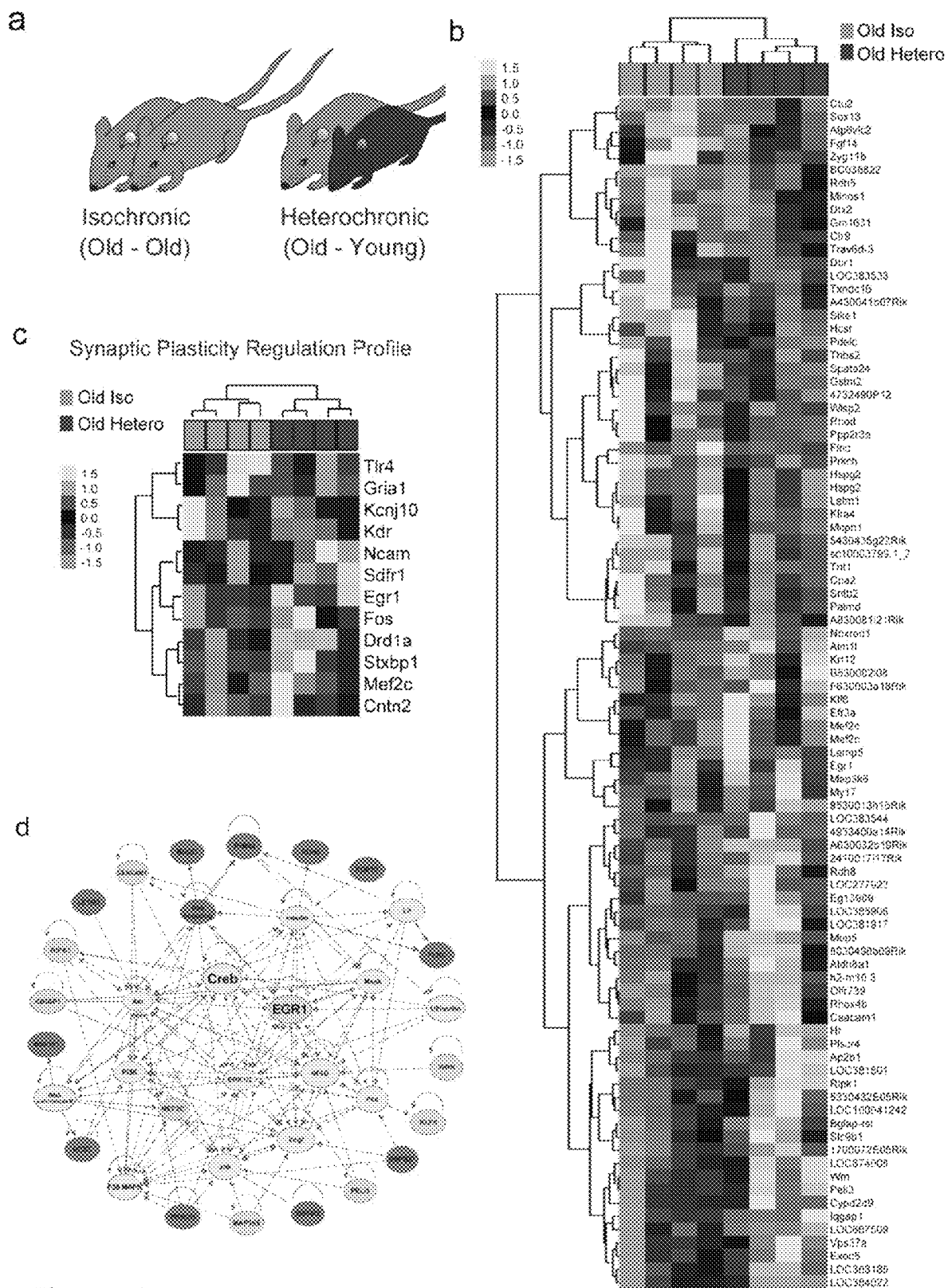
FIG. 1, Panels a-d. Genome-wide microarray analysis of heterochronic parabionts identifies a plasticity related expression profile in the old hippocampus. Microarray analysis was performed on hippocampi of old (18-month-old) isochronic and heterochronic parabionts 5 weeks post-surgery. N=4 mice per group. For all analyses down-regulated genes are shown in shades of blue and up-regulated genes are shown in shades of yellow. Panel a, Schematic depicting parabiotic pairings. Isochronic pairs shown in gray and heterochronic pairs shown in red. Panel b. Heat map was generated by unsupervised hierarchical clustering with data set of genes differentially expressed between hippocampi of old isochronic and heterochronic parabionts using a cut-off at $p<0.01$ and d-score>2 based on Significance Analysis of Microarray (SAM). Panel c, Hierarchical clustering of synaptic plasticity related genes identified by AmiGO (Gene Ontology) using a cut-off at $p<0.01$ and d-score>1.5 based on SAM. Color bars in Panel b and Panel c reflect Z-scores. Panel d. Biological pathways involved in synaptic plasticity were identified as part of the top signaling network ($p<0.05$) using Ingenuity Pathway Analysis (IPA) software based on differentially expressed genes in isochronic and heterochronic parabionts. Inferred molecular interactions identified by IPA are shown in gray.

Methods and compositions are provided for treating a subject for aging-associated conditions, e.g., cognitive impairment conditions, age-related dementia or age related decline of physiological function of peripheral organ(s). Aspects of the methods include administering a young plasma-comprising blood product to an individual in need thereof, e.g., an individual suffering from or at risk of developing the aging-associated condition, e.g., aging-associated cognitive impairment or pathological types of dementia. Also provided are compositions and kits thereof that find use in practicing methods of the invention.

Before the present methods and compositions are described, it is to be understood that this invention is not limited to a particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g., polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Methods

As summarized above, aspects of the invention include methods for treating a subject for aging-associated conditions. By aging-associated condition is meant a condition, e.g., a disease condition or other undesirable condition, which accompanies aging of an organism. The aging associated condition may manifest in a number of different ways, e.g., as aging associated damage to central or peripheral organs of the body, such as but not limited to: cell injury, tissue damage, organ dysfunction, aging-associated lifespan shortening and carcinogenesis, where specific organs and tissues of interest include, but are not limited to skin, neuron, muscle, pancreas, brain, kidney, lung, stomach, intestine, spleen, heart, adipose tissue, testes, ovary, uterus, liver and bone. In some instances, treatment of a subject in accordance with the methods results in a change in a central organ, e.g., a central nervous system organ, such as the brain, spinal cord, etc., where the change may manifest in a number of different ways, e.g., as described in greater detail below, including but not limited to molecular, structural and/or functional. In some instances, treatment of a subject in accordance with the methods results in a change in a peripheral organ, such as liver, muscle, heart, blood, etc., where the change may manifest in a number of different ways, e.g., as described in greater detail below.

In some embodiments, the aging-associated condition that is treated is an aging-associated impairment in cognitive ability in an individual. By cognitive ability, or "cognition", it is meant the mental processes that include attention and concentration, learning complex tasks and concepts, memory (acquiring, retaining, and retrieving new information in the short and/or long term), information processing (dealing with information gathered by the five senses), visuospatial function (visual perception, depth perception, using mental imagery, copying drawings, constructing objects or shapes), producing and understanding language, verbal fluency (word-finding), solving problems, making decisions, and executive functions (planning and prioritizing). By "cognitive decline", it is meant a progressive decrease in one or more of these abilities, e.g., a decline in memory, language, thinking, judgment, etc. By "an impairment in cognitive ability" and "cognitive impairment", it is meant a reduction in cognitive ability relative to a healthy individual, e.g., an age-matched healthy individual, or relative to the ability of the individual at an earlier point in time, e.g., 2 weeks, 1 month, 2 months, 3 months, 6 months, 1 year, 2 years, 5 years, or 10 years or more previously. By "aging-associated cognitive impairment," it is meant an impairment in cognitive ability that is typically associated with aging, including, for example, cognitive impairment associated with the natural aging process, e.g., mild cognitive impairment (M.C.I.); and cognitive impairment associated with an aging-associated disorder, that is, a disorder that is seen with increasing frequency with increasing senescence, e.g., a neurodegenerative condition such as Alzheimer's disease, Parkinson's disease, frontotemporal dementia, Huntington disease, amyotrophic lateral sclerosis, multiple sclerosis, glaucoma, myotonic dystrophy, vascular dementia, and the like.

By "treatment", "treating" and the like it is generally meant obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. Treatment may results in a variety of different physical manifestations, e.g., modulation in gene expression, rejuvenation of tissue or organs, etc. The therapeutic agent may be administered before, during or after the onset of disease or injury. The treatment of ongoing disease, where the treatment stabilizes or reduces the undesirable clinical symptoms of the patient, is of particular interest. Such treatment may be performed prior to complete loss of function in the affected tissues. The subject therapy may be administered during the symptomatic stage of the disease, and in some cases after the symptomatic stage of the disease.

In some instances where the aging-associated condition is aging-associated cognitive decline, treatment by methods of the present disclosure slows, or reduces, the progression of aging-associated cognitive decline. In other words, cognitive abilities in the individual decline more slowly following treatment by the disclosed methods than prior to or in the absence of treatment by the disclosed methods. In some instances, treatment by methods of the present disclosure stabilizes the cognitive abilities of an individual. For example, the progression of cognitive decline in an individual suffering from aging-associated cognitive decline is halted following treatment by the disclosed methods. As another example, cognitive decline in an individual e.g., an individual 40 years old or older, that is projected to suffer from aging-associated cognitive decline, is prevented following treatment by the disclosed methods. In other words, no (further) cognitive impairment is observed. In some instances, treatment by methods of the present disclosure reduces, or reverses, cognitive impairment, e.g., as observed by improving cognitive abilities in an individual suffering from aging-associated cognitive decline. In other words, the cognitive abilities of the individual suffering from aging-associated cognitive decline following treatment by the disclosed methods are better than prior to treatment by the disclosed methods, i.e., they improve upon treatment. In some instances, treatment by methods of the present disclosure abrogates cognitive impairment. In other words, the cognitive abilities of the individual suffering from aging-associated cognitive decline are restored, e.g., to their level when the individual was about 40 years old or less, following treatment by the disclosed methods, e.g., as evidenced by improved cognitive abilities in an individual suffering from aging-associated cognitive decline.

In practicing the subject methods, a young plasma-comprising blood product is administered to an individual in need thereof, e.g., an individual suffering or at risk of suffering from an aging associated condition, e.g., aging-associated cognitive impairment or age-related dementia. As such, methods according to embodiments of the invention including administering a plasma-comprising product from a young individual (the "donor individual", or "donor") to an individual at least at risk of suffering from an aging-associated cognitive impairment, i.e., an individual suffering or at risk of suffering from an aging-associated cognitive impairment (the "recipient individual" or "recipient"). By a "plasma-comprising blood product," it is meant any product derived from blood that comprises plasma. The term "plasma' is used in its conventional sense to refer to the straw-colored/pale-yellow liquid component of blood composed of about 92% water, 7% proteins such as albumin, gamma globulin, anti-hemophilic factor, and other clotting factors, and 1% mineral salts, sugars, fats, hormones and vitamins. Non-limiting examples of plasma-comprising blood products suitable for use in the subject methods include whole blood treated with anti-coagulant (e.g., EDTA, citrate, oxalate, heparin, etc.), blood products produced by filtering whole blood to remove white blood cells ("leukoreduction"), and blood product consisting essentially of purified plasma. In some instances, young plasma product that is employed is a non-whole blood plasma product, by which is meant that the product is not whole blood, such that it lacks one or more components found in whole blood, such as erythrocytes, leukocytes, etc., at least to the extent that these components are present in whole blood. In some instances, the young plasma product is substantially, if not completely, acellular, where in such instances the cellular content may be 5% or less, such as 1% or less, including 0.5% or less.

The terms "individual," "subject," "host," and "patient," are used interchangeably herein and refer to any mammalian subject for whom diagnosis, treatment, or therapy is desired, particularly humans. Typically, the donor and recipient will be of the same species. Mammalian species that may be treated with the present methods include canines and felines; equines; bovines; ovines; etc. and primates, particularly humans. The subject methods, compositions, and reagents may also be applied to animal models, particularly small mammals, e.g., murine, lagomorpha, etc., for example, in experimental investigations. The discussion below will focus on the application of the subject methods, compositions, reagents, devices and kits to humans, but it will be understood by the ordinarily skilled artisan that such descriptions can be readily modified to other mammals of interest based on the knowledge in the art.

By a "young individual" it is meant an individual that is 40 years old or younger, e.g., 35 years old or younger, including 30 years old or younger, e.g., 25 years old or younger. In some instances, the individual that serves as the source of the young plasma-comprising blood product is one that is 10 years old or younger, e.g., 5 years old or younger, including 1 year old or younger. In some instances, the subject is a newborn and the source of the plasma product is the umbilical cord, where the plasma product is harvested from the umbilical cord of the new born. As such, "young individual" may refer to a subject that is between the ages of 0 and 40, e.g., 0, 1, 5, 10, 15, 20, 25, 30, 35, or 40 years old. Usually, the individual is healthy, e.g., the individual has no hematological malignancy or autoimmune disease at the time of harvest.

By "an individual suffering from or at risk of suffering from an aging-associated cognitive impairment" it is meant to include an individual that is about 50 years old or older, e.g., 60 years old or older, 70 years old or older, 80 years old or older, and usually no older than 100 years old, such as 90 years old, i.e., between the ages of about 50 and 100, e.g., 50, 55, 60, 65, 70, 75, 80, 85 or about 90 years old, and suffers from an aging associated condition, e.g., cognitive impairment, associated with the natural aging process, e.g., M.C.I.; an individual that is about 50 years old or older, e.g., 60 years old or older, 70 years old or older, 80 years old or older, 90 years old or older, and usually no older than 100 years old, i.e., between the ages of about 50 and 100, e.g., 50, 55, 60, 65, 70, 75, 80, 85, 90, 95 or about 100 years old, that has not yet begun to show symptoms of an aging associated condition, e.g., cognitive impairment; an individual of any age that is suffering from a cognitive impairment due to an aging-associated disease, e.g., Alzheimer's disease, Parkinson's disease, frontotemporal dementia, Huntington disease, amyotrophic lateral sclerosis, multiple sclerosis, glaucoma, myotonic dystrophy, dementia, and the like, and an individual of any age that has been diagnosed with an aging-associated disease that is typically accompanied by cognitive impairment, e.g., Alzheimer's disease, Parkinson's disease, frontotemporal dementia, progressive supranuclear palsy, Huntington disease, amyotrophic lateral sclerosis, spinal muscular atrophy, multiple sclerosis, multisystem atrophy, glaucoma, ataxias, myotonic dystrophy, dementia, and the like, where the individual has not yet begun to show symptoms of cognitive impairment.

In some instances, the donor of the blood product (i.e., the young individual) is different from the recipient (i.e., the individual suffering from or at risk of suffering from an aging associated-cognitive impairment). In other words, the blood product is allogeneic to the recipient. In some such instances, the blood product to be administered is selected based upon the blood type of the donor and the blood type of the recipient. By blood type, it is meant the presence or absence of A and B antigens and Rh antigen on the donor and recipient's red blood cells. For example, as is well understood in the art, an individual may have neither A or B antigens on his red blood cells (and hence will have antibodies specific for both A and B antigens in his plasma), in which case the individual is "type O". The individual may have A antigen and not B antigen on his red blood cells (and hence will have antibodies specific for B antigen but not A antigen in his plasma), in which case the individual is "type A." The individual may have B antigen and not A antigen on his red blood cells (and hence antibodies specific for A antigen but not B antigen in his plasma), in which case the individual is "type B." The individual may have both A and B antigens on his red blood cells (and hence no antibodies for either A or B antigen in his plasma), in which case the individual is "type AB." As well known in the art, safe transfusion of donor blood to a recipient can occur if the donor is type O and the recipient is any type; if the donor is type A and the recipient is type A or type AB; if the donor is type B and the recipient is type B or type AB; or if the donor is type AB and the recipient is type AB. Additionally, as is known in the art, the Rh antigen may or may not be present, i.e., the individual is Rh-positive or Rh-negative, respectively. As is well known in the art, safe transfusion of donor blood to a recipient can occur if the donor is type $Rh^+$ or $Rh^+$ and the recipient is type $Rh^+$; or if the donor is type $Rh^-$ and the recipient is type $Rh^-$. In other such instances, e.g., when the blood product is a fractionated product that comprises no cells displaying the NB or Rh antigens, for example, a blood product that consists essentially of plasma, the blood product from a donor of any blood type may be administered to the recipient.

In other instances, the donor and the recipient are the same individual, i.e., the blood is drawn from an individual, and the blood product that is prepared from that blood draw is transferred back (restored) into the same individual, e.g., 10 years or more later, e.g., 10, 20, 30, 40, 50, 60, 70, 80, or 90 years later. In other words, the blood product is autologous to the recipient. For example, the blood may have been harvested from the individual when the individual was about 40 years old or younger, e.g., between the ages of 10 and 40, e.g., 10, 15, 20, 25, 30, 35, or 40 years old; and is transfused back into the individual when the individual is about 50 years old or older, e.g., between the ages of 50 and 90, e.g., 50, 55, 60, 65, 70, 75, 80, 85, 90, 95 or about 100 years old. Thus, in particular embodiments of the invention, blood is harvested from an individual, preserved, and transferred back into that individual at an older age.

As indicated above, the blood product suitable for use in the subject methods is a plasma-comprising blood product prepared from blood drawn from a young individual. The blood may be drawn manually, with automated equipment, or with some combination thereof. Any convenient volume may be drawn that does not endanger the life of the donor. In some instances, a volume of 200-600 milliliters of plasma-comprising blood product is drawn, for example 300-550 ml, or 450-500 ml. The drawn blood may be treated with an agent that prevents coagulation, i.e., an anti-coagulant, e.g., EDTA, citrate, oxalate, heparin, etc. For example, anti-coagulant may be added to the blood as it is drawn. As another example, the receptacle into which the blood is collected may comprise anti-coagulant. Other agents, e.g., buffers, preservatives, e.g., phosphate, dextrose, adenine, glycerine, glucose, raffinose, etc., agents that kill viruses, e.g., solvent detergent, etc., may also be added to the blood.

In some instances, the blood may be fractionated, e.g., to remove leukocytes, erythrocytes, platelets, antibodies, etc., and the plasma-comprising fraction, i.e., the "plasma-comprising blood product," retained for use. For example, the whole blood may be fractionated by filtration, centrifugation, etc., after collection is complete. As another example, the whole blood may be fractionated as it is drawn from the donor, and non-plasma components returned to the blood stream of the donor. For example, fractionated blood comprising plasma may be harvested by apheresis. By "apheresis" it is meant an automated blood collection in which harvested blood is passed through a machine that separates out certain components, e.g., leukocytes, red blood cells, plasma, etc., and returns the remaining blood components to the blood stream of the donor. In some instances, the apheresis is plasmapheresis, i.e., apheresis in which plasma is separated out and the remaining blood components returned to the donor's blood stream. In some such instances, the plasma-comprising blood product consists essentially of plasma.

In some embodiments, the plasma-comprising blood product, i.e., whole blood or plasma-comprising fraction thereof, is further processed to remove one or more polypeptide fractions, such as a polypeptide fraction having an average molecular below a predetermined threshold. While the predetermined threshold may vary, thresholds of interest include, but are not limited to: 3.5 kDa, 10 kDa, 25 kDa, 50 kDa. In some instances, a specific proteinaceous component may also be removed, e.g., IgG, etc. By the "average molecular weight" it is meant the mass of a polypeptide as calculated by multiplying the total number of amino acids in the polypeptide by the average molecular weight of 110 kD for each. A number of methods are known in the art for the removal of polypeptides that are a given molecular weight or less from liquid samples. For example, the blood product may be subject to size-exclusion chromatography (SEC), e.g., gel filtration chromatography, in which the plasma-comprising blood product is passed over a matrix of beads comprising pores that retard proteins of a given molecular weight or less, thereby depleting the flow-through of these small polypeptides. As another example, the blood product may be subjected to hydrodynamic chromatography (HDC), in which the parabolic or Poiseuille-like flow of a sample that develops under laminar flow through a tube or packed column causes larger particles to travel in the faster-moving flow at the center of the tube and smaller particles to be retarded along the slower-moving flow closer to the walls of the tube. Any convenient method, e.g., SEC, HDC, and the like, may be employed to remove proteins that have a given threshold average molecular weight or less from the blood product. Specific fractions of interest that may be employed in given embodiments of the invention include, but are not limited to: fractions in which polypeptides having an average molecular weight of 3.5 kDa or less have been removed; fractions in which polypeptides having an average molecular weight of 10 kDa or less have been removed; fractions in which polypeptides having an average molecular weight of 25 kDa or less have been removed; fractions in which polypeptides having an average molecular weight of 50 kDa or less have been removed; and fractions in which polypeptides having an average molecular weight of any of the above thresholds (e.g., 3.5 kDa, 10 kDa, 25 kDa, 50 kDa) or less and IgG has been removed. In other words, the blood product may be viewed a given molecular weight (e.g., 3.5 kD-; 10 kD-; 25 kD-; 50 kD-) depleted plasma-comprising blood product. In some instances, the fraction that is administered is not a denatured fraction.

Plasma-comprising blood product, e.g., whole blood or a plasma-comprising fraction thereof, so prepared may then be administered to the individual suffering from or at risk of developing an aging-associated condition, e.g., cognitive impairment. In some embodiments, the plasma-comprising blood product is administered immediately, e.g., within about 12-48 hours of collection, to the individual suffering from or at risk of developing an aging-associated cognitive impairment. In such instances, the blood product may be stored under refrigeration, e.g., 0-10° C. In other embodiments, the plasma-comprising blood product is preserved, e.g., by cryopreservation, etc., as known in the art until such time as when it is to be administered to a recipient.

For example, a preparation may be frozen e.g., within about 24 or 48 hours of donation, i.e., immediately after collection to about 48 hours after collection and stored at about −20° C. or less, e.g., −80° C. or less, in some instances −90° C. or less, or −135° C. or less, e.g., −196° C. In some instances, the blood preparation is fresh-frozen, e.g., it is Fresh Frozen Plasma (FFP). In other instances, a chemical preservative, e.g., a cryopreservative, e.g., dimethyl sulfoxide (DMSO), may be added to aid in preservation. See, for example, Kreher et al. (2003) Journal of Immunological Methods 278:79-93; Reimann, et al. (2000) Clin. Diagn. Lab. Immunol. 7:352-359; and Romeu et al. (1992) J. Immunol. Methods 154:7-10. Cryopreservatives find particular use in maintaining the viability of cells in the blood product, for example, if the plasma-comprising blood product also comprises leukocytes, erythrocytes, etc. For example, 20% or more of the cells will survive upon thaw, for example, 40% or more, 60% or more, 80% or more cells, in some instances, 90% or more, such as 95% or more, 97% or more, or 99% or more of the cells will be viable after removal of the preservative. The blood product may be preserved prior to or after removal of proteins that are below a given threshold, such as described above, e.g., having an average molecular weight of 3.5 kD, 10 kD, 25 kD, 50 kD or less. In some instances, the blood product will be preserved prior to the depletion. In other instances, the blood product will be preserved after depletion. Following such techniques or techniques in the art, blood product may be stored for a year or more, e.g., 2, 3, 4, or 5 years or more, in some instances, 10, 20, 30 or 40 years or more, for example, 50, 60, 70 or 80 years. Upon thawing the blood product, the preservative, if used, may be replaced with any convenient solution, e.g., any suitable isotonic solution, in preparation for administration to the individual.

The plasma-comprising blood product may be administered using any convenient protocol for administering blood product to an individual. In some instances, the blood product is administered intravenously. The blood product may be mixed with intravenous solutions as known in the art, e.g., 5% dextrose in water, an isotonic electrolyte solution such as isotonic saline (0.9%), etc. The blood product may be administered using any convenient access device, e.g., needle for intravenous injection, compressor gun, peripheral cannula, central IV line, etc., e.g., implantable port, tunneled line, central venous lines, peripherally inserted central catheters and the like. Administration may be through any vein typically used for transfusion, e.g., subclavian, internal jugular, femoral, superior vena cava, inferior vena cava, right atrium, etc., in a volume and at a rate typically used for transfusion as known in the art, e.g., 10-20 ml per Kg weight of the individual per dose, at a rate of about 5 ml per minute.

In practicing the subject methods, the individual suffering from or at risk of suffering from an aging-associated condition, e.g., cognitive impairment or age-related dementia, is administered an effective amount of the young plasma product to treat the aging-associated condition, e.g., aging-associate cognitive impairment. In a clinical sense, an effective amount, or dose, of blood product is an amount of young plasma product that, when administered for a suitable period of time, usually at least about one week, and maybe about two weeks, or more, up to a period of about 3 weeks, 4 weeks, 8 weeks, or longer will evidence a reduction in the cognition decline and/or cognitive improvement in an individual suffering from impaired cognition or other type of degenerative condition due to natural aging or an aging associated disorder. For example, an effective dose is the dose that, when administered for a suitable period of time, such as at least about one week, and maybe about two weeks, or more, up to a period of about 3 weeks, 4 weeks, 8 weeks, or longer, will slow e.g., by about 20% or more, e.g., by 30% or more, by 40% or more, or by 50% or more, in some instances by 60% or more, by 70% or more, by 80% or more, or by 90% or more, e.g., will halt, cognitive decline in a patient suffering from natural aging or an aging-associated disorder. In some instances, an effective amount or dose of blood product will not only slow or halt the progression of the disease condition but will also induce the reversal of the condition, i.e., will cause an improvement in cognitive ability. For example, in some instances, an effective amount is the amount that when administered for a suitable period of time, usually at least about one week, and maybe about two weeks, or more, up to a period of about 3 weeks, 4 weeks, 8 weeks, or longer will improve the cognitive abilities of an individual suffering from an aging-associated cognitive impairment by, for example 1.5-fold, 2-fold, 3-fold, 4-fold, 5-fold, in some instances 6-fold, 7-fold, 8-fold, 9-fold, or 10-fold or more relative to cognition prior to administration of the blood product.

Cognition tests and IQ test for measuring cognitive ability, e.g., attention and concentration, the ability to learn complex tasks and concepts, memory, information processing, visuospatial function, the ability to produce and understanding language, the ability to solve problems and make decisions, and the ability to perform executive functions, are well known in the art, any of which may be used to measure the cognitive ability of the individual before and/or during and after treatment with the subject blood product, e.g., to confirm that an effective amount has been administered. These include, for example, the General Practitioner Assessment of Cognition (GPCOG) test, the Memory Impairment Screen, the Mini Mental State Examination (MMSE), the California Verbal Learning Test, Second Edition, Short Form, for memory, the Delis-Kaplan Executive Functioning System test, the Alzheimer's Disease Assessment Scale (ADAS-Cog), the Psychogeriatric Assessment Scale (PAS) and the like. Progression of functional brain improvements may be detected by brain imaging techniques, such as Magnetic Resonance Imaging (MRI) or Positron Emission Tomography (PET) and the like. A wide range of additional functional assessments may be applied to monitor activities of daily living, executive functions, mobility, etc. In some embodiments, the method comprises the step of measuring cognitive ability, and detecting a decreased rate of cognitive decline, a stabilization of cognitive ability, and/or an increase in cognitive ability after administration of the blood product as compared to the cognitive ability of the individual before the blood product was administered. Such measurements may be made a week or more after administration of the blood product, e.g., 1 week, 2 weeks, 3 weeks, or more, for instance, 4 weeks, 6 weeks, or 8 weeks or more, e.g., 3 months, 4 months, 5 months, or 6 months or more.

Biochemically speaking, by an "effective amount" or "effective dose" of blood product to prevent or treat an aging-associated cognitive impairment it is meant an amount of blood product that will inhibit, antagonize, decrease, reduce, or suppress by about 20% or more, e.g., by 30% or more, by 40% or more, or by 50% or more, in some instances by 60% or more, by 70% or more, by 80% or more, or by 90% or more, in some cases by about 100%, i.e., to negligible amounts, and in some instances reverse, the reduction in synaptic plasticity and loss of synapses that occurs during the natural aging process or during the progression of an aging-associated disorder. In other words, cells contacted with an effective amount of blood product will become more responsive to cues, e.g., activity cues, which promote the formation and maintenance of synapses.

Improvements in synaptic plasticity may be observed both in vitro and in vivo as an induction of long term potentiation. For example, the induction of LTP in neural circuits may be observed in awake individuals, e.g., by performing non-invasive stimulation techniques on awake individuals to induce LTP-like long-lasting changes in localized neural activity (Cooke S F, Bliss T V (2006) Plasticity in the human central nervous system. Brain. 129 (Pt 7):1659-73); mapping plasticity and increased neural circuit activity in individuals, e.g., by using positron emission tomography, functional magnetic resonance imaging, and/or transcranial magnetic stimulation (Cramer and Bastings (2000) Mapping clinically relevant plasticity after stroke. Neuropharmacology. 39(5): 842-51); and by detecting neural plasticity following learning, i.e., improvements in memory, e.g., by assaying retrieval-related brain activity (Buchmann A, et al. (2008) Prion protein M129V polymorphism affects retrieval-related brain activity. Neuropsychologia. 46(9):2389-402) or, e.g., by imaging brain tissue by functional magnetic resonance imaging (fMRI) following repetition priming with familiar and unfamiliar objects (Soldan A, et al. (2008) Global familiarity of visual stimuli affects repetition-related neural plasticity but not repetition priming. Neuroimage. 39(1): 515-26; Soldan A, et al. (2008) Aging does not affect brain patterns of repetition effects associated with perceptual priming of novel objects. J Cogn Neurosci. 20(10):1762-76). In some embodiments, the method includes the step of measuring synaptic plasticity, and detecting a decreased rate of loss of synaptic plasticity, a stabilization of synaptic plasticity, and/or an increase in synaptic plasticity after administration of the blood product as compared to the synaptic plasticity of the individual before the blood product was administered. Such measurements may be made a week or more after administration of the blood product, e.g., 1 week, 2 weeks, 3 weeks, or more, for instance, 4 weeks, 6 weeks, or 8 weeks or more, e.g., 3 months, 4 months, 5 months, or 6 months or more.

The calculation of the effective amount of blood product to be administered may vary. The final amount to be administered will be dependent upon the blood product administered, the route of administration, and the nature of the disorder or condition that is to be treated. In some instances, the blood product will be administered once. In other instances, the blood product will be administered more than once, e.g., regularly, e.g., weekly, monthly, biannually, or annually. For example, the blood product may be administered weekly for 2 weeks or more, e.g., 3 weeks, 4 weeks, 5 weeks, 6 weeks, 7 weeks, 8 weeks, more than 8 weeks, etc. As another example, the blood product may be administered monthly, e.g., for 2 months or more, e.g., 3 months, 4 months, 5 months, 6 months, 7 months, 8 months, 9 months, 10 months, 11 months, 12 months, or more than 12 months.

As another example, the blood product may be administered biannually, or annually. It will be understood by those of skill in the art that an initial dose may be administered for such periods of time, followed by maintenance doses, which, in some cases, will be at a reduced dosage.

In some embodiments, the subject blood product may be provided in conjunction with an active agent having activity suitable to treat aging-associated cognitive impairment. For example, a number of active agents have been shown to have some efficacy in treating the cognitive symptoms of Alzheimer's disease (e.g., memory loss, confusion, and problems with thinking and reasoning), e.g., cholinesterase inhibitors (e.g., Donepezil, Rivastigmine, Galantamine, Tacrine), Memantine, and Vitamin E. As another example, a number of agents have been shown to have some efficacy in treating behavioral or psychiatric symptoms of Alzheimer's Disease, e.g., citalopram (Celexa), fluoxetine (Prozac), paroxeine (Paxil), sertraline (Zoloft), trazodone (Desyrel), lorazepam (Ativan), oxazepam (Serax), aripiprazole (Abilify), clozapine (Clozaril), haloperidol (Haldol), olanzapine (Zyprexa), quetiapine (Seroquel), risperidone (Risperdal), and ziprasidone (Geodon). In some embodiments, the subject blood product is provided before the second agent. In some embodiments, the subject blood product is provided after the second agent. In some embodiments, the subject blood product is provided concurrently with the second agent. In certain such embodiments, the subject blood product comprises one or more of these additional agents.

In some aspects of the subject methods, the method further comprises the step of measuring cognition and/or synaptic plasticity after treatment, e.g., using the methods described herein or known in the art, and determining that the rate of cognitive decline or loss of synaptic plasticity have been reduced and/or that cognitive ability or synaptic plasticity have improved in the individual. In some such instances, the determination is made by comparing the results of the cognition or synaptic plasticity test to the results of the test performed on the same individual at an earlier time, e.g., 2 weeks earlier, 1 month earlier, 2 months earlier, 3 months earlier, 6 months earlier, 1 year earlier, 2 years earlier, 5 years earlier, or 10 years earlier, or more.

In some embodiments, the subject methods further include diagnosing an individual as having a cognitive impairment, e.g., using the methods described herein or known in the art for measuring cognition and synaptic plasticity, prior to administering the subject plasma-comprising blood product. In some instances, the diagnosing will comprise measuring cognition and/or synaptic plasticity and comparing the results of the cognition or synaptic plasticity test to one or more references, e.g., a positive control and/or a negative control. For example, the reference may be the results of the test performed by one or more age-matched individuals that experience aging-associated cognitive impairments (i.e., positive controls) or that do not experience aging-associated cognitive impairments (i.e., negative controls). As another example, the reference may be the results of the test performed by the same individual at an earlier time, e.g., 2 weeks earlier, 1 month earlier, 2 months earlier, 3 months earlier, 6 months earlier, 1 year earlier, 2 years earlier, 5 years earlier, or 10 years earlier, or more.

In some embodiments, the subject methods further comprise diagnosing an individual as having an aging-associated disorder, e.g., Alzheimer's disease, Parkinson's disease, frontotemporal dementia, progressive supranuclear palsy, Huntington's disease, amyotrophic lateral sclerosis, spinal muscular atrophy, multiple sclerosis, multi-system atrophy, glaucoma, ataxias, myotonic dystrophy, dementia, and the like. Methods for diagnosing such aging-associated disorders are well-known in the art, any of which may be used by the ordinarily skilled artisan in diagnosing the individual. In some embodiments, the subject methods further comprise both diagnosing an individual as having an aging-associated disorder and as having a cognitive impairment.

As summarized above, aspects of the invention further include treating a subject for aging-associated conditions that are not aging-associated cognitive impairment conditions. For example, aspects of the invention include administration of young plasma products for the treatment of aging associated decline in peripheral organ function. As demonstrated in the experimental section below, rejuvenating and regenerative effects of young blood products were observed in muscle, liver, brain, heart, and pancreas. In some embodiments, the peripheral organ that benefits from administration with young plasma will include, but not be limited to, muscle, liver, brain, heart, pancreas, as well as other peripheral organs. In some embodiments the organ that will benefit from systemic administration of plasma will be the recipient's blood. Specifically, intercellular communication factors, which change with age, will be restored to more youthful levels; e.g., inflammatory factors, which increase with age will be reduced, while trophic factors, which decrease with age, will be increased. In some instances, the methods result in a change in expression levels of one or more genes in one or more tissues of the host, e.g., as compared to a suitable control (such as described in the Experimental section, below). The change in expression level a given gene may be 0.5 fold or greater, such as 1.0 fold or greater, including 1.5 fold or greater. The tissue may vary, and in some instances is nervous system tissue, e.g., central nervous system tissue, including brain tissue, e.g., hippocampal tissue. In some instances, the one or more genes whose expression is modulated, e.g., enhanced, is a gene encoding a product that is a member of a plasticity related signaling pathway (i.e., a synaptic plasticity regulation gene), e.g., Tlr4, Gria1, Kcnj10, Kdr, Ncam, Sdfr1, Egr1, Fos proteins, e.g., c-Fos, Drd1a, Stxbp1, Mef2c, Cntn2, Junb, Bdnf and CamK2a, etc. In some instances, the modulation of hippocampal gene expression is manifested as enhanced hippocampal plasticity, e.g., as compared to a suitable control. In some instances, the one or more genes whose expression is modulated, e.g., enhanced, is a gene encoding a product that is a member of network related to synaptic plasticity and learning and memory, such as but not limited to: RELN, NTRK3, EPHA4, etc.

In some instances, treatment results in an enhancement in the levels of one or more proteins in one or more tissues of the host, e.g., as compared to a suitable control (such as described in the Experimental section, below). The change in protein level of a given protein may be 0.5 fold or greater, such as 1.0 fold or greater, including 1.5 fold or greater, where in some instances the level may approach that of a healthy wild-type level, e.g., within 50% or less, such as 25% or less, including 10% or less, e.g., 5% or less of the healthy wild-type level. The tissue may vary, and in some instances is nervous system tissue, e.g., central nervous system tissue, including brain tissue, e.g., hippocampal tissue. Target proteins of interest include, but are not limited to, synaptic proteins, e.g., synaptophysin, calcium bindings proteins, e.g., calbindin, In some instances, the methods result in one or more structural changes in one or more tissues. The tissue may vary, and in some instances is nervous system tissue, e.g., central nervous system tissue, including brain tissue, e.g., hippocampal tissue. Structure changes of interest include an increase in dendritic spine density of mature neurons in the dentate gyrus (DG) of the hippocampus, e.g., as compared to a suitable control. In some instances, the modulation of hippocampal structure is manifested as enhanced synapse formation, e.g., as compared to a suitable control. In some instances, the methods may result in an enhancement of long term potentiation, e.g., as compared to a suitable control.

In some instances, the methods result in enhancement in learning and memory, e.g., as compared to a suitable control. Enhancement in learning and memory may be evaluated in a number of different ways, e.g., the contextual fear conditioning and/or radial arm water maze (RAWM) paradigms described in the experimental section, below. When measured by contextual fear conditioning, treatment results in some instances in increased freezing in contextual, but not cued, memory testing. When measured by RAWM, treatment results in some instances in enhanced learning and memory for platform location during the testing phase of the task. In some instances, treatment is manifested as enhanced cognitive improvement in hippocampal-dependent learning and memory, e.g., as compared to a suitable control.

In some instances, treatment in accordance with methods described herein results in organism wide changes in intercellular communication proteins in blood, where the resultant protein changes may have pleiotropic beneficial effects on multiple tissues. Proteins of interest whose levels may be beneficially enhanced following treatment include, but are not limited to: growth factors, including IL-22, LIF, etc.

Aspects of the invention further include methods of screening candidate compositions for activity with respect to treatment of aging associated conditions, e.g., for use in methods of the invention. Embodiments of methods include administering a candidate composition to a suitable animal model, and evaluating the animal model following administration to assess whether the candidate composition has a desired activity. Animal models of interest include non-human mammalian models, e.g., murine models, that are able to tolerate human blood products, e.g., plasma, with experiencing harmful effects of immune rejection. Such animals include murine models that lack a functional immune system, such as NOD/SCID (NSG) mice (Shultz et al. Human lymphoid and myeloid cell development in NOD/LtSz-scid IL2R gamma null mice engrafted with mobilized human hemopoietic stem cells. J Immunol 174, 6477-6489 (2005)). The candidate composition may be any composition, such as but not limited to the blood products described above. The animals may be assessed in a number of different ways, including at the gene expression level, protein level, structural level and behavioral level, e.g., using any of the assays and protocols described herein.

Utility

The subject methods and young plasma-comprising blood products find use in treating, including preventing, aging-associated conditions, such as impairments in the cognitive ability of individuals. Individuals suffering from or at risk of developing an aging-associated cognitive impairment that will benefit from treatment with the subject plasma-comprising blood product, e.g., by the methods disclosed herein, include individuals that are about 50 years old or older, e.g., 60 years old or older, 70 years old or older, 80 years old or older, 90 years old or older, and usually no older than 100 years old, i.e., between the ages of about 50 and 100, e.g., 50, 55, 60, 65, 70, 75, 80, 85, 90, 95 or about 100 years old, and are suffering from cognitive impairment associated with natural aging process, e.g., mild cognitive impairment (M.C.I.); and individuals that are about 50 years old or older, e.g., 60 years old or older, 70 years old or older, 80 years old or older, 90 years old or older, and usually no older than 100 years old, i.e., between the ages of about 50 and 90, e.g., 50, 55, 60, 65, 70, 75, 80, 85, 90, 95 or about 100 years old, that have not yet begun to show symptoms of cognitive impairment. Examples of cognitive impairments that are due to natural aging include the following:

Mild cognitive impairment (M.C.I.) is a modest disruption of cognition that manifests as problems with memory or other mental functions such as planning, following instructions, or making decisions that have worsened over time while overall mental function and daily activities are not impaired. Thus, although significant neuronal death does not typically occur, neurons in the aging brain are vulnerable to sub-lethal age-related alterations in structure, synaptic integrity, and molecular processing at the synapse, all of which impair cognitive function.

Individuals suffering from or at risk of developing an aging-associated cognitive impairment that will benefit from treatment with the subject plasma-comprising blood product, e.g., by the methods disclosed herein, also include individuals of any age that are suffering from a cognitive impairment due to an aging-associated disorder; and individuals of any age that have been diagnosed with an aging-associated disorder that is typically accompanied by cognitive impairment, where the individual has not yet begun to present with symptoms of cognitive impairment. Examples of such aging-associated disorders include the following:

Alzheimer's Disease (AD).

Alzheimer's disease is a progressive, inexorable loss of cognitive function associated with an excessive number of senile plaques in the cerebral cortex and subcortical gray matter, which also contains b-amyloid and neurofibrillary tangles consisting of tau protein. The common form affects persons >60 yr old, and its incidence increases as age advances. It accounts for more than 65% of the dementias in the elderly.

The cause of Alzheimer's disease is not known. The disease runs in families in about 15 to 20% of cases. The remaining, so-called sporadic cases have some genetic determinants. The disease has an autosomal dominant genetic pattern in most early-onset and some late-onset cases but a variable late-life penetrance. Environmental factors are the focus of active investigation.

In the course of the disease, synapses, and ultimately neurons are lost within the cerebral cortex, hippocampus, and subcortical structures (including selective cell loss in the nucleus basalis of Meynert), locus caeruleus, and nucleus raphae dorsalis. Cerebral glucose use and perfusion is reduced in some areas of the brain (parietal lobe and temporal cortices in early-stage disease, prefrontal cortex in late-stage disease). Neuritic or senile plaques (composed of neurites, astrocytes, and glial cells around an amyloid core) and neurofibrillary tangles (composed of paired helical filaments) play a role in the pathogenesis of Alzheimer's disease. Senile plaques and neurofibrillary tangles occur with normal aging, but they are much more prevalent in persons with Alzheimer's disease.

Parkinson's Disease.

Parkinson's Disease (PD) is an idiopathic, slowly progressive, degenerative CNS disorder characterized by slow and decreased movement, muscular rigidity, resting tremor, and postural instability. Originally considered primarily a motor disorder, PD is now recognized to also affect cognition, behavior, sleep, autonomic function, and sensory function. The most common cognitive impairments include an impairment in attention and concentration, working memory, executive function, producing language, and visuospatial function.

In primary Parkinson's disease, the pigmented neurons of the substantia nigra, locus caeruleus, and other brain stem dopaminergic cell groups are lost. The cause is not known. The loss of substantia nigra neurons, which project to the caudate nucleus and putamen, results in depletion of the neurotransmitter dopamine in these areas. Onset is generally after age 40, with increasing incidence in older age groups.

Secondary parkinsonism results from loss of or interference with the action of dopamine in the basal ganglia due to other idiopathic degenerative diseases, drugs, or exogenous toxins. The most common cause of secondary parkinsonism is ingestion of antipsychotic drugs or reserpine, which produce parkinsonism by blocking dopamine receptors. Less common causes include carbon monoxide or manganese poisoning, hydrocephalus, structural lesions (tumors, infarcts affecting the midbrain or basal ganglia), subdural hematoma, and degenerative disorders, including striatonigral degeneration.

Frontotemporal Dementia.

Frontotemporal dementia (FTD) is a condition resulting from the progressive deterioration of the frontal lobe of the brain. Over time, the degeneration may advance to the temporal lobe. Second only to Alzheimer's disease (AD) in prevalence, FTD accounts for 20% of pre-senile dementia cases. Symptoms are classified into three groups based on the functions of the frontal and temporal lobes affected: Behavioural variant FTD (bvFTD), with symptoms include lethargy and aspontaneity on the one hand, and disinhibition on the other; progressive nonfluent aphasia (PNFA), in which a breakdown in speech fluency due to articulation difficulty, phonological and/or syntactic errors is observed but word comprehension is preserved; and semantic dementia (SD), in which patients remain fluent with normal phonology and syntax but have increasing difficulty with naming and word comprehension. Other cognitive symptoms common to all FTD patients include an impairment in executive function and ability to focus. Other cognitive abilities, including perception, spatial skills, memory and praxis typically remain intact. FTD can be diagnosed by observation of reveal frontal lobe and/or anterior temporal lobe atrophy in structural MRI scans.

A number of forms of FTD exist, any of which may be treated or prevented using the subject methods and compositions. For example, one form of frontotemporal dementia is Semantic Dementia (SD). SD is characterized by a loss of semantic memory in both the verbal and non-verbal domains. SD patients often present with the complaint of word-finding difficulties. Clinical signs include fluent aphasia, anomia, impaired comprehension of word meaning, and associative visual agnosia (the inability to match semantically related pictures or objects). As the disease progresses, behavioral and personality changes are often seen similar to those seen in frontotemporal dementia although cases have been described of 'pure' semantic dementia with few late behavioral symptoms. Structural MRI imaging shows a characteristic pattern of atrophy in the temporal lobes (predominantly on the left), with inferior greater than superior involvement and anterior temporal lobe atrophy greater than posterior.

As another example, another form of frontotemporal dementia is Pick's disease (PiD, also PcD). A defining characteristic of the disease is build-up of tau proteins in neurons, accumulating into silver-staining, spherical aggregations known as "Pick bodies". Symptoms include loss of speech (aphasia) and dementia. Patients with orbitofrontal dysfunction can become aggressive and socially inappropriate. They may steal or demonstrate obsessive or repetitive stereotyped behaviors. Patients with dorsomedial or dorsolateral frontal dysfunction may demonstrate a lack of concern, apathy, or decreased spontaneity. Patients can demonstrate an absence of self-monitoring, abnormal self-awareness, and an inability to appreciate meaning. Patients with gray matter loss in the bilateral posterolateral orbitofrontal cortex and right anterior insula may demonstrate changes in eating behaviors, such as a pathologic sweet tooth. Patients with more focal gray matter loss in the anterolateral orbitofrontal cortex may develop hyperphagia. While some of the symptoms can initially be alleviated, the disease progresses and patients often die within two to ten years.

Huntington's Disease.

Huntington's disease (HD) is a hereditary progressive neurodegenerative disorder characterized by the development of emotional, behavioral, and psychiatric abnormalities; loss of intellectual or cognitive functioning; and movement abnormalities (motor disturbances). The classic signs of HD include the development of chorea—involuntary, rapid, irregular, jerky movements that may affect the face, arms, legs, or trunk—as well as cognitive decline including the gradual loss of thought processing and acquired intellectual abilities. There may be impairment of memory, abstract thinking, and judgment; improper perceptions of time, place, or identity (disorientation); increased agitation; and personality changes (personality disintegration). Although symptoms typically become evident during the fourth or fifth decades of life, the age at onset is variable and ranges from early childhood to late adulthood (e.g., 70s or 80s).

HD is transmitted within families as an autosomal dominant trait. The disorder occurs as the result of abnormally long sequences or "repeats" of coded instructions within a gene on chromosome 4 (4p16.3). The progressive loss of nervous system function associated with HD results from loss of neurons in certain areas of the brain, including the basal ganglia and cerebral cortex.

Amyotrophic Lateral Sclerosis.

Amyotrophic lateral sclerosis (ALS) is a rapidly progressive, invariably fatal neurological disease that attacks motor neurons. Muscular weakness and atrophy and signs of anterior horn cell dysfunction are initially noted most often in the hands and less often in the feet. The site of onset is random, and progression is asymmetric. Cramps are common and may precede weakness. Rarely, a patient survives 30 years; 50% die within 3 years of onset, 20% live 5 years, and 10% live 10 years. Diagnostic features include onset during middle or late adult life and progressive, generalized motor involvement without sensory abnormalities. Nerve conduction velocities are normal until late in the disease. Recent studies have documented the presentation of cognitive impairments as well, particularly a reduction in immediate verbal memory, visual memory, language, and executive function.

A decrease in cell body area, number of synapses and total synaptic length has been reported in even normal-appearing neurons of the ALS patients. It has been suggested that when the plasticity of the active zone reaches its limit, a continuing loss of synapses can lead to functional impairment. Promoting the formation or new synapses or preventing synapse loss may maintain neuron function in these patients.

Multiple Sclerosis.

Multiple Sclerosis (MS) is characterized by various symptoms and signs of CNS dysfunction, with remissions and recurring exacerbations. The most common presenting symptoms are paresthesias in one or more extremities, in the trunk, or on one side of the face; weakness or clumsiness of a leg or hand; or visual disturbances, e.g., partial blindness and pain in one eye (retrobulbar optic neuritis), dimness of vision, or scotomas. Common cognitive impairments include impairments in memory (acquiring, retaining, and retrieving new information), attention and concentration (particularly divided attention), information processing, executive functions, visuospatial functions, and verbal fluency. Common early symptoms are ocular palsy resulting in double vision (diplopia), transient weakness of one or more extremities, slight stiffness or unusual fatigability of a limb, minor gait disturbances, difficulty with bladder control, vertigo, and mild emotional disturbances; all indicate scattered CNS involvement and often occur months or years before the disease is recognized. Excess heat may accentuate symptoms and signs.

The course is highly varied, unpredictable, and, in most patients, remittent. At first, months or years of remission may separate episodes, especially when the disease begins with retrobulbar optic neuritis. However, some patients have frequent attacks and are rapidly incapacitated; for a few the course can be rapidly progressive.

Glaucoma.

Glaucoma is a common neurodegenerative disease that affects retinal ganglion cells (RGCs). Evidence supports the existence of compartmentalized degeneration programs in synapses and dendrites, including in RGCs. Recent evidence also indicates a correlation between cognitive impairment in older adults and glaucoma (Yochim B P, et al. Prevalence of cognitive impairment, depression, and anxiety symptoms among older adults with glaucoma. J Glaucoma. 2012; 21(4):250-254).

Myotonic Dystrophy.

Myotonic dystrophy (DM) is an autosomal dominant multisystem disorder characterized by dystrophic muscle weakness and myotonia. The molecular defect is an expanded trinucleotide (CTG) repeat in the 3' untranslated region of the myotonin-protein kinase gene on chromosome 19q. Symptoms can occur at any age, and the range of clinical severity is broad. Myotonia is prominent in the hand muscles, and ptosis is common even in mild cases. In severe cases, marked peripheral muscular weakness occurs, often with cataracts, premature balding, hatchet facies, cardiac arrhythmias, testicular atrophy, and endocrine abnormalities (e.g., diabetes mellitus). Mental retardation is common in severe congenital forms, while an aging-related decline of frontal and temporal cognitive functions, particularly language and executive functions, is observed in milder adult forms of the disorder. Severely affected persons die by their early 50s.

Dementia.

Dementia describes class of disorders having symptoms affecting thinking and social abilities severely enough to interfere with daily functioning. Other instances of dementia in addition to the dementia observed in later stages of the aging-associated disorders discussed above include vascular dementia, and dementia with Lewy bodies, described below.

In vascular dementia, or "multi-infarct dementia", cognitive impairment is caused by problems in supply of blood to the brain, typically by a series of minor strokes, or sometimes, one large stroke preceded or followed by other smaller strokes. Vascular lesions can be the result of diffuse cerebrovascular disease, such as small vessel disease, or focal lesions, or both. Patients suffering from vascular dementia present with cognitive impairment, acutely or subacutely, after an acute cerebrovascular event, after which progressive cognitive decline is observed. Cognitive impairments are similar to those observed in Alzheimer's disease, including impairments in language, memory, complex visual processing, or executive function, although the related changes in the brain are not due to AD pathology but to chronic reduced blood flow in the brain, eventually resulting in dementia. Single photon emission computed tomography (SPECT) and positron emission tomography (PET) neuroimaging may be used to confirm a diagnosis of multi-infarct dementia in conjunction with evaluations involving mental status examination.

Dementia with Lewy bodies (DLB, also known under a variety of other names including Lewy body dementia, diffuse Lewy body disease, cortical Lewy body disease, and senile dementia of Lewy type) is a type of dementia characterized anatomically by the presence of Lewy bodies (clumps of alpha-synuclein and ubiquitin protein) in neurons, detectable in post mortem brain histology. Its primary feature is cognitive decline, particularly of executive functioning. Alertness and short term memory will rise and fall. Persistent or recurring visual hallucinations with vivid and detailed pictures are often an early diagnostic symptom. DLB it is often confused in its early stages with Alzheimer's disease and/or vascular dementia, although, where Alzheimer's disease usually begins quite gradually, DLB often has a rapid or acute onset. DLB symptoms also include motor symptoms similar to those of Parkinson's. DLB is distinguished from the dementia that sometimes occurs in Parkinson's disease by the time frame in which dementia symptoms appear relative to Parkinson symptoms. Parkinson's disease with dementia (PDD) would be the diagnosis when dementia onset is more than a year after the onset of Parkinson's. DLB is diagnosed when cognitive symptoms begin at the same time or within a year of Parkinson symptoms.

Progressive Supranuclear Palsy.

Progressive supranuclear palsy (PSP) is a brain disorder that causes serious and progressive problems with control of gait and balance, along with complex eye movement and thinking problems. One of the classic signs of the disease is an inability to aim the eyes properly, which occurs because of lesions in the area of the brain that coordinates eye movements. Some individuals describe this effect as a blurring. Affected individuals often show alterations of mood and behavior, including depression and apathy as well as progressive mild dementia. The disorder's long name indicates that the disease begins slowly and continues to get worse (progressive), and causes weakness (palsy) by damaging certain parts of the brain above pea-sized structures called nuclei that control eye movements (supranuclear). PSP was first described as a distinct disorder in 1964, when three scientists published a paper that distinguished the condition from Parkinson's disease. It is sometimes referred to as Steele-Richardson-Olszewski syndrome, reflecting the combined names of the scientists who defined the disorder. Although PSP gets progressively worse, no one dies from PSP itself.

Ataxia.

People with ataxia have problems with coordination because parts of the nervous system that control movement and balance are affected. Ataxia may affect the fingers, hands, arms, legs, body, speech, and eye movements. The word ataxia is often used to describe a symptom of incoordination which can be associated with infections, injuries, other diseases, or degenerative changes in the central nervous system. Ataxia is also used to denote a group of specific degenerative diseases of the nervous system called the hereditary and sporadic ataxias which are the National Ataxia Foundation's primary emphases.

Multiple-System Atrophy.

Multiple-system atrophy (MSA) is a degenerative neurological disorder. MSA is associated with the degeneration of nerve cells in specific areas of the brain. This cell degeneration causes problems with movement, balance, and other autonomic functions of the body such as bladder control or blood-pressure regulation. The cause of MSA is unknown and no specific risk factors have been identified. Around 55% of cases occur in men, with typical age of onset in the late 50s to early 60s. MSA often presents with some of the same symptoms as Parkinson's disease. However, MSA patients generally show minimal if any response to the dopamine medications used for Parkinson's.

In some embodiments, the subject methods and compositions find use in slowing the progression of aging-associated cognitive impairment. In other words, cognitive abilities in the individual will decline more slowly following treatment by the disclosed methods than prior to or in the absence of treatment by the disclosed methods. In some such instances, the subject methods of treatment include measuring the progression of cognitive decline after treatment, and determining that the progression of cognitive decline is reduced. In some such instances, the determination is made by comparing to a reference, e.g., the rate of cognitive decline in the individual prior to treatment, e.g., as determined by measuring cognition prior at two or more time points prior to administration of the subject blood product.

The subject methods and compositions also find use in stabilizing the cognitive abilities of an individual, e.g., an individual suffering from aging-associated cognitive decline or an individual at risk of suffering from aging-associated cognitive decline. For example, the individual may demonstrate some aging-associated cognitive impairment, and progression of cognitive impairment observed prior to treatment with the disclosed methods will be halted following treatment by the disclosed methods. As another example, the individual may be at risk for developing an aging-associated cognitive decline (e.g., the individual may be aged 50 years old or older, or may have been diagnosed with an aging-associated disorder), and the cognitive abilities of the individual are substantially unchanged, i.e., no cognitive decline can be detected, following treatment by the disclosed methods as compared to prior to treatment with the disclosed methods.

The subject methods and compositions also find use in reducing cognitive impairment in an individual suffering from an aging-associated cognitive impairment. In other words, cognitive ability is improved in the individual following treatment by the subject methods. For example, the cognitive ability in the individual is increased, e.g., by 2-fold or more, 5-fold or more, 10-fold or more, 15-fold or more, 20-fold or more, 30-fold or more, or 40-fold or more, including 50-fold or more, 60-fold or more, 70-fold or more, 80-fold or more, 90-fold or more, or 100-fold or more, following treatment by the subject methods relative to the cognitive ability that is observed in the individual prior to treatment by the subject methods. In some instances, treatment by the subject methods and compositions restores the cognitive ability in the individual suffering from aging-associated cognitive decline, e.g., to their level when the individual was about 40 years old or less. In other words, cognitive impairment is abrogated.

Reagents, Devices and Kits

Also provided are reagents, devices and kits thereof for practicing one or more of the above-described methods. The subject reagents, devices and kits thereof may vary greatly.

Reagents and devices of interest include those mentioned above with respect to the methods of preparing plasma-comprising blood product for transfusion into a subject in need thereof, for example, anti-coagulants, cryopreservatives, buffers, isotonic solutions, etc.

Also of interest are devices such as sterile cartridges, or columns, comprising a matrix that will retain or retard the flow of proteins having an average molecular weight of 3.5 kD or less. Such a cartridge will comprise (i) an inlet, (ii) a size exclusion matrix, (iii) an outlet; (iv) a housing that contains the matrix therein; and (v) a fluid path through the housing that connects the inlet to the outlet. The cartridge may comprise a support comprising at least one fluid-permeable membrane, one or more porous fiber(s), or a plurality of particles. The support may be formed separately from the housing or as an integral part thereof, and may be manufactured from any convenient material include, for example, alumina, cellulose, dextran, polyacrylamide, polyacrylate, polyamide, or silica. The cartridge may be configured for separation by membrane filtration or column chromatography, and may be able to bind from about a suitable amount of protein, e.g., grams of protein. Aseptic packaging may surround the cartridge to maintain it, the inlet, and the outlet in sterile and pyrogen-free conditions. The housing may be sized to comprise a volume of about 200-500 ml. Larger cartridges are also envisioned, e.g., for the filtration of larger volumes of blood product. Cartridge parts (e.g., inlet, outlet, and housing) may be manufactured from glass, polypropylene, polystyrene, or stainless steel. An external pump may provide line pressure through flexible tubing to the cartridge and, thereby, control the flow rate of a fluid phase through the matrix and column.

Kits comprising these reagents and/or cartridges are also envisioned. Kits may also comprise blood collection bags, tubing, needles, centrifugation tubes, and the like.

In yet other embodiments, kits as described herein include two or more containers of young plasma product, such as three or more, four or more, five or more, including six or more containers of young plasma product. In some instances, the number of distinct containers of young plasma product in the kit may be 9 or more, 12 or more, 15 or more, 18 or more, 21 or more, 24 or more 30 or more, including 36 or more, e.g., 48 or more. Each container my have associated therewith identifying information which includes various data about the young plasma product contained therein, which identifying information may include one or more of the age of the donor of the young plasma product, processing details regarding the young plasma product, e.g., whether the plasma product was processed to remove proteins above an average molecule weight (such as described above), blood type details, etc. In some instances, each container in the kit includes identifying information about the young plasma contained therein, and the identifying information includes information about the donor age of the young plasma product, e.g., the identifying information provides confirming age-related data of the young plasma product donor (where such identifying information may be the age of the donor at the time of harvest). In some instances, each container of the kit contains a young plasma product from a donor of substantially the same age, i.e., all of the containers include product from donors that are substantially the same, if not the same, age. By substantially the same age is meant that the various donors from which the young plasma products of the kits are obtained differ in each, in some instances, by 5 years or less, such as 4 years or less, e.g., 3 years or less, including 2 years or less, such as 1 year or less, e.g., 9 months or less, 6 months or less, 3 months or less, including 1 month or less. The identifying information can be present on any convenient component of the container, such as a label, an RFID chip, etc. The identifying information may be human readable, computer readable, etc., as desired. The containers may have any convenient configuration. While the volume of the containers may vary, in some instances the volumes range from 10 ml to 5000 ml, such as 25 ml to 2500 ml, e.g., 50 ml to 1000 ml, including 100 ml to 500 ml. The containers may be rigid or flexible, and may be fabricated from any convenient material, e.g., polymeric materials, including medical grade plastic materials. In some instances, the containers have a bag or pouch configuration. In addition to the containers, such kits may further include administration devices, e.g., as described above. The components of such kits may be provided in any suitable packaging, e.g., a box or analogous structure, configured to hold the containers and other kit components.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, portable flash drive, etc., on which the information has been recorded. Yet another means that may be present is a website address which may be used via the internet to access the information at a removed site. Any convenient means may be present in the kits.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, and kits for genetic manipulation referred to in this disclosure are available from commercial vendors such as BioRad, Stratagene, Invitrogen, Sigma-Aldrich, and Clontech.

Example 1

It is shown here that exposure of an old animal to young blood can counteract the pre-existing effects of brain aging at a structural, functional and cognitive level. Using genome-wide microarray analysis of heterochronic parabionts—in which the circulatory systems of young and old animals are connected—an expression profile was identified indicative of enhanced plasticity in the hippocampus of old mice. Moreover, structural enhancements in the dendritic spine density of mature neurons and functional improvements in synaptic plasticity were observed in the hippocampi of old heterochronic parabionts. Lastly, intravenous administration of young blood plasma into old mice improved age-related cognitive impairments in both contextual fear conditioning and spatial learning and memory. Together, these data indicate that exposure to young blood late in life is capable of reversing age-related changes present in the old brain.

Materials and Methods

Animals. C57BL/6 young mice (Jackson Laboratory) and C57BL/6 aged mice (National Institutes on Aging) were housed under specific pathogen-free conditions under a 12 h light-dark cycle and all animal handling and use was in accordance with institutional guidelines approved by the VA Palo Alto Committee on Animal Research.

Parabiosis surgery followed previously described procedures (Villeda, S. A. et al. The ageing systemic milieu negatively regulates neurogenesis and cognitive function. Nature 477(7362), 90-94 (2011); Conboy, I. M. et al., Rejuvenation of aged progenitor cells by exposure to a young systemic environment. Nature 433 (7027), 760-764 (2005)). Mirror-image incisions at the left and right flanks were made through the skin and shorter incisions made through the abdominal wall. The peritoneal openings of the adjacent parabionts were sutured together. Elbow and knee joints from each parabiont were sutured together and the skin of each mouse was stapled (9 mm Autoclip, Clay Adams) to the skin of the adjacent parabiont. Each mouse was injected subcutaneously with Baytril antibiotic and Buprenex as directed for pain and monitored during recovery.

Gene Microarray Analysis.

Hippocampi from isochronic and heterochronic parabionts were dissected and total RNA was extracted using Trizol reagent (Invitrogen). cDNA and cRNA were sequentially synthesized and amplified using RNA Amplification Kit (Ambion) according to the manufacture's protocol. cRNA was then hybridized to Illumina beadchip array MouseWG-6 v2.0 (Illumina) according to the manufacturer's instructions. Data were analyzed by Illumina beadstudio data analysis software (Illumina) following manufacturer's guidelines. Cluster 3.0 software was used for unsupervised hierarchical clustering of Z-scored data sets. Java TreeView software was used for generating heat maps. A cut-off at $P<0.01$ and absolute d-score>2 (FIG. 2b) or d-score>1.5 (FIG. 2b), respectively, based on Significance Analysis of Microarray software (SAM 3.00 algorithm; found on the world wide web by placing a "www." before "stat.stanford.edu/~tibs/SAM/index.htm" was applied for data set analysis. Significantly changed probe sets were analyzed for statistically enriched pathways using Ingenuity Pathway Analysis (IPA; Ingenuity Systems, www.ingenuity.com) and categorized for biological function using AmiGO (The Gene Ontology Consortium, found on the world wide web by placing a "www." before "godatabase.org/cgi-bin/amigo/go/cgi".

Immunohistochemistry.

Tissue processing and immunohistochemistry was performed on free-floating sections following standard published techniques (Ruckh et al., Rejuvenation of Regeneration in the Aging Central Nervous System, Stem Cell 10, 96-103 (2012)). Mice were anesthetized with chloral hydrate (Sigma-Aldrich), transcardially perfused with 0.9% saline and brains removed and fixed in phosphate-buffered 4% paraformaldehyde for 48 h before cryprotection with 30% sucrose. Free floating coronal sections (40 µm) were incubated overnight with either, rabbit anti-Egr-1 (1:500; Santa Cruz), rabbit anti-cFos (1:500; Millipore) or rabbit anti-phospho CREB (1:5000; Oncogene Research Products) primary antibodies and staining was revealed using biotinylated secondary antibodies and the ABC kit (Vector) with Diaminobenzidine (DAB, Sigma-Aldrich). Individual cell number was quantified Egr-1 and cFos, and phosphorylated-CREB was quantified as mean signal intensity using NIH ImageJ software.

Golgi Staining.

After brain removal hemispheres were immersed in 10 ml 'modified Golgi-Cox staining solution' (Jing, Deqiang and Lee, Francis, Cornell University) for 7-10 days at room temperature in the dark. Brains were transferred to 30% sucrose in dH2O at 4° C. for 72 hrs. Sections (150 µm) were mounted onto slides coated with 0.3% gelatin in dH2O. After briefly drying, slides were dipped in 40% sucrose 3 times and air-dried for 72 hrs in the dark. Slides were immersed into dH2O, 3×10 min with gentle shaking, then transferred to a developing solution for 6 min. Slides were then rinsed 3×10 min in dH2O, dehydrated through graded ethanol, immersed in Histoclear, and then coverslipped using DPX mounting medium. Neurons were traced at 100× and all subsequent analysis was done using Neurolucida Software (v10, MBF Bioscience). Sholl analysis was performed for each neuron by placing concentric spheres at 10 µm intervals from the soma. The number of times the dendrite intersected each sphere and the total dendritic length within each sphere was quantified. Dendritic length was summed across distance in the x, y, and z planes and across multiple dendritic branches of the neurons that are contained within each radius.

Extracellular Electrophysiology.

Extracellular electrophysiology was performed as previously described (Rosenzweig, E. S. & Barnes, C. A., (2003) Impact of aging on hippocampal function: plasticity, network dynamics, and cognition. Progress Neurobiol. 69(3), 143-179). Acute hippocampal slices (400 µm thick) were prepared from old parabionts. Slices were maintained in artificial cerebrospinal fluid (ACSF; in mM: NaCl 124.0; KCl 2.5; KH2PO4 1.2; CaCl2 2.4; MgSO4 1.3; NaHCO$_3$ 26.0; glucose 10.0) continuously oxygenated with 5% CO2/95% 02. Recordings were performed with an Axopatch-2B amplifier and pClamp 10.2 software (Axon Instruments). Submerged slices were continuously perfused with oxygenated ACSF at a flow rate of 2 ml/min from a reservoir by gravity feeding. Field potential (population spikes) was recorded using glass microelectrodes filled with ACSF (resistance: 4-8 MO). Biphasic current pulses (0.2 ms duration for one phase, 0.4 ms in total) were delivered in 10 s intervals through a concentric bipolar stimulating electrode (FHC, Inc.). No obvious synaptic depression or facilitation was observed with this frequency stimulation. To record field population spikes in the dentate gyrus, the recording electrode was placed in the lateral or medial side of the dorsal part of the dentate gyrus. The stimulating electrode was placed right above the hippocampal fissure to stimulate the perforant pathway fibers. Signals were filtered at 1 KHz and digitized at 10 KHz. Tetanic stimulation consisted of 2 trains of 100 pulses (0.4 ms pulse duration, 100 Hz) delivered with an inter-train interval of 5 seconds. The amplitude of population spike was measured from the initial phase of the negative wave. Up to five consecutive traces were averaged for each measurement. Synaptic transmission was assessed by generating input-output curves, with stimulus strength adjusted to be ~30% of the maximum. LTP was calculated as mean percentage change in the amplitude of the population spike following high frequency stimulation relative to its basal amplitude.

Contextual Fear Conditioning.

Paradigm follows previously published techniques (Alberini, C. M., Transcription factors in long-term memory and synaptic plasticity. Physiol. Rev. 89(1), 121-145 (2009)). Mice learned to associate the environmental context (fear conditioning chamber) with an aversive stimulus (mild foot shock; unconditioned stimulus, US) enabling testing for hippocampal-dependent contextual fear conditioning. The mild foot shock was paired with a light and tone cue (conditioned stimulus, CS) in order to also assess amygdala-dependent cued fear conditioning. Conditioned fear was displayed as freezing behavior. Specific training parameters are as follows: tone duration is 30 seconds; level is 70 dB, 2 kHz; shock duration is 2 seconds; intensity is 0.6 mA. On day 1 each mouse was placed in a fear-conditioning chamber and allowed to explore for 2 minutes before delivery of a 30-second tone (70 dB) ending with a 2-second foot shock (0.6 mA). Two minutes later, a second CS-US pair was delivered. On day 2 each mouse was first place in the fear-conditioning chamber containing the same exact context, but with no administration of a CS or foot shock. Freezing was analyzed for 1-3 minutes. One hour later, the mice were placed in a new context containing a different odor, cleaning solution, floor texture, chamber walls and shape. Animals were allowed to explore for 2 minutes before being re-exposed to the CS. Freezing was analyzed for 1-3 minutes. Freezing was measured using a FreezeScan video tracking system and software (Cleversys, Inc).

Radial Arm Water Maze.

Paradigm followed previously described protocol (Jones, M. W. et al. A requirement for the immediate early gene Zif268 in the expression of late LTP and long-term memories. Nat. Neurosci. 4(3), 289-296 (2001)). The goal arm location containing a platform remains constant throughout the training and testing phase, while the start arm is changed during each trial. On day one during the training phase, mice are trained for 15 trials, with trials alternating between a visible and hidden platform. On day two during the testing phase, mice are tested for 15 trials with a hidden platform. Entry into an incorrect arm is scored as an error, and errors are averaged over training blocks (three consecutive trials).

Plasma Collection.

Pooled mouse plasma was collected from 200-300 young (3-month-old) or old (18-month-old) mice by intracardial bleed at time of sacrifice. Plasma was prepared from blood collected with EDTA followed by centrifugation. Aliquots were stored at −80° C. until use. Prior to administration plasma was dialyzed in PBS through a 3.5 kDa molecular weight exclusion membrane to remove EDTA and proteins having an average molecular weight of 3.5 kD or less. Young adult mice were systemically treated with plasma (100

µl/injection) isolated from young or aged mice via intravenous injections into the tail vein 8 times over 24 days.

Data and Statistical Analysis.

Data are expressed as mean±SEM. Statistical analysis was performed with Prism 5.0 software (GraphPad Software). Means between two groups were compared with two-tailed, unpaired Student's t test. Comparisons of means from multiple groups with each other or against one control group were analyzed with 1-way ANOVA and Bonferroni post hoc tests. All histology, electrophysiology and behavior experiments conducted were done in a randomized and blinded fashion.

Results

In humans and mice, the hippocampus is a particularly vulnerable brain region to the effects of aging, exhibiting morphological alterations and reduced plasticity that result in impairments in spatial and episodic cognitive functions (Andrews-Hanna, J. R. et al. Disruption of large-scale brain systems in advanced aging. Neuron 56(5), 924-935 (2007); Scheff, S. W. et al. Synaptic alterations in CA1 in mild Alzheimer's disease and mild cognitive impairment. Neurology 68, 1501-1508 (2007); Nicholson, D. A. et al. Reduction in size of perforated postsynaptic densities in hippocampal axospinous synapses and age-related spatial learning. J. Neurosci. 24, 7648-7653 (2004); Smith, T. D. et al. Circuit-specific alterations in hippocampal synaptophysin immunoreactivity predict spatial learning impairments in aged rats. J. Neurosci. 20, 6587-6593 (2000); Geinisman, Y. et al. Loss of perforated synapses in the dentate gyrus: morphological substrate of memory deficits in age rats. Proc. Natl. Acad. Sci. USA 83, 3027-3031 (1986); Heeden, T. & Gabrieli, J. D., Insights into the ageing mind: a view from cognitive neuroscience. Nat. Rev. Neurosci. 5(2), 87-96 (2004); Morrison, J. H. & Baxter, M. G., The ageing cortical synapse: hallmarks and implications for cognitive decline. Nature Rev Neurosci 13(4), 240-250 (2012); Villeda, S. A. et al. The ageing systemic milieu negatively regulates neurogenesis and cognitive function. Nature 477(7362), 90-94 (2011); Raz, N. et al. Neuroanatomical correlates of cognitive aging: evidence from structural magnetic resonance imaging. Neuropsychology 12(1), 95-114 (1998); Mattson, M. P. & Magnus, T., Ageing and neuronal vulnerability. Nat. Rev. Neurosci. 7(4), 278-294 (2006); Rapp, P. R. & Heindel, W. C., Memory systems in normal and pathological aging. Curr. Opin. Neurol. 7(4), 294-298 (1994); Rosenzweig, E. S. & Barnes, C. A., Impact of aging on hippocampal function: plasticity, network dynamics, and cognition. Progress Neurobiol. 69(3), 143-179 (2003)). Therefore, we investigated potential benefits that exposure to young blood has within the aging hippocampus of mice at a molecular, structural, functional and cognitive level using a combination of heterochronic parabiosis (FIG. 1a) and blood plasma administration (FIG. 3a).

To gain broad insight into how systemic exposure to young blood affects the aging hippocampus, we performed a genome-wide microarray analysis of hippocampi from old isochronic (old-old) and heterochronic (old-young) parabionts (FIG. 1a). Unsupervised hierarchical clustering revealed a distinct gene expression profile between isochronic and heterochronic groups (FIG. 1 b). Using gene ontology (GO) classification of biological processes we identified a subset of genes differentially expressed in heterochronic parabionts categorized under synaptic plasticity regulation (FIG. 1c). Furthermore, Ingenuity Pathway Analysis (IPA) also detected a prominent involvement of plasticity related signaling pathways that include Egr1 (Alberini, C. M., Transcription factors in long-term memory and synaptic plasticity. Physiol. Rev. 89(1), 121-145 (2009); Jones, M. W. et al. A requirement for the immediate early gene Zif268 in the expression of late LTP and long-term memories. Nat. Neurosci. 4(3), 289-296 (2001)) and cyclic AMP response element binding (CREB) protein (Alberini, C. M., Transcription factors in long-term memory and synaptic plasticity. Physiol. Rev. 89(1), 121-145 (2009); Guzowski, J. F. et al. Experience-dependent gene expression in the rat hippocampus after spatial learning: a comparison of the immediate-early genes Arc, c-fos, and zif268. J. Neurosci. 21(14), 5089-5098 (2001); Sanciu, M., et al. Phosphorylated cAMP response element binding protein in the mouse brain after fear conditioning: relationship to Fos production. Brain Res. Mol. Brain Res. 94(1-2), 15-24 (2001)) as part of the top signaling network in heterochronic parabionts (FIG. 1d). Together, our microarray analysis points to the existence of a transcriptional profile indicative of enhanced plasticity in the hippocampus of heterochronic parabionts.

Figure 4:
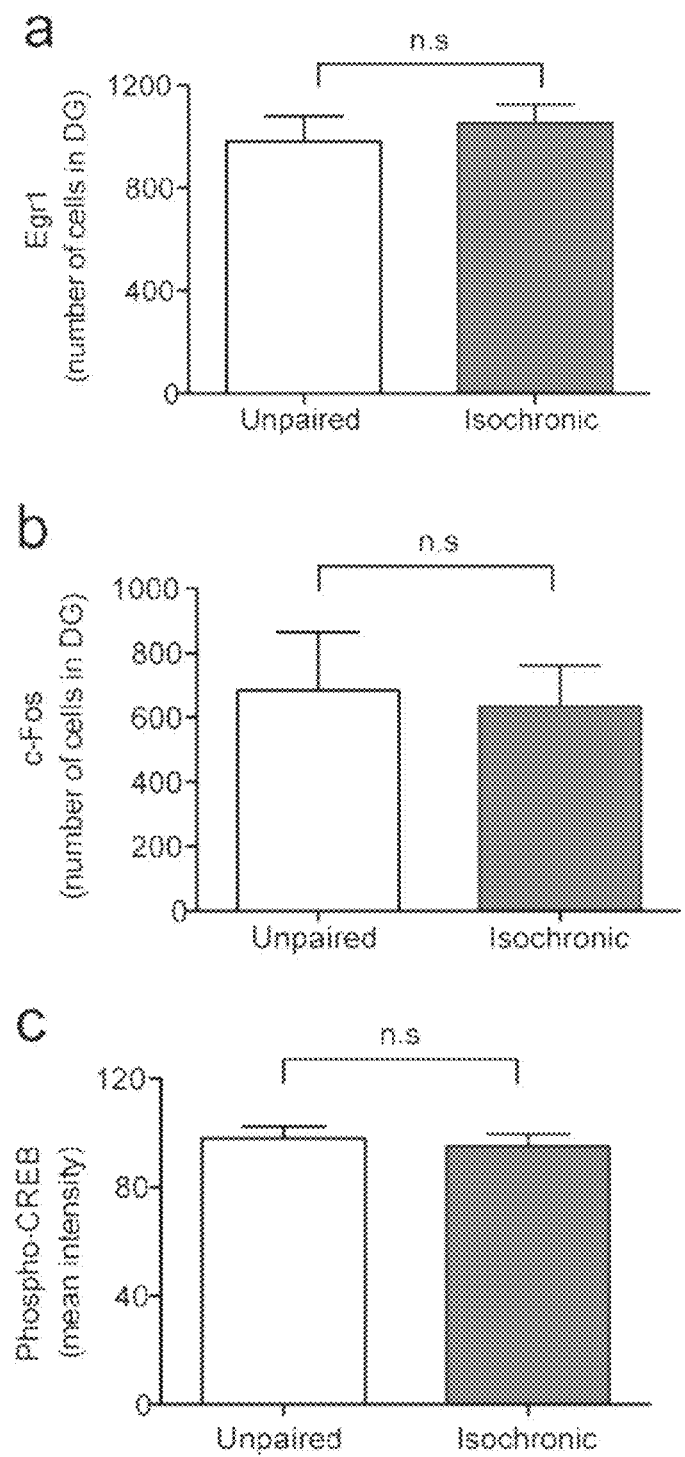
FIG. 4, Panels a-c. Isochronic parabiosis does not alter expression of synaptic plasticity markers. Histological analysis of synaptic plasticity markers was done on the DG of the hippocampus of old (18-month-old) isochronic parabionts and unpaired age-matched controls. N=5-6 mice per group. Panels a-c, Quantification of immunostaining for Egr1 (Panel a), c-Fos (Panel b) and phosphorylated CREB (Panel c). 5 sections per mouse were analyzed. Bars are mean+SEM; n.s., not significant; t-test.

To further investigate molecular changes involved in synaptic plasticity, and corroborate our microarray analysis, we examined the activation of a subset of the identified factors from our microarray analysis. Specifically, we examined the protein expression of the activity dependent immediate early genes Egr1 and c-Fos, as well as CREB phosphorylation, by immunohistochemistry in the dentate gyrus (DG) of the hippocampus of old parabionts (FIG. 2a-d). We observed an increase in the number of cells expressing Egr1 (FIG. 2a,b) and c-Fos (FIG. 2a,c), and a corresponding increase in the levels of phosphorylated CREB (FIG. 2a,d) in heterochronic as compared to isochronic parabionts. As previously reported, peripherally derived cells were rarely detected in the brain of parabionts (Villeda, S. A. et al. The ageing systemic milieu negatively regulates neurogenesis and cognitive function. Nature 477(7362), 90-94 (2011); Ajami, B. et al., Local self-renewal can sustain CNS microglia maintenance and function throughout adult life. Nat Neuro 10(12), 1538-1543 (2007) and molecular changes were not elicited by the parabiosis surgical procedure itself (FIG. 4). These data indicate that synaptic plasticity in the hippocampus of old animals may be enhanced by systemic exposure to young blood.

Figure 2:
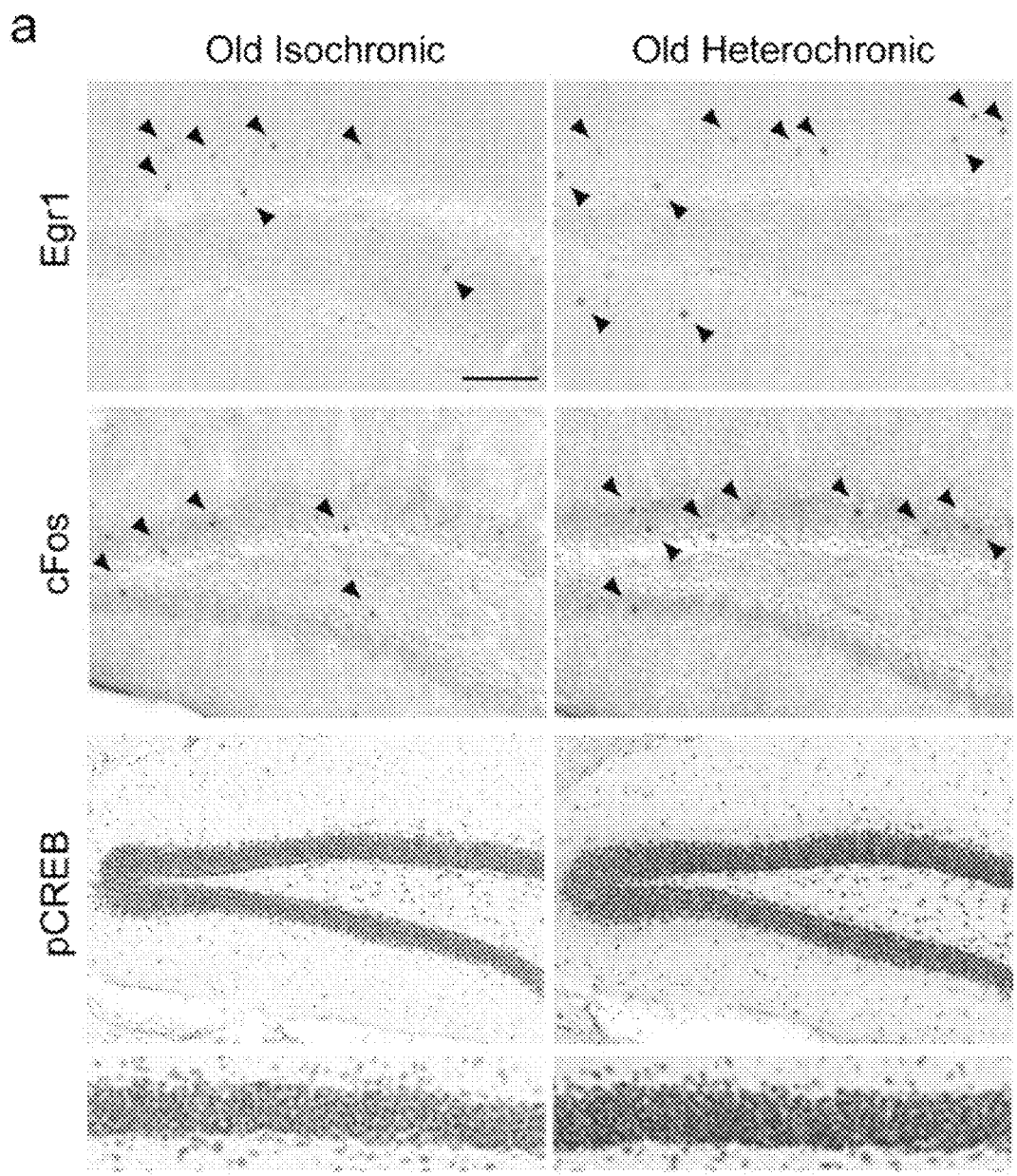
FIG. 2, Panels a-g. Heterochronic parabiosis enhances synapse formation and synaptic plasticity in the old brain. Panels a-g, Histological and electrophysiological analysis was done on old (18-month-old) isochronic and heterochronic parabionts analyzed 5 weeks post surgery. N=5-6 mice per group. Panel a, Immunohistochemical detection of Egr1, cFos, and phosphorylated cyclic AMP response element binding (CREB) protein in the DG of the hippocampus of old isochronic and heterochronic parabionts. Arrowheads depict individual cells. (scale bar: 100 μm). Panels b-d, Quantification of immunostaining for Egr1 (Panel b), c-Fos (Panel c) and phosphorylated CREB (Panel d). 5 sections per mouse were analyzed. Panels e,f, Representative Golgi stain image (Panel e) and quantification of dendritic spine density on tertiary branches (Panel f). 5 neurons per mouse were analyzed. Panel g, Population spike amplitude (PSA) was recorded from DG of old parabionts. Representative long-term potentiation (LTP) levels are shown for isochronic and heterochronic parabionts. Data represented as Mean±SEM; *$P<0.05$; **$P<0.01$; t-test (Panels b-d).
Figure 2:
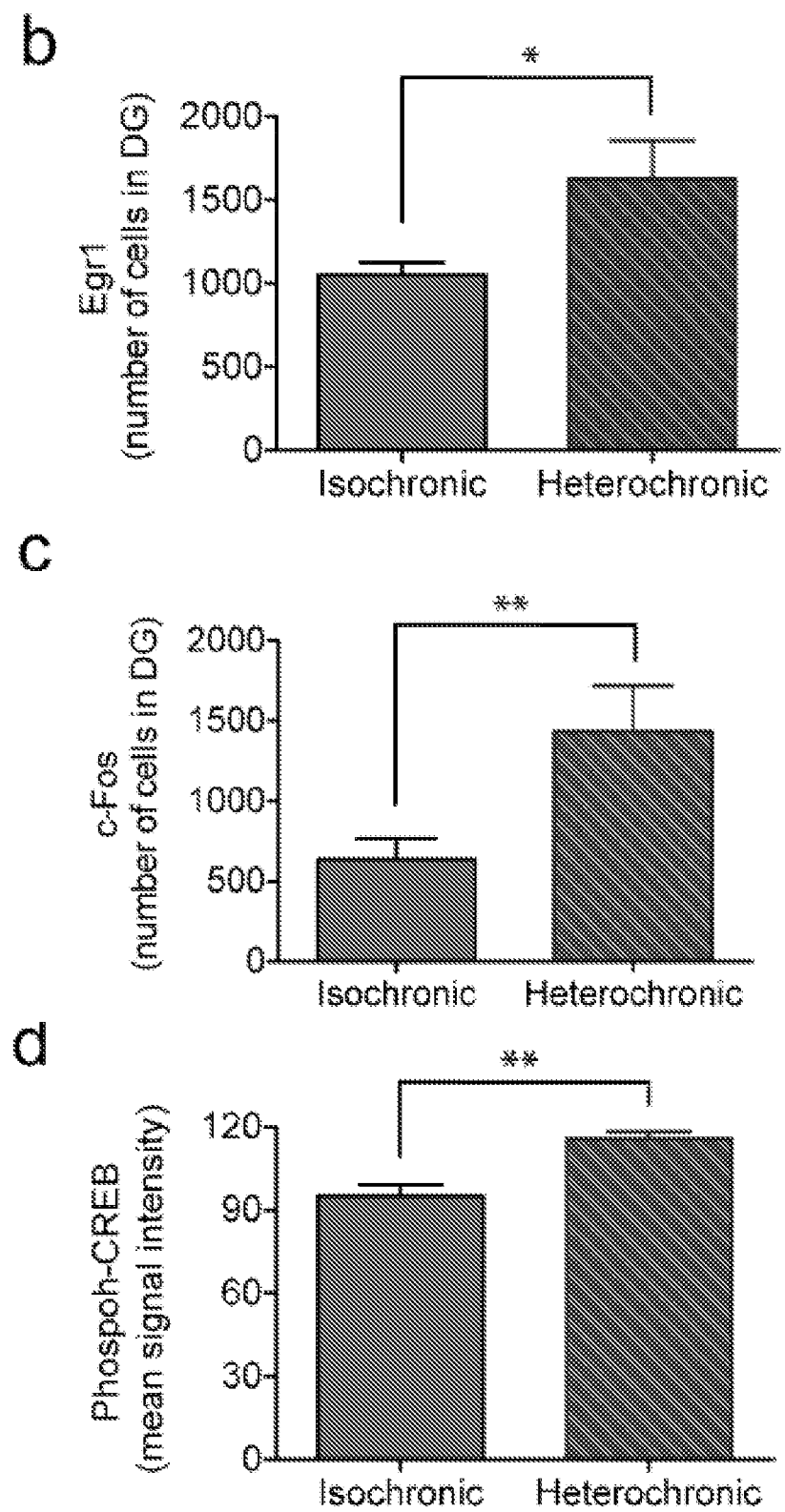
Figure 2:
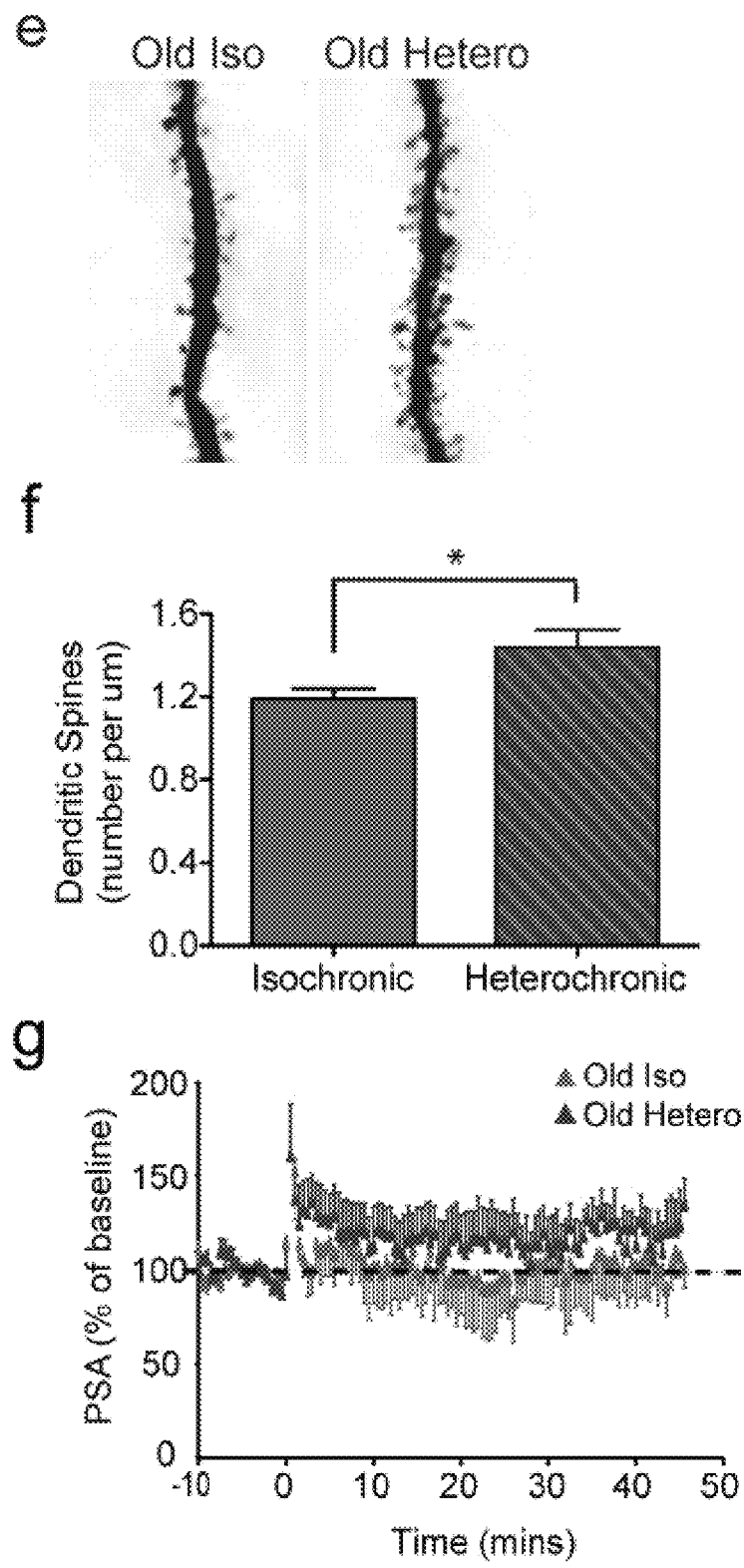
Figure 5:
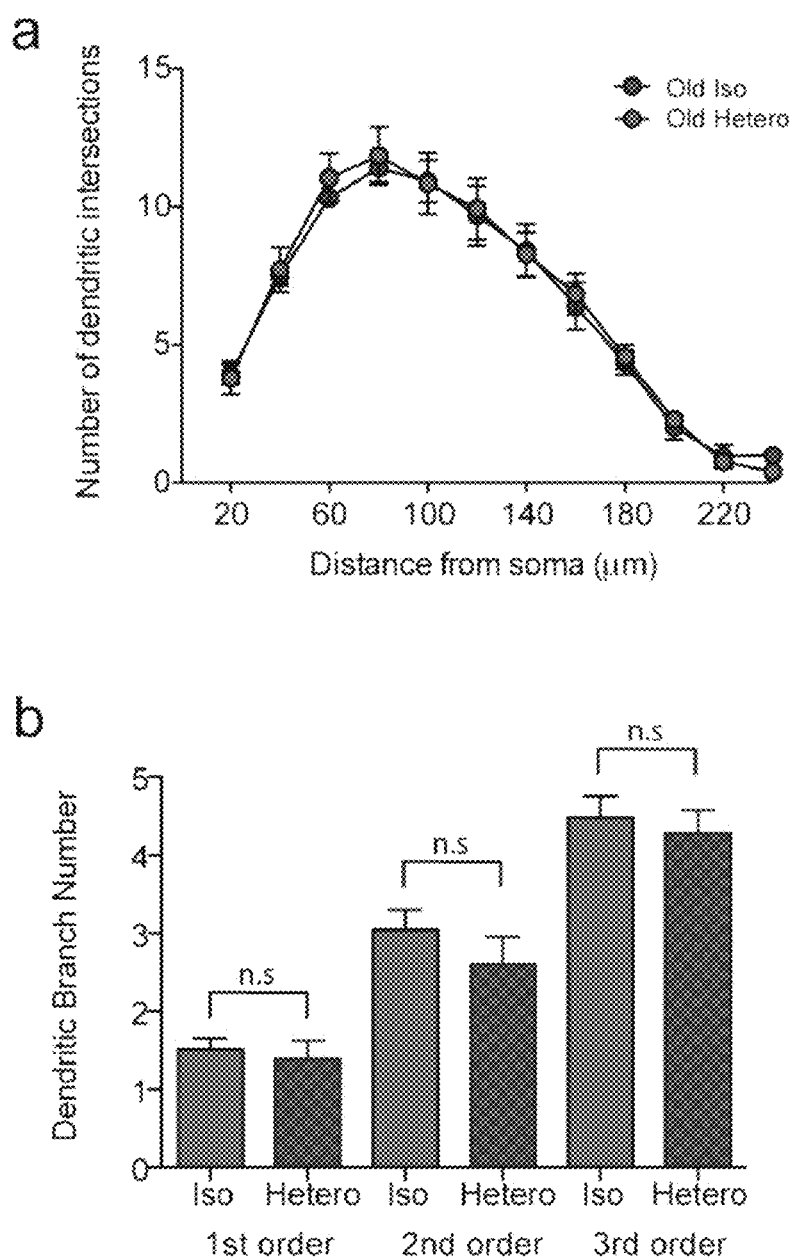
FIG. 5, Panels a-d. Heterochronic parabiosis does not alter dendritic complexity or basal synaptic transmission. Panels a-c, Golgi analysis was done using Neurolucida Software (v10, MBF Bioscience) on 5 neurons per mouse (18-month-old) for a total of 25 neurons. N=5 per group. Panel a, Sholl analysis was graphed as the average intersections per shell per neuron against the distance from the soma. Panels b,c, Neuron tracings were used to quantify the average number of primary, secondary and tertiary dendritic branches (Panel b) and total dendrite length (Panel c). Panel d, input-output curves indicate no statistical difference in synaptic strength, a key parameter of basal synaptic transmission, between old isochronic and heterochronic parabionts. Bars are mean+SEM; n.s., not significant; t-test.
Figure 5:
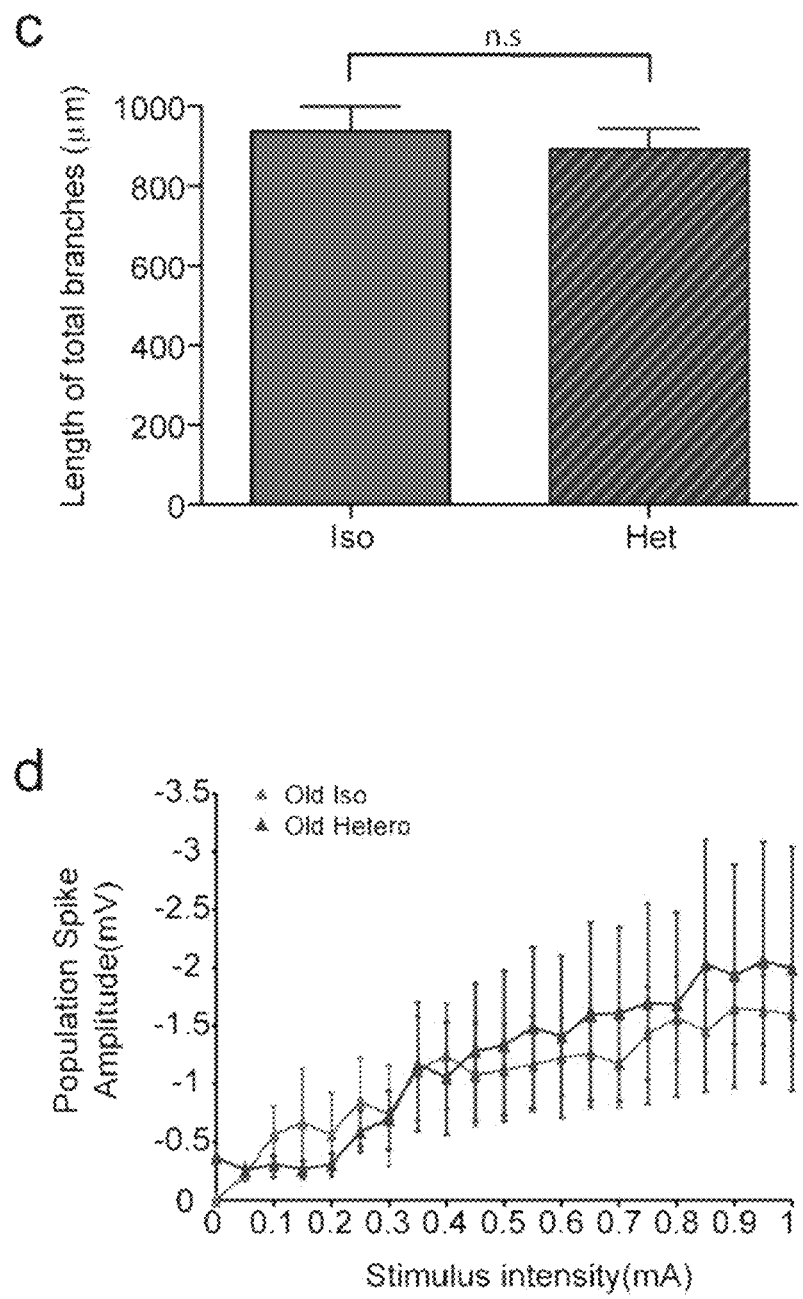

Having identified molecular changes involved in synaptic plasticity, we next characterized structural changes underlying synapse formation in old parabionts. Using Golgi analysis, we examined pre-existing mature neurons in the DG of the hippocampus for changes in spine formation and dendritic arborization. Interestingly, we observed that the density of dendritic spines along individual dendrites of hippocampal granule cell neurons was increased in heterochronic compared to isochronic parabionts (FIG. 2e,f). However, no differences in dendritic complexity (FIG. 5a), dendrite branch number (FIG. 5b) or dendrite branch length (FIG. 5c) were observed between heterochronic and isochronic groups. Together, these structural data indicate that exposure of an old animal to young blood selectively enhances synapse formation within the aging hippocampus. To investigate whether functional enhancements in the old brain could also be elicited by exposure to young blood, we performed extracellular electrophysiological recordings on hippocampal slices prepared from old parabionts (FIG. 2g). While long-term potentiation (LTP) in the DG of isochronic parabionts quickly reached baseline level, LTP in heterochronic parabionts was maintained above baseline throughout the recording period (FIG. 2g). No differences in synaptic strength were observed between groups (FIG. 5d).

These functional data indicate that synaptic plasticity in the hippocampus of old animals is enhanced by exposure to young blood.

Figure 3:
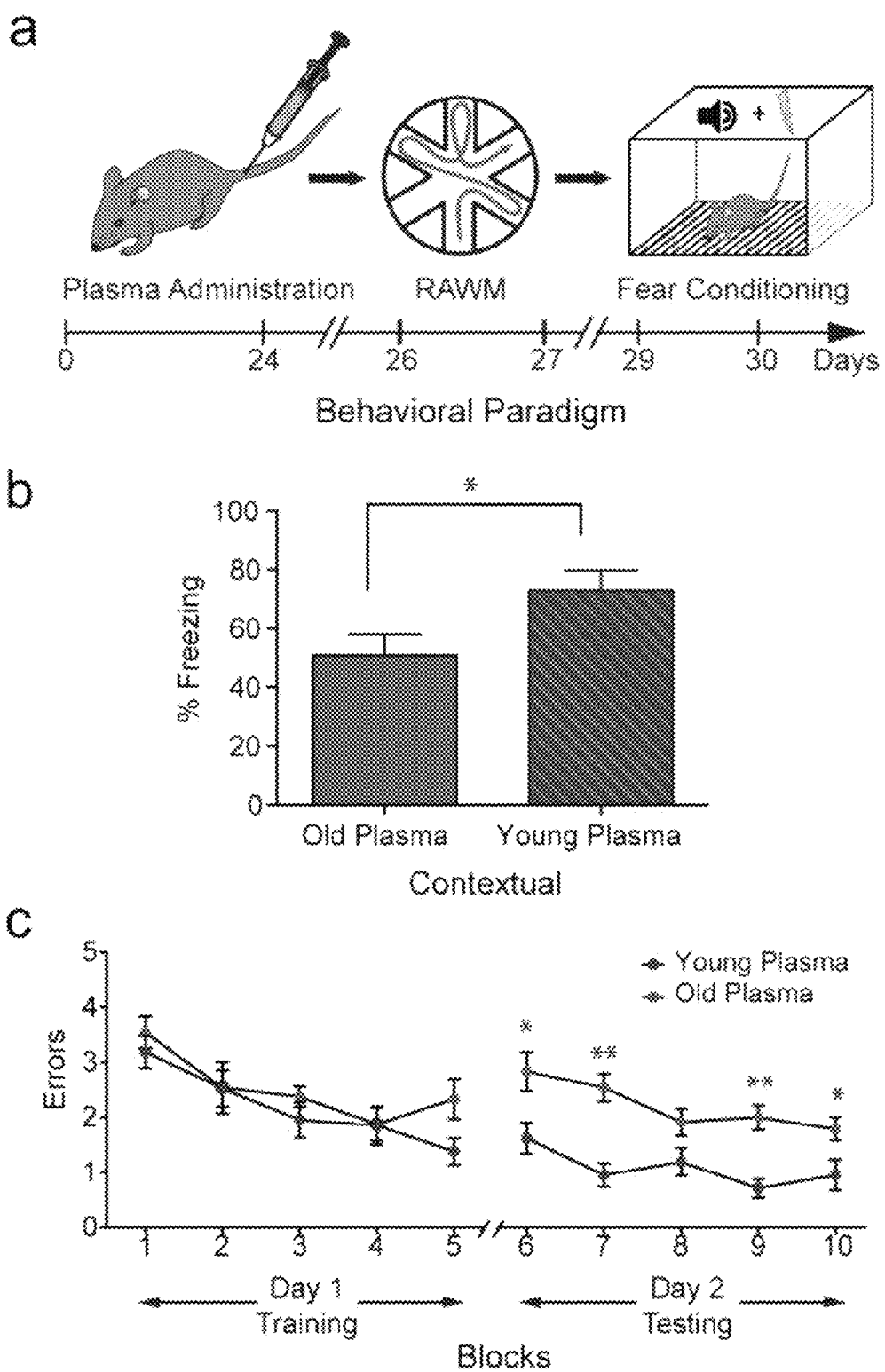
FIG. 3, Panels a-c. Young blood administration improves hippocampal dependent learning and memory in old mice. Panels a-c. Old (18-month-old) mice were cognitively tested after treatment with young (3-month-old) or old (18-month-old) plasma 8 times over 24 days (100 µl/intravenous injection). N=8 mice per group. Panel a, Schematic illustrating the chronological order used for plasma treatment and cognitive testing. Panels b,c, Hippocampal learning and memory was assessed by contextual fear conditioning (Panel b) and radial arm water maze (RAWM) (Panel c) following plasma treatment. Panel b, Percent freezing time 24 hours after training. Panel c, Number of entry arm errors prior to finding platform. Data represented as Mean±SEM; *P<0.05; **P<0.01; t-test (Panel b), ANOVA, Bonferroni post-hoc test (Panel c).
Figure 6:
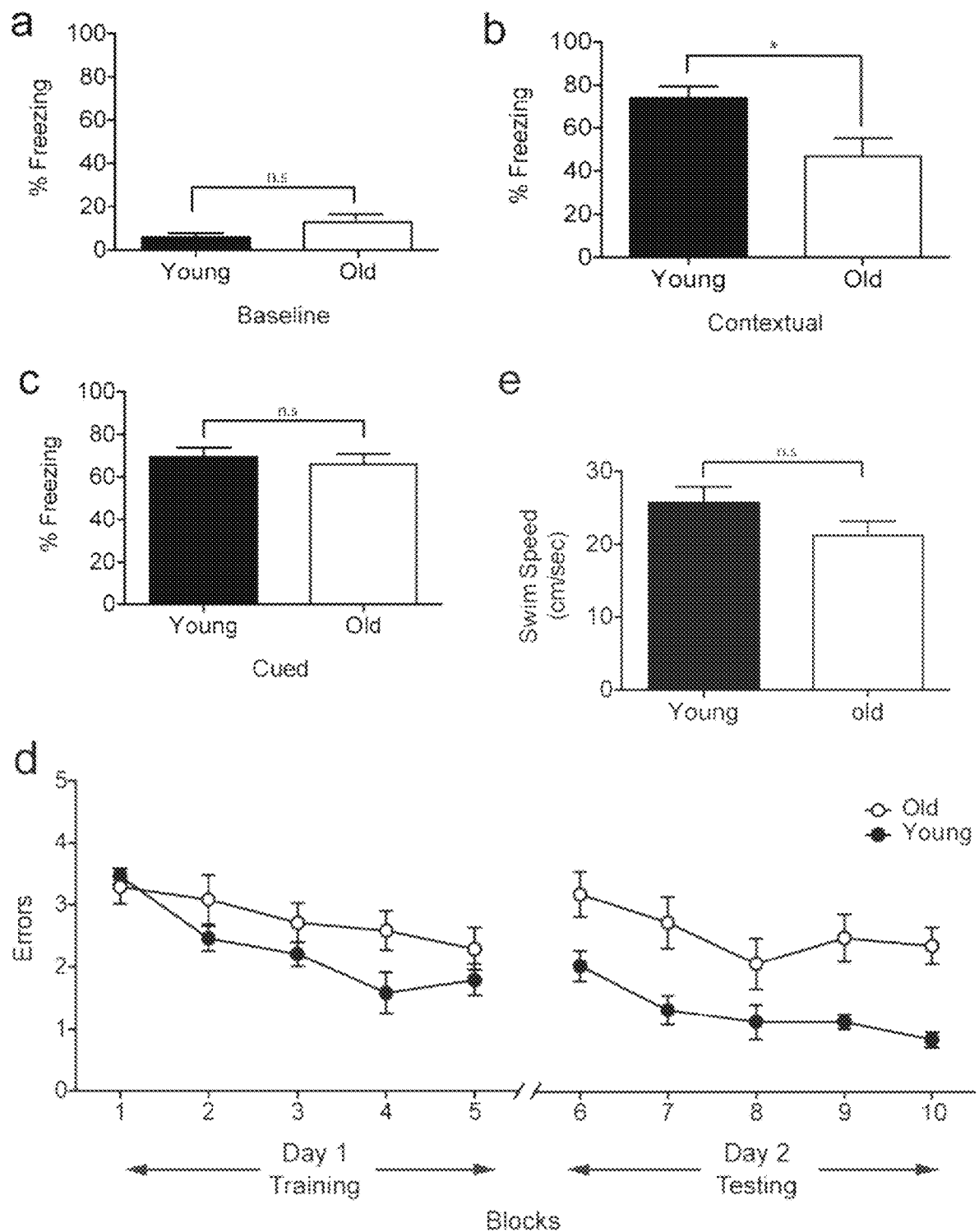
FIG. 6, Panels a-e. Hippocampal dependent learning and memory is impaired in old mice. Panels a-e, Learning and memory was examined during normal aging in young (3-month-old) versus old (18-month-old) adult animals using contextual fear conditioning (Panels a-c) and RAWM (Panels d-e) paradigms. Panel a, Young and old animals exhibited similar baseline freezing time during fear conditioning training. Panel b, During contextual fear conditioning old mice demonstrate decreased freezing time during contextual memory testing. Panel c, No differences in cued memory were detected 24 hours after training. Panel e, Old mice demonstrate impaired learning and memory for platform location during the testing phase of the RAWM task. Cognitive deficits were quantified as the number of entry arm errors made prior to finding the target platform. No differences in swim speeds were detected between young and old animals. Data are from 8 animals per group. Bars are mean+SEM; n.s., not significant; t-test.
Figure 7:
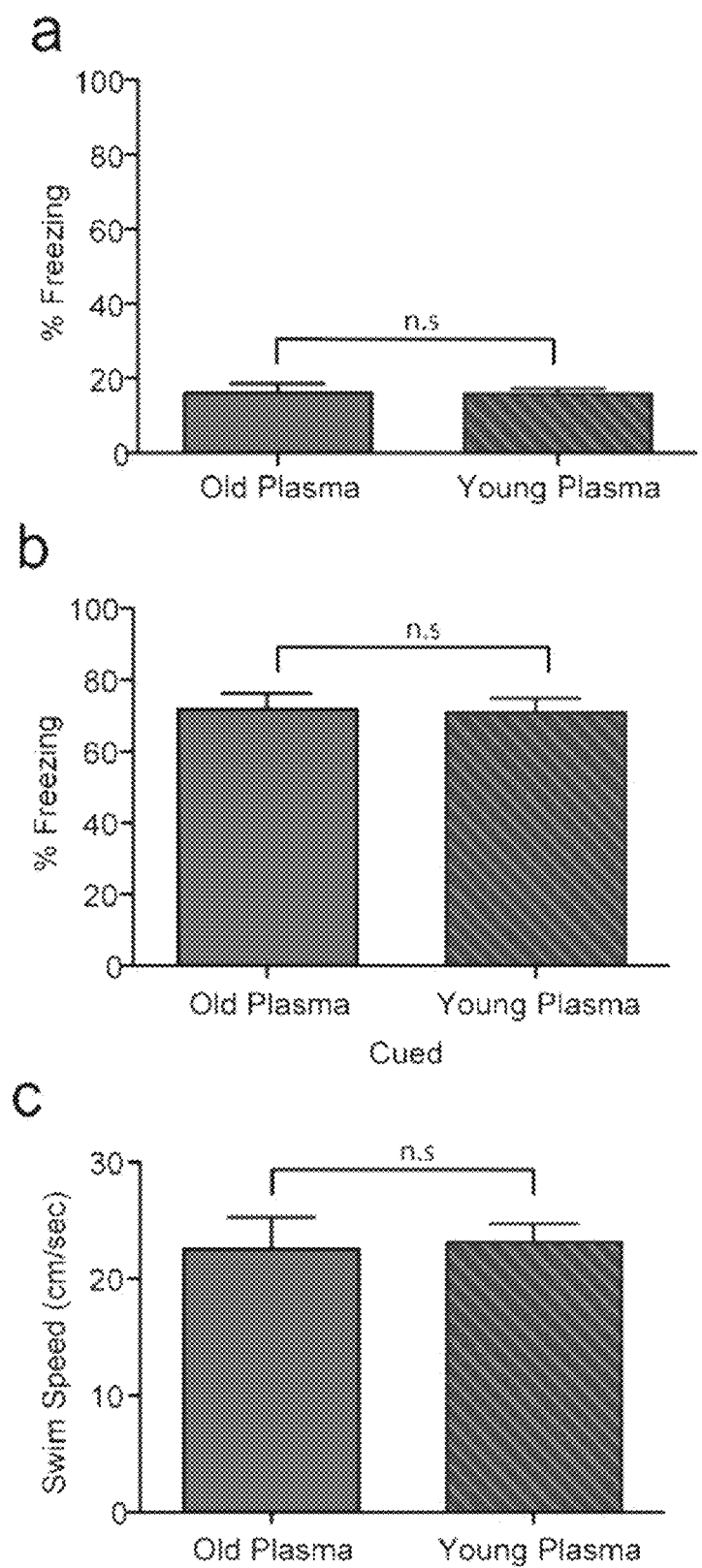
FIG. 7, Panels a-c. Exposure to young blood does not affect cued memory or swim speed. Panels a-c, Old adult male mice (18-month-old) were injected intravenously with plasma (100 µl/injection) derived from young (3-month-old) or old (age 18-month-old) animals 8 times over 24 days. Panel a, Animals intravenously injected with young or old plasma exhibited similar baseline freezing time during training. Panel b, No differences in cued memory were detected between groups when re-exposed to the conditioned stimulus (tone and light) in a novel context 24 hours after training. Panel c, Swim speeds of old and young plasma treated mice during the training phase of the RAWM. Data are from 8 animals per group. Bars are mean+SEM; n.s., not significant; t-test.

Considering that learning and memory is mediated at a cellular level by synapse formation (Rosenzweig, E. S. & Barnes, C. A., Impact of aging on hippocampal function: plasticity, network dynamics, and cognition. Progress Neurobiol. 69(3), 143-179 (2003); Bliss, T. V. & Collingridge, G. L., A synaptic model of memory: long-term potentiation in the hippocampus. Nature 361(6407), 31-39 (1993); Martin, S. J., Grimwood, P. D. & Morris, R. G. Synaptic plasticity and memory: an evaluation of the hypothesis. Annu. Rev. Neurosci. 23, 649-711 (2000)) with LTP serving as a putative functional correlate (Bliss, T. V. & Collingridge, G. L., A synaptic model of memory: long-term potentiation in the hippocampus. Nature 361(6407), 31-39 (1993); Martin, S. J., Grimwood, P. D. & Morris, R. G. Synaptic plasticity and memory: an evaluation of the hypothesis. Annu. Rev. Neurosci. 23, 649-711 (2000)), it is exciting to postulate that the structural and functional enhancements observed after the exposure to young blood may accompany improvements in higher order cognitive processes. In particular, the hippocampus is of fundamental importance in the acquisition and retention of new memories. However these processes are greatly susceptible to impairment by the influence of aging (Villeda, S. A. et al. The ageing systemic milieu negatively regulates neurogenesis and cognitive function. Nature 477(7362), 90-94 (2011); Rapp, P. R. & Heindel, W. C., Memory systems in normal and pathological aging. Curr. Opin. Neurol. 7(4), 294-298 (1994)). Therefore, to determine whether exposure to young blood could in fact improve impairments in hippocampal-dependent learning and memory in old mice, we used contextual fear conditioning and radial arm water maze (RAWM) paradigms (FIG. 3). As a control, we first tested a cohort of young and old untreated animals and observed age-related cognitive impairments with both behavioral paradigms (FIG. 6). Subsequently, an independent cohort of old adult mice was intravenously injected with young or old plasma a total of eight times over three weeks prior to cognitive testing (FIG. 3a). During fear conditioning training, all mice exhibited similar baseline freezing regardless of treatment (FIG. 7a). However, old mice receiving young plasma demonstrated increased freezing in contextual (FIG. 3b), but not cued (FIG. 7b) memory testing. Additionally, in the training phase of the RAWM paradigm all mice showed similar spatial learning capacity (FIG. 3c) and swim speeds (FIG. 7c). Excitingly, old animals administered with young plasma demonstrated enhanced learning and memory for platform location during the testing phase of the task (FIG. 3c), consistent with our contextual fear conditioning data (FIG. 3b). Importantly, no cognitive differences in either fear conditioning or the RAWM were detected between untreated and old plasma treated animals (FIG. 8), substantiating the importance of young derived blood. Together, these behavioral data indicate that administration of young blood—even late in life—is capable of eliciting cognitive improvements in hippocampal-dependent learning and memory in old animals.

Cumulatively, our data demonstrate that exposure to young blood cannot only increase the regenerative capacity of the aging nervous system, but furthermore, can even counteract the pre-existing effects of aging itself at a structural, functional and cognitive level. Interestingly, current data are not consistent with respect to a causal link between decreased neurogenesis and age-related cognitive decline (Morrison, J. H. & Baxter, M. G., The ageing cortical synapse: hallmarks and implications for cognitive decline. Nature Rev Neurosci 13(4), 240-250 (2012); Merrill, D. A. et al. Hippocampal cell genesis does not correlate with spatial learning ability in age rats. J. Comp. Neurol. 459, 201-207 (2003); Bizon, J. L. & Gallagher, M. Production of new cells in the rat dentate gyrus over the lifespan: relation to cognitive decline. Eur. J. Neuorsci. 18, 215-219 (2003); Drapeau, E. et al. Spatial memory performances of aged rats in the water maze predict levels of hippocampal neurogenesis. Proc. Natl. Acad. Sci. USA 100, 14385-14390 (2003); Leuner, B. et al. Diminished adult neurogenesis in the marmoset brain precedes old age. Proc. Natl. Acad. Sci. USA 104, 17169-17173 (2007); Luo, J. et al., Glia-dependent TGF-beta signaling, acting independently of the TH17 pathway, is critical for initiation of murine autoimmune encephalomyelitis. J Clin Invest 117 (11), 3306-3315 (2007)). As a result, this suggests that the cognitive improvements observed in our study after exposure to young blood are not predominantly due to changes in regenerative capacity, but rather the result of enhancements in plasticity.

Ultimately, our findings show the feasibility of utilizing young blood towards therapeutic interventions aimed at reversing cognitive impairments in the elderly by harnessing the latent plasticity remaining within the old brain. Importantly, these studies indicate the beneficial effects of administering young blood may extend beyond normal aging towards reversing cellular and cognitive decline in those suffering from age-related neurodegenerative disorders such as AD.

Example 2

Figure 9:
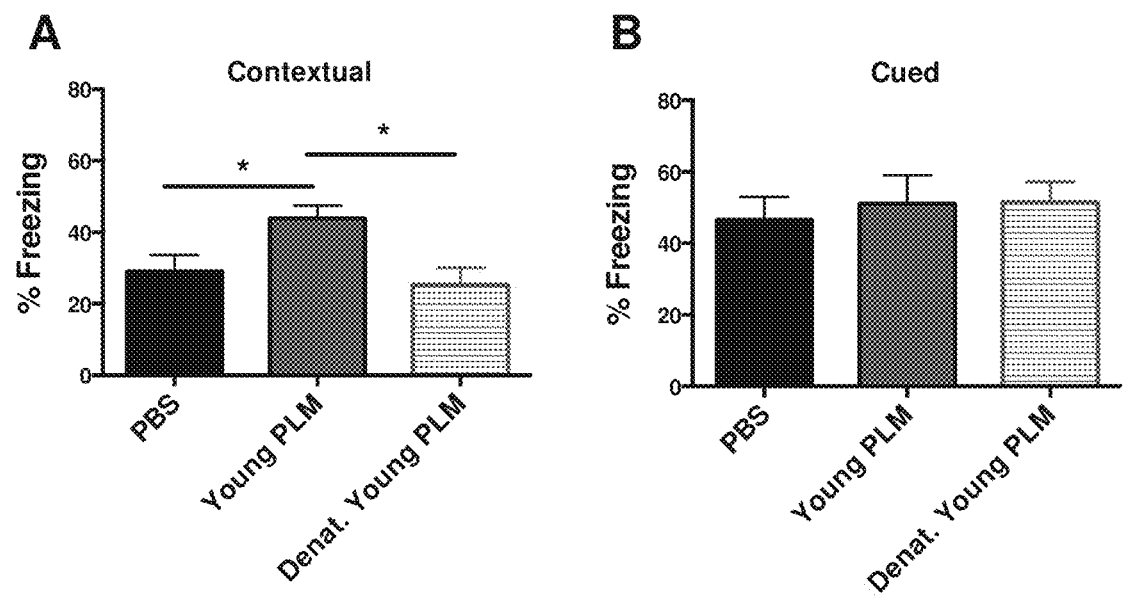
FIG. 9, Panels A-B. Denaturing young plasma abolishes positive cognitive effects of plasma treatment in old mice. Panel A. Percentage freezing observed in old mice treated with PBS, young plasma, or young denatured plasma during the first minute of exposure to the same context as the training environment (n=10-12/group). Panel B. Percentage freezing for old mice treated with PBS, young plasma, or denatured young plasma during the cued task in which mice are exposed to a new context but given the tone and light cues from training (n=10-12/group). Bars represent mean+/−SEM. Groups were compared by 1-way ANOVA followed by Tukey's post hoc test for multiple comparisons (*P<0.05).

To assess the necessity of soluble factors present in young plasma in mediating rejuvenating effects on cognition, we treated old mice (18 mos.) by tail vein injection with young plasma or heat-denatured plasma. PBS was injected as a control to assess the possibility that dilution of negative factors present in the circulation could underlie cognitive improvement. Plasma was collected from young (8 weeks) C57BI/6J mice and pooled prior to dialysis with a 3.5 kDa molecular weight exclusion membrane. A portion of plasma was heat-denatured by 2-3 minutes of denaturation at 95° C. Mice were injected 8 times over several weeks and exposed to a fear conditioning paradigm to assess hippocampal-dependent memory. Following the first day of training in which mice were given a mild foot shock paired with a light and tone, mice were exposed to the same context and freezing behavior was assessed. The cage environment was then changed and freezing behavior was measured to assess memory that was not hippocampal-dependent (cued). As demonstrated in FIG. 9, denaturation of young plasma abolished the positive effects of young plasma on the cognitive abilities of old mice (FIG. 9)

Example 3

Figure 8:
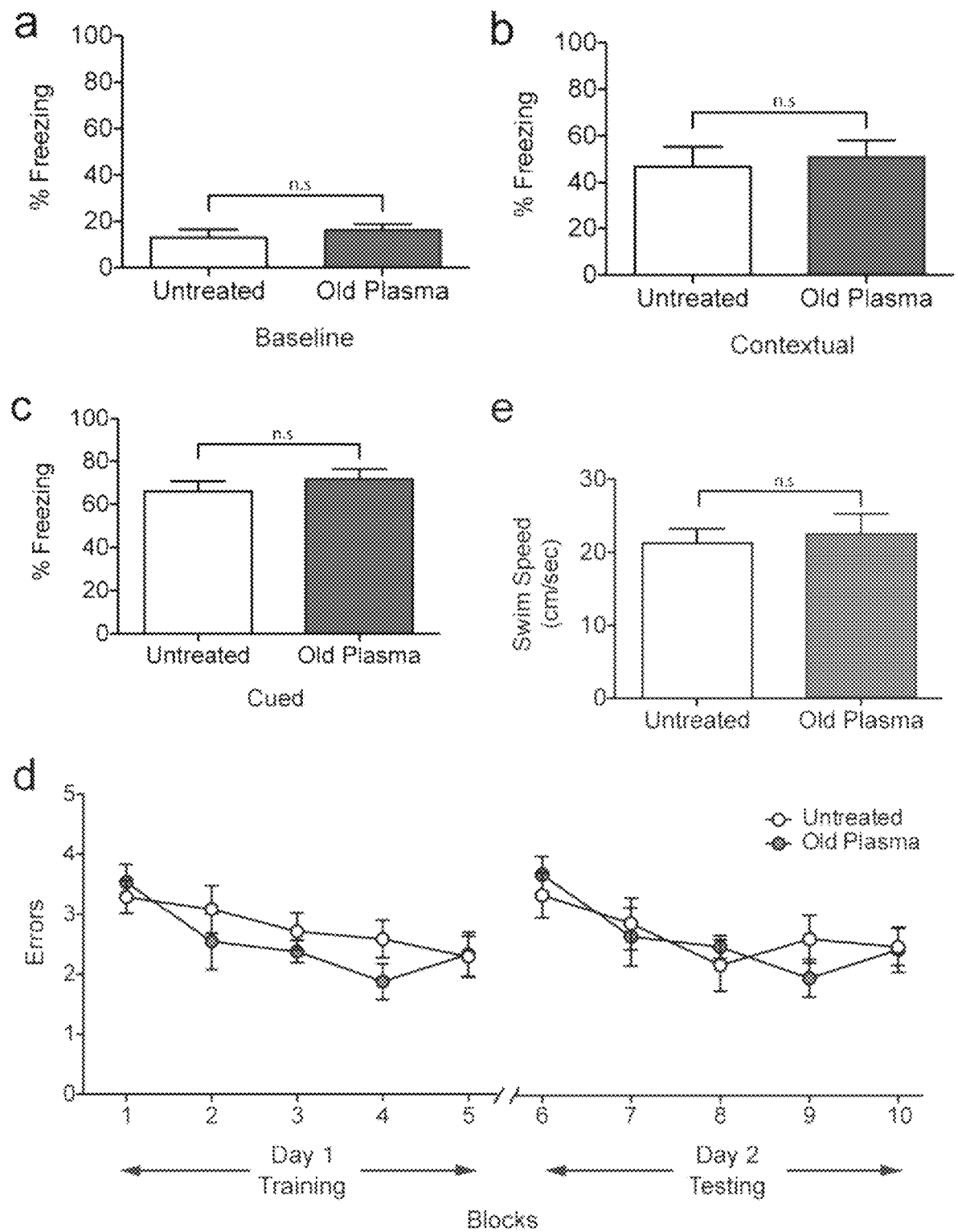
FIG. 8, Panels a-e. Hippocampal dependent learning and memory is not altered by exposure to old blood. Panels a-e, Learning and memory was examined in untreated old adult mice (18-month-old) using fear conditioning and RAWM paradigms and compared to old animals injected intravenously with plasma (100 µl/injection) derived from old (18-month-old) animals 8 times over 24 days. N=8 per group. No differences in baseline freezing were detected during fear conditioning training (Panel a), and no differences in freezing were detected during contextual (Panel b) or cued (Panel c) fear conditioning testing. Panel d, No differences in spatial learning and memory were detected in the RAWM paradigm. Panel e, No differences in swim speeds were observed between animals receiving old plasma and untreated controls. Bars are mean+SEM; n.s., not significant; t-test.
Figure 10:
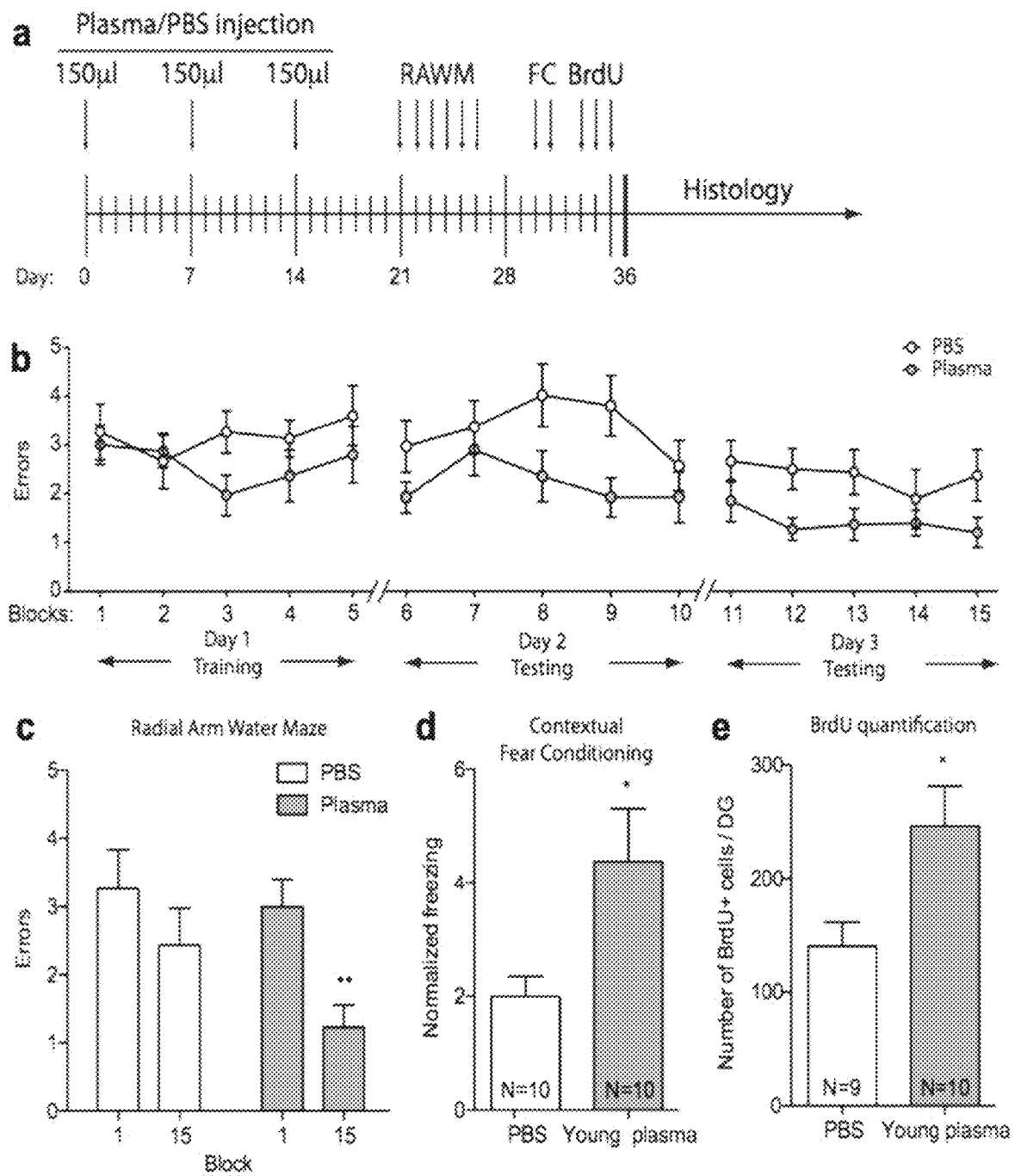
FIG. 10, Panels a-e. Three weekly administrations of young blood improve hippocampal dependent learning and memory and neurogenesis in old mice. Panel a, Schematic illustrating the chronological order used for plasma treatment, cognitive testing and histological analysis. Three 150 µl injections of young plasma (2-3 mo old) or PBS were given i.v., one per week (day 0, 7, 14). After the third injection, a 3-day Radial Arm Water Maze (RAWM) task was performed, one group (mixed treatment) starting at day 21, another group starting at day 24. A fear-conditioning test (FC) was performed on day 30 (training) and day 31 (testing). All mice were injected daily with BrdU (50 mg/kg) i.p. 3 days prior to sacrifice, after which neurogenesis in assessed. Panel b, Number of entry arm errors prior to finding platform on the training day (day 1) and testing days (day 2 and 3). The plasma treated group performed consistently better on days 2 and 3 than the PBS treated group. One block represents 3 trials. Panel c, Quantification of learning in the RAWM showing the number of errors made on day 1, block 1 vs. day 3, block 15. The young plasma-treated group made significantly fewer errors in block 15 vs. block 1. Panel d, Normalized freezing behavior in the contextual fear-conditioning test shows significantly more freezing in the young plasma-treated group compared to the PBS-treated group, consistent with improved memory for the task. Panel e, Mice treated with young plasma show a significantly larger number of BrdU-positive cells in the dentate gyrus (DG) of the hippocampus compared to the PBS-treated group. Data represented as Mean±SEM; *P<0.05; **P<0.01; ANOVA, Bonferroni post-hoc test (Panel b), t-test (Panels c-e).

To optimize the delivery of young plasma, an experiment was conducted in which plasma from 2-month-old mice was administered to 18-month-old mice only once a week (150 µl/injection) for three weeks before cognitive testing and histological analysis (FIG. 8). These studies were conducted completely blinded. As illustrated in FIG. 10, we observed increased freezing in the contextual fear conditioning paradigm, better RAWM performance, and twice as many BrdU+ neurons in mice treated with young plasma compared with age-matched saline treated controls.

Example 4

It is shown here that exposure of a mouse that models Alzheimer's disease to a young healthy circulatory environment reduces the neuropathology known to be associated with these models and known to similarly occur in human patients with the disease.

Transgenic mouse models overproducing human amyloid precursor protein (APP) containing mutations found in families with autosomal dominant Alzheimer's disease reproduce important aspects of the disease, including amyloid plaques, neurodegeneration, and behavioral deficits. Transgenic mice which overexpress human APP751$^{V717I, K670M/N671L}$ (aka London and Swedish mutations) in neurons under control of a Thy1.2 promoter, specifically Line 41 generated by the Masliah lab (Rockenstein, E. et al. Early Formation of Mature Amyloid-β Protein Deposits in a Mutant APP Transgenic Model Depends on Levels of Aβ 1-42. Journal of Neuroscience Research 66:573-582 (2001)), develop amyloid pathology, neurodegeneration, and cognitive deficits (Rockenstein et al., supra). These mice (hAPP$^{L/S}$) have been studied by multiple independent academic laboratories (Pickford et al. The autophagy-related protein beclin 1 shows reduced expression in early Alzheimer disease and regulates amyloid β accumulation in mice. J. Clin. Invest (2008); Faizi et al. Thy1-hAPPLond/Swe+ mouse model of Alzheimer's disease displays broad behavioral deficits in sensorimotor, cognitive and social function. 2012. Wiley Periodicals, Inc. Brain and Behavior; Knowles et al. The p75 Neurotrophin Receptor Promotes Amyloid-13(1-42)-Induced Neuritic Dystrophy in Vitro and in Vivo The Journal of Neuroscience, August 26, 29 (34):10627-10637 (2009)) and have been used as a model for drug development.

Figure 11:
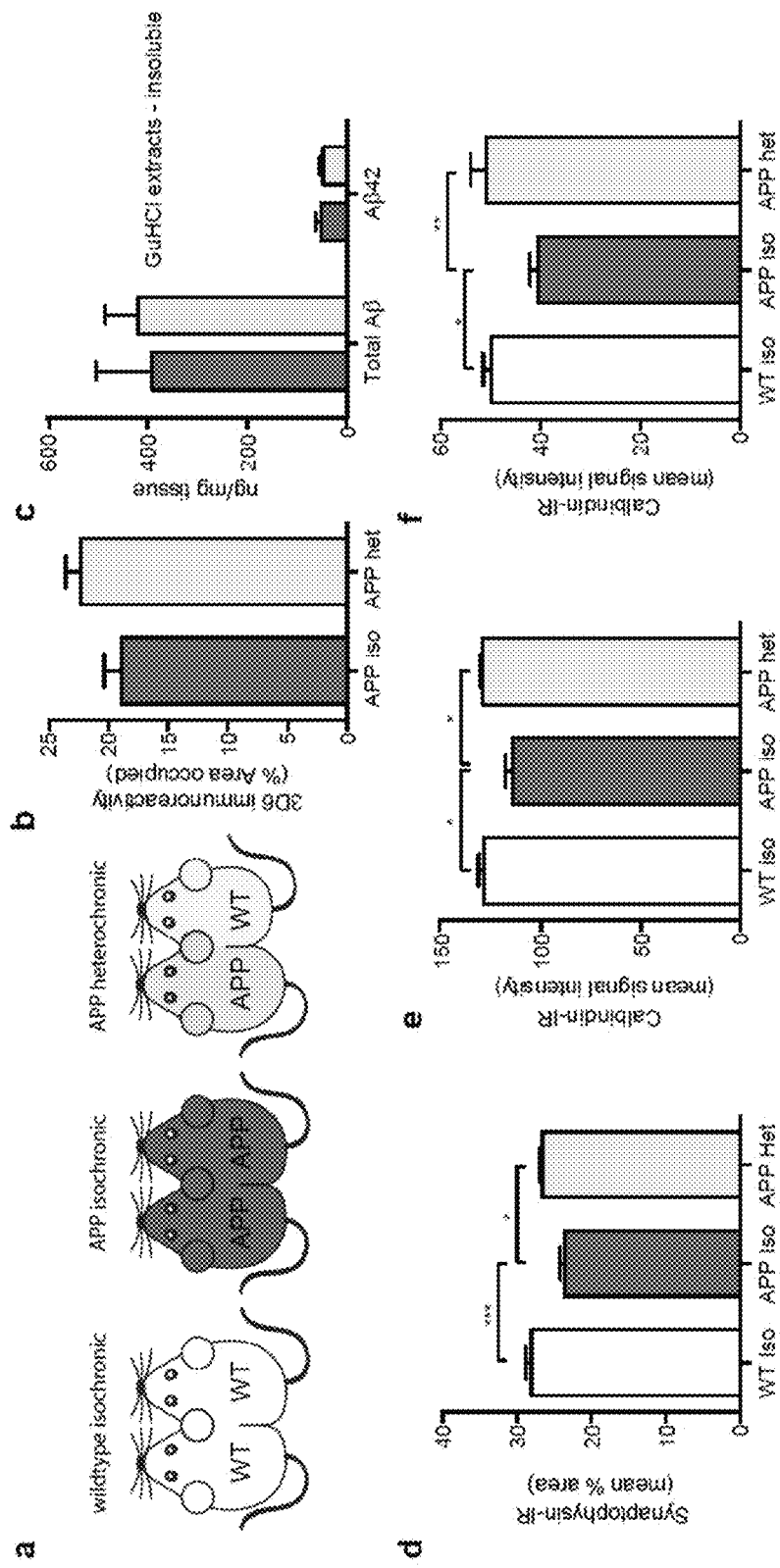
FIG. 11, Panels a-f. (Panel a) Schematic depicting the three different types of parabiosis between mice: wildtype isochronic (WT iso), APP isochronic (APP iso) and APP heterochronic (APP het). Isochronic pairs are age-matched and the same age as the APP mouse from the heterochronic pair, which is connected to a young (2-3 month old) wildtype mouse. One cohort consisted of old (16-20 month) male mice and another of middle-aged (10-12 month) female mice. All pairs were surgically connected for 5 weeks. (Panel b) Quantification of immunohistochemical detection of amyloid plaques (3D6 staining) in the hippocampus of old APP iso (n=6) and APP het (n=4) mice. (Panel c) ELISA measurements of insoluble total Aβ and Aβ42 levels in the hippocampus of old male APP iso (n=6) and APP het (n=4) mice. (Panels d-e) Quantification of synaptophysin-immunoreactivity (Panel d) and calbindin-immunoreactivity (Panel e) in the molecular layer of the dentate gyrus of old male parabionts; WT iso (n=6), APP iso (n=6), APP het (n=4). (Panel f) Quantification of calbindin-immunoreactivity in the molecular layer of the dentate gyrus of middle-aged female parabionts; WT iso (n=9), APP iso (n=11), APP het (n=9). All data are shown as the mean+s.e.m. * P<0.05,  P<0.01, *P<0.001, Student's t test (Panel b), two-way ANOVA, Sidak's post hoc test (Panel c), one-way ANOVA, Tukey's post hoc test (Panels d-f).

To determine the impact of young circulatory factors on AD-like disease in mice, we used heterochronic parabiosis, in which we joined young animals together with APP751$^{L/S}$ mice (FIG. 11a). In the hippocampus of old male hAPP$^{L/S}$ mice, exposure to young blood did not affect insoluble Aβ levels, as measured by immunohistochemical and biochemical analysis (FIG. 11 b,c).

Synaptic and calcium binding proteins have consistently been shown to be depleted early in AD and in mouse models of the disease. Quantification of synaptophysin immunoreactivity in presynaptic terminals in the molecular layer of the dentate gyrus (DG) of the hippocampus showed a significant decrease in APP isochronic parabionts compared with wildtype isochronic parabionts, which was partially restored in APP heterochronic parabionts (FIG. 11d). The same region was analyzed for calbindin immunoreactivity. Although calbindin was not completely depleted, a significant decrease was observed in the DG of APP isochronic parabionts compared to wildtype isochronic parabionts, which was increased after exposure to a young systemic environment as demonstrated in APP heterochronic mice (FIG. 11e). Female hAPP$^{L/S}$ mice have an accelerated Aβ deposition compared to males and show decreased hippocampal calbindin and synaptophysin levels at middle-age. Similar to male mice, calbindin immunoreactivity was restored in middle-aged female APP heterochronic parabionts (FIG. 1f), indicating that the benefit of a young circulation applies to both sexes.

Figure 12:
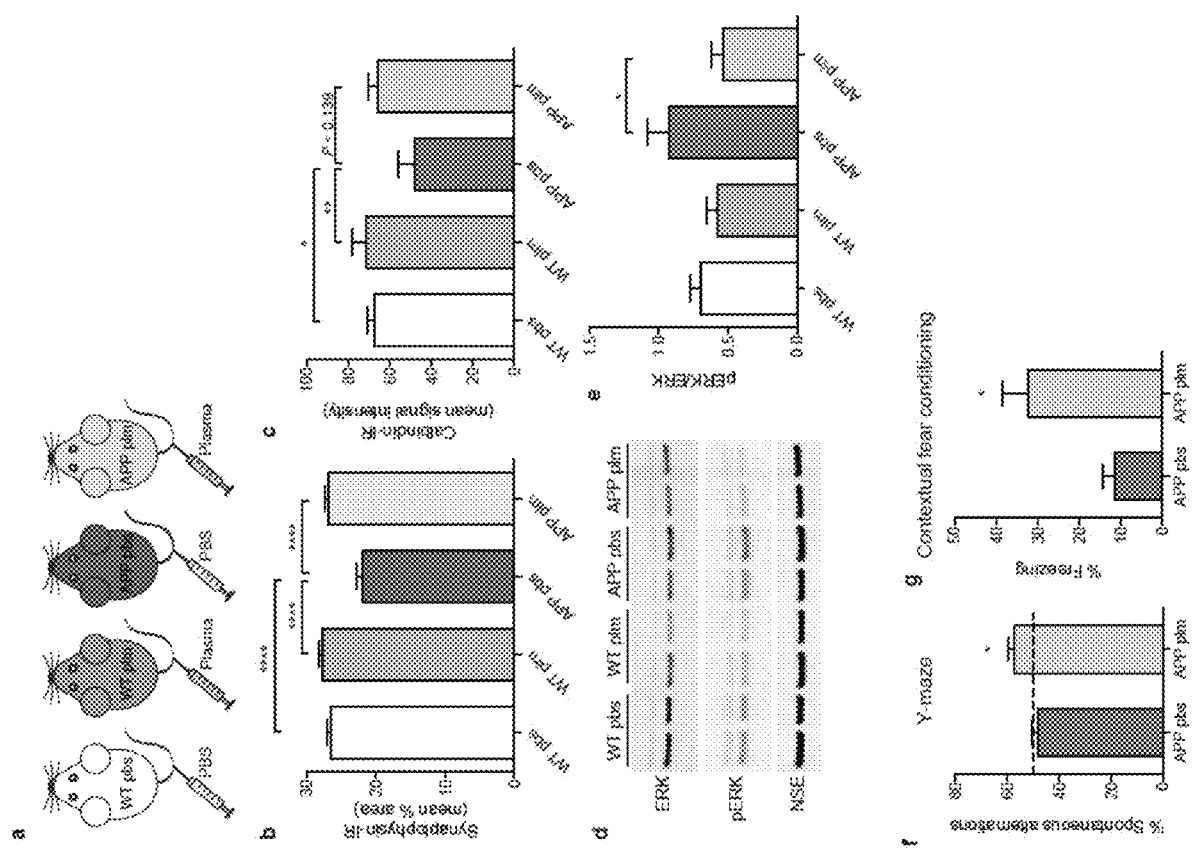
FIG. 12, Panels a-g. Administration of young blood plasma restores synaptic activity- and calcium-related proteins and improves cognition in hAPP$^{L/S}$ mice. (Panel a) Schematic depicting the 4 treatment groups, wildtype (WT) or hAPP$^{L/S}$ mice treated with either PBS or young plasma (150 µl per intravenous tail vein injection, 8 times over 30 days). (Panel b) Quantification of synaptophysin-immunoreactivity in the molecular layer of the dentate gyrus of WT pbs (n=14), WT plm (n=13), APP pbs (n=11) and APP plm (n=13) mice. (Panel c) Quantification of calbindin-immunoreactivity in the molecular layer of the dentate gyrus of WT pbs (n=15), WT plm (n=13), APP pbs (n=10) and APP plm (n=12) mice. (Panels d-e) Western blot analysis was performed on hippocampus lysates from all 4 treatment groups, n=8 per group. (Panel d) Representative Western blot for ERK (44/42 kDa), phosphorylated ERK (44/42 kDa; pERK) and neuron specific enolase (NSE) as loading control. (Panel e) Quantification of the ratio of pERK/ERK determined by densitometry of bands using ImageJ software. (Panels f-g) Cognitive testing of APP mice injected with 8 intravenous injections of PBS (n=11) or young plasma (n=13). (Panel f) Working memory assessed by spontaneous alternations in a Y-maze test for 5 minutes. Dotted line represents chance level (50%). (Panel g) Hippocampal-dependent learning and memory assessed by contextual fear conditioning indicated by percentage freezing in the same context 48 h after training. One mouse was excluded from the APP pbs group due to abnormal freezing behavior, determined by the ROUT method of identifying outliers. All data are shown as the mean+s.e.m. # P<0.1, * P<0.05,  P<0.01, **P<0.0001, one-way ANOVA, Tukey's post hoc test (Panels b-c, e), Student's t test (Panels f-g)

We have previously shown that the beneficial effects of heterochronic parabiosis on the aging brain can be achieved in part by systemic injection of plasma from young mice (Villeda et al. Young blood reverses age-related impairments in cognitive function and synaptic plasticity in mice. Nat Med 20, 659-663 (2014)), hence we examined whether young plasma might have similar benefits in hAPP$^{L/S}$ mice. We intravenously injected either young plasma or PBS in a group of hAPP$^{L/S}$ mice and a group of wildtype littermates (FIG. 12a). Each group received 8 tail vein injections over a period of 4 weeks.

Quantification of synaptophysin immunoreactivity in the DG of all 4 treatment groups demonstrated that young plasma administration in hAPP$^{L/S}$ mice restored expression levels to that of wildtype controls (FIG. 12b). Synaptophysin levels in hAPP$^{L/S}$ mice were also restored to WT levels in the neocortex, another area in which synaptic terminals were decreased in hAPP$^{L/S}$ mice, as shown by others. Young plasma administration did not affect calbindin immunoreactivity in the DG of wildtype mice. However, the significant decrease in calbindin immunoreactivity in hAPP$^{L/S}$ mice compared to wildtype mice was absent when hAPP$^{L/S}$ mice were injected with young plasma. This result indicates that plasma administration can restore pathways related to synaptic activity and calcium binding, similar to heterochronic parabiosis. We then assessed the effect of young plasma administration on one of the major signaling molecules involved in the calcium network, the MAP kinase ERK, which is known to be increased in APP mice. Western blot analysis of phosphorylated ERK (pERK) and ERK (FIG. 12d) demonstrated a decreased ratio of pERK versus ERK in hAPP$^{L/S}$ mice as a result of plasma administration (FIG. 12e), indicating a decreased ERK activation.

Since intracellular calcium regulation is crucial for synaptic plasticity and memory function and reduced synaptophysin and calbindin in AD are correlated with cognitive decline, we hypothesized that restoration of these molecules and their functions by young plasma administration could enhance the memory of hAPP$^{L/S}$ mice. To assess spatial working memory in these mice, we used a Y-maze spontaneous alternation test (FIG. 12f). Although PBS-treated hAPP$^{L/S}$ mice performed under the 50% chance level (P<0.41), indicative of an impaired working memory, plasma-treated hAPP$^{L/S}$ mice performed above chance level (P<0.0082) and made significantly more spontaneous alternations. No difference was observed between the total number of arm entries between the two treatment groups, indicating that the improvements in working memory after plasma treatment was not due to a change in activity. To assess associative learning and memory we performed a cued and contextual fear conditioning test. During the training phase, both groups exhibited similar baseline freezing and no difference was observed in amygdala-dependent cued memory. However, hAPP$^{L/S}$ mice receiving young plasma demonstrated increased freezing in the hippocampus-dependent contextual memory test (FIG. 12g), demonstrating that young plasma can restore these learning and memory deficits in a mouse model of AD.

Example 5

Figure 13:
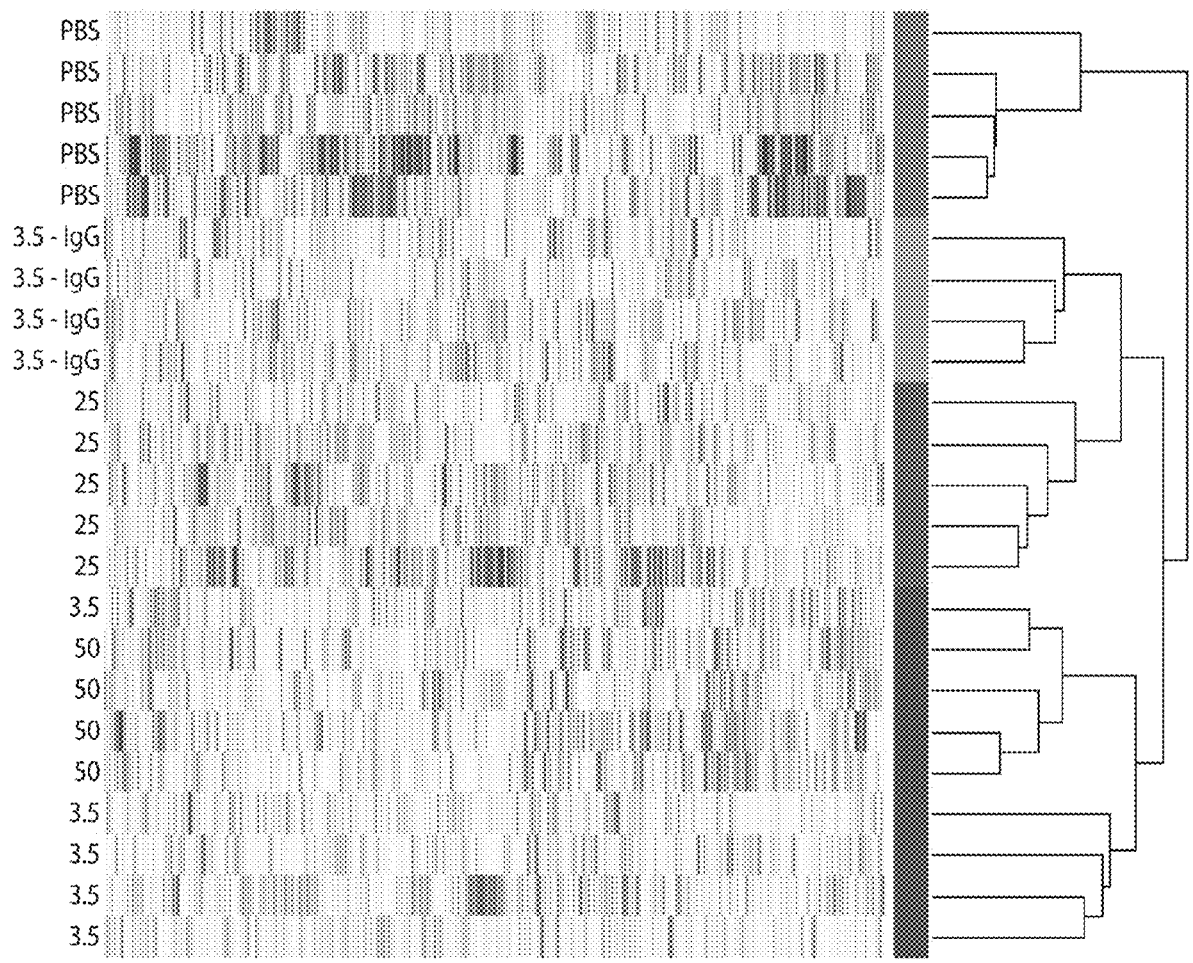
FIG. 13. 18 month-old mice (N=4-5/group) were injected intravenously 7 times over 2 weeks with fractionated plasma isolated from 2-3 month-old C57Bl/6J mice. One pool of young plasma was fractionated using molecular weight cut-off dialysis membranes, which excluded molecules below molecular weights indicated (i.e., 3.5 kDa, 25 kDa, 50 kDa, and 3.5 kDa+depletion of IgG). Hippocampi from treated mice were isolated and analyzed on whole genome Affymetrix arrays for gene expression. The heat map shows near-complete segregation by treatment in terms of increased (red) or decreased (blue) overall gene expression.

It is shown here that defined fractions of young plasma that encompass a subset of proteins and molecules of those present in intact plasma are sufficient to activate synaptic plasticity gene networks. Moreover, proteins or molecules vastly different in molecular size are able to communicate with the brain and induce changes in gene expression in the hippocampus. Pooled mouse plasma harvested from 2-3-month-old mice was segregated by size using dialysis membranes with defined molecular weight cut-offs (3.5 kDa, 25 kDa, 50 kDa) into the following fractions roughly based on molecular weight inclusion of its components: >3.5 kDa, >25 kDa, and >50 kDa. An additional fraction was generated by using the >3.5 kDa fraction and depleting IgG immunoglobulins by Protein G affinity precipitation. Each fraction was injected intravenously (125 μl per injection) 7 times over two weeks into 18-month-old mice (n=4-5 mice per fraction); phosphate buffered saline (PBS) was injected as a control. At the end of the treatment, brains were dissected and hippocampal RNA was extracted and analyzed using Affymetrix gene arrays. Several hundred genes were significantly changed in the brains of mice treated with any of the plasma fractions when compared with PBS treated mice (FIG. 13). Bioinformatics analysis with the software tool Ingenuity Pathway Analysis® (IPA) revealed several networks related to synaptic plasticity and learning and memory (e.g. long-term potentiation, branching of neuritis, behavior) which were significantly enriched in the >25 kDa fraction, but were not enriched, or less so, in other fractions. Prominent genes in these networks included known players in learning and memory including Reelin, Neurotrophic tyrosine kinase 3 receptor and ephrin receptor 4A (Table 1).

TABLE 1

| Disease or Functional Pathway | P-Value | Predicted Functional Activation | Activation Z Score | Highlighted Gene (Increased) |
|---|---|---|---|---|
| Neuritogenesis | $6.7 \times 10^{-13}$ | Increased | 2.87 | RELN (Reelin) |
| Behavior | $1.22 \times 10^{-9}$ | Increased | 3.31 | NTRK3 (Neurotrophic tyrosine kinase receptor 3) |
| Branching of neurites | $4.09 \times 10^{-9}$ | Increased | 2.00 | RELN (Reelin) |
| Long-term potentiation | $7.41 \times 10^{-8}$ | Increased | 3.13 | EPHA4 (Ephrin receptor A4) |

Table 1: Using significantly changed genes detected in brains treated with plasma above 25 kDa or vehicle, pathway analysis (IPA) was performed, revealing significantly enriched networks of genes within the category "Nervous System Development and Function" as the top network. This network was comprised of 386 molecules. Specific pathways within this network are shown with associated P values and a functional prediction based on gene changes in that network.

Together, these findings demonstrate that molecules of different molecular weight are capable of activating genes related to learning and memory and that some fractions of plasma are sufficient, while others are superior in activating these genes in the brain.

Example 6

Figure 14:
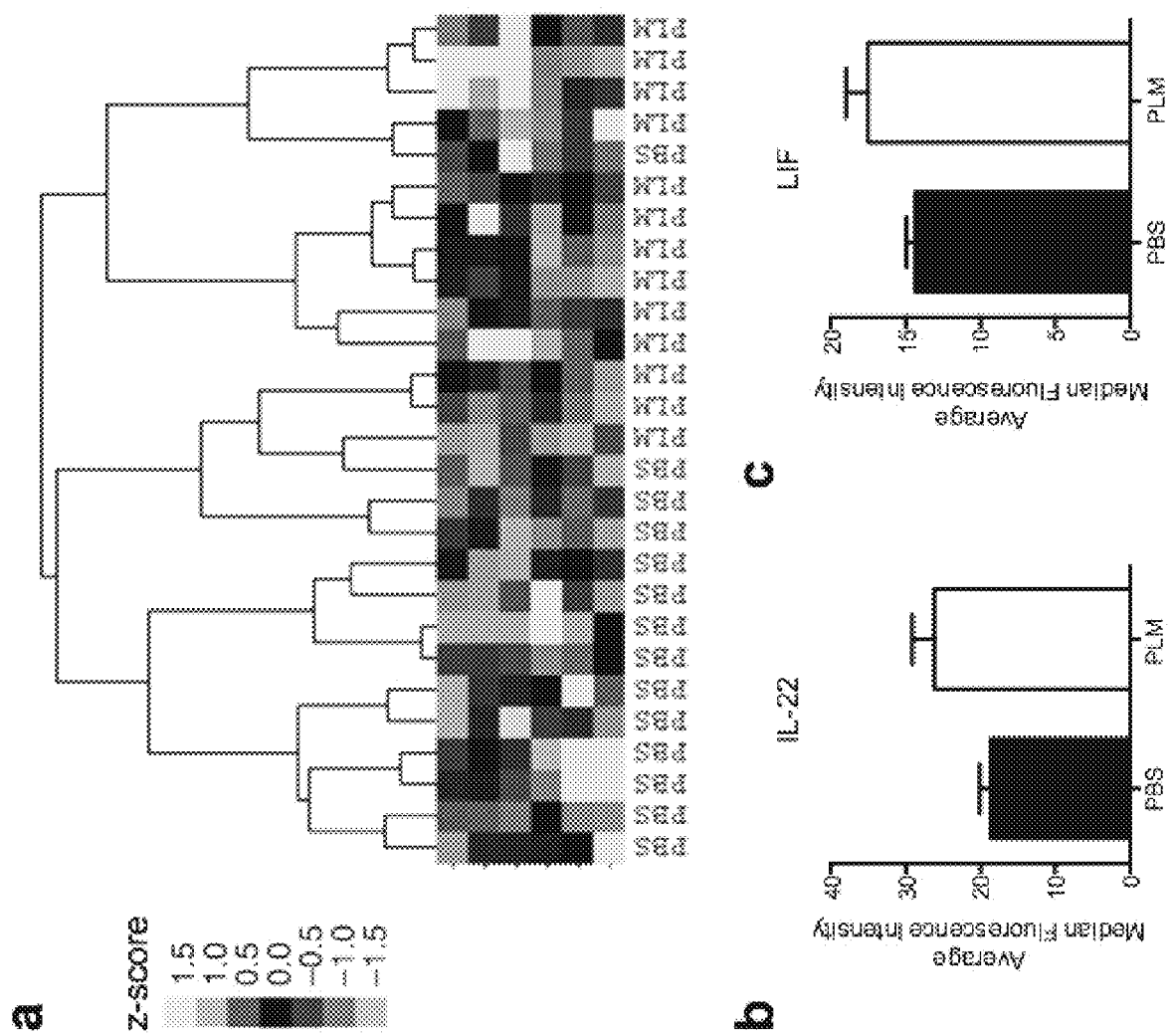
FIG. 14, Panels a-c. 12-month-old mice were injected i.v. with 150 µl PBS or 150 µl plasma (PLM) from 2-month-old mice twice a week for 4 weeks. Plasma factors were analyzed with a protein microarray (Panel a) or Luminex cytokine assay (Panels b-c). Panel a) Heat map showing six plasma factors that were significantly increased or decreased in 12 month old mice upon administration of young blood plasma. Unsupervised complete linkage clustering separates PLM samples from the PBS samples. Panels b-c) Interleukin-22 (IL-22) and Leukemia Inhibitory Factor (LIF) were increased in 12-month-old mice 4 weeks after administration of young blood plasma compared to PBS.

It is shown here that administration of young plasma to an old mouse results in systemic changes in blood, indicating organism-wide effects of the treatment. Specifically, 12-month-old, aged mice were injected with plasma from 2-month-old mice twice a week for a total of 4 weeks (n=13-14 mice per group). Each injection comprised 150 μl phosphate buffered saline (PBS) or plasma, thus accounting for approximately 5% of the body weight of the mouse per injection. Four days after the last injection blood was collected from all mice and levels of >200 growth factors and other intercellular communication proteins were measured using antibody-based microarrays or Luminex® based quantitative assays. Unsupervised complete linkage clustering of the top six proteins measured with microarrays separates blood from PBS or plasma treated mice almost perfectly (FIG. 14a) demonstrating that the blood and systemic environment of aged mice treated with young plasma is changed considerably. Many of the factors that increased have known functions in tissue regeneration. Examples of factors which are increased in blood from plasma treated aged mice include interleukin 22 (IL-22) and leukemia inhibitory factor (LIF) (FIG. 14b,c). These factors, which were measured independently and confirmed the results from the microarrays, have been shown to have beneficial effects on multiple tissues. For example, LIF improves heart function and regeneration after myocardial infarction (Zouein et al., Eur Cytokine Netw. 24:11-9, (2013)), supports skeletal muscle regeneration (Hunt et al. Histochem Cell Biol. 139:13-34, (2013)) and facilitates optic nerve regeneration and axon regeneration (Fischer D, Leibinger M., Prog Retin Eye Res. 31:688-701, 2012). Likewise, IL-22 has been demonstrated to have beneficial effects in multiple tissues including skin, pancreas, liver, and gut (Sabat et al. Nat Rev Drug Discov. 13:21-38, (2014)). Together, these findings illustrate that young plasma treatment leads to organism wide changes in intercellular communication proteins in blood and that these proteins have pleiotropic beneficial effects on multiple tissues.

Example 7

Figure 15:
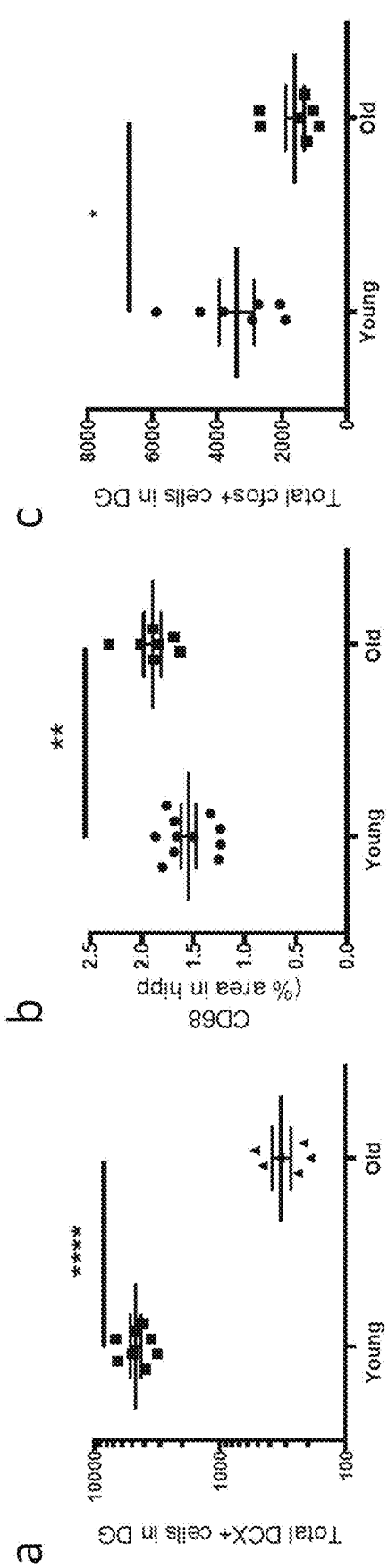
FIG. 15, Panels a-c. NSG mice display age-dependent changes in (Panel a) doublecortin (DCX)+cells in the dentate gyrus, (Panel b) CD68 staining as a percentage of total hippocampal area, and (Panel c) total number of cfos-positive cells in the dentate gyrus. (Mean+/−SEM; Student's t test; *P<0.05, P<0.01, **P<0.0001.)

It is shown here that mice treated with young human plasma show increases in neural activity in the brain, that human plasma from umbilical cord is most potent in activating neurons, and that longer term treatment with young human plasma improves cognition in aged mice. We have previously demonstrated that young mouse plasma is sufficient to enhance cognitive function in aged mice, in part, by enhancing synaptic plasticity in the hippocampus, a brain region involved in learning and memory (Villeda et al. Young blood reverses age-related impairments in cognitive function and synaptic plasticity in mice. Nat Med 20, 659-663 (2014)). In order to demonstrate translational utility of young plasma as a restorative agent to rejuvenate the aged brain, we sought to develop a mouse model in which human blood plasma could be injected and tolerated without the harmful effects of immune rejection. We hypothesized that NOD/SCID (NSG) mice (Shultz et al. Human lymphoid and myeloid cell development in NOD/LtSz-scid IL2R gamma null mice engrafted with mobilized human hemopoietic stem cells. J Immunol 174, 6477-6489 (2005)), which lack a functional immune system, would be a tractable model for this purpose given that antibody production and complement activation is severely impaired. To demonstrate its utility as a model to study soluble plasma factors in the context of aging, we first assessed the ability of the NSG model to recapitulate keys aspects of brain aging. As shown in FIG. 15, we find that NSG mice display age-related deficits in the number of newborn neurons in the dentate gyrus of the hippocampus, as well as increased microgliosis, as reflected by CD68 staining in the hippocampus. We also found an age-dependent decline in the number of cfos-positive cells in the dentate gyrus, which is a neuronal surrogate for the immediate early gene family that plays a role in synaptic plasticity.

Figure 16:
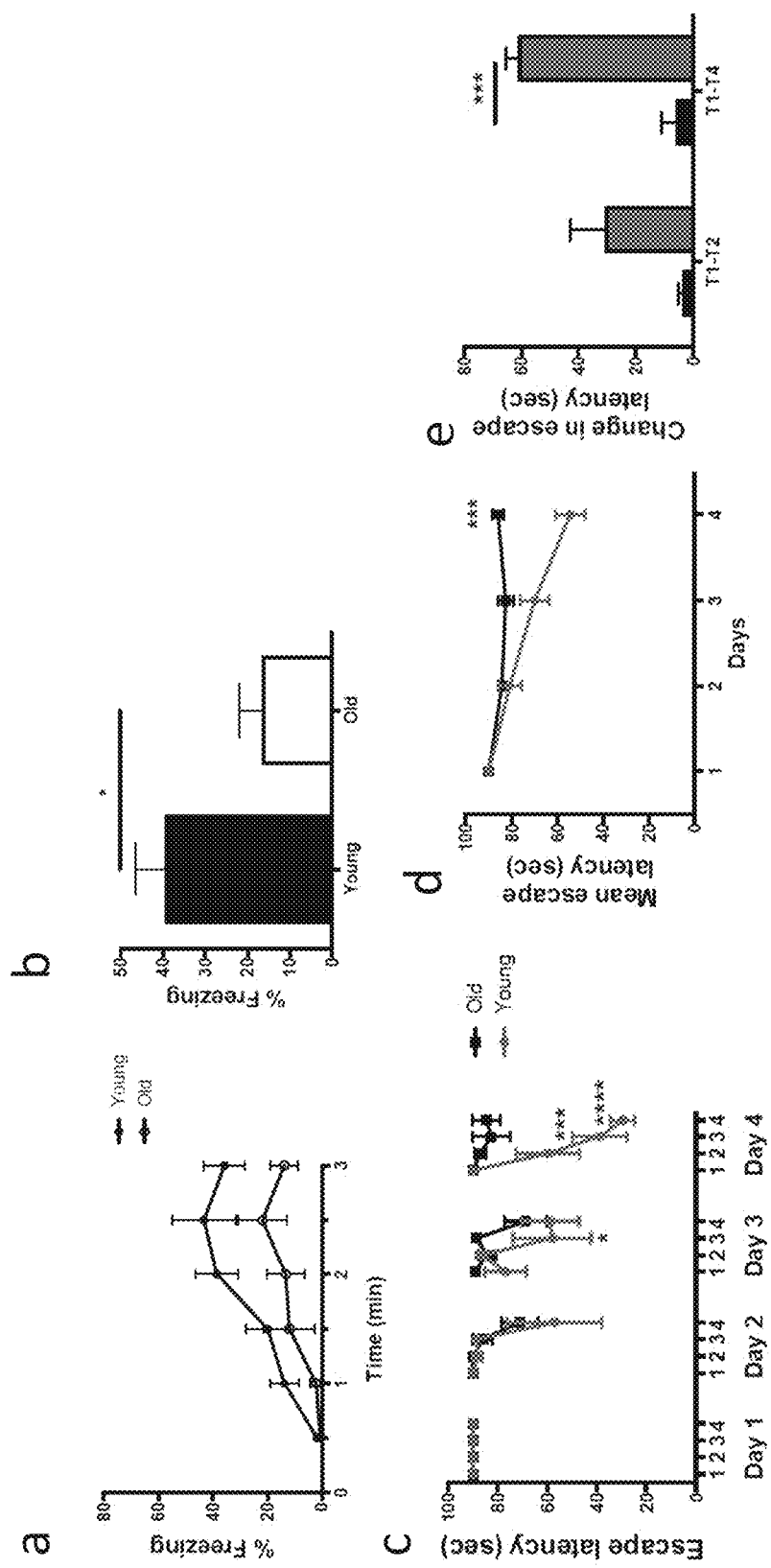
FIG. 16, Panels a-e. (Panel a) Levels of freezing in aged NSG mice are significantly lower than in young NSG mice in the last 90 seconds when exposed to a chamber to which they have been previously trained to associate with fear. (Panel b) Quantification of freezing levels in the final intervals of contextual fear conditioning in young and old NSG mice from (Panel a). (Panel c) Aged NSG mice display deficits over days and within trials of the same day in finding the escape hole during the Barnes maze. (Panel d) Aged NSG mice also display deficits compared to young NSG mice in terms of daily overall performance. (Panel e) The rate of learning, the difference in individual probe trials from initial training trial, is significantly higher in young NSG mice. (Mean+/−SEM; Student's t test for 2-group comparisons and, where appropriate, 2-way repeated-measures ANOVA, followed by Bonferroni's post-hoc test for correction of multiple comparisons; *P<0.05, P<0.01, *P<0.001, ****P<0.0001.)

As shown in FIG. 16, we observed striking cognitive deficits in aged NSG mice, whether in the contextual fear conditioning task or when we asked mice to remember the location of an escape hole in the Barnes maze task. Importantly, all age-dependent deficits were observed using NSG mice that were approximately middle-aged, an age in normal mice at which deficits are usually only subtle. Taken together, the model demonstrates a facile tool with which the relevance of plasma treatment can be tested using human material in a rapid fashion.

Figure 17:
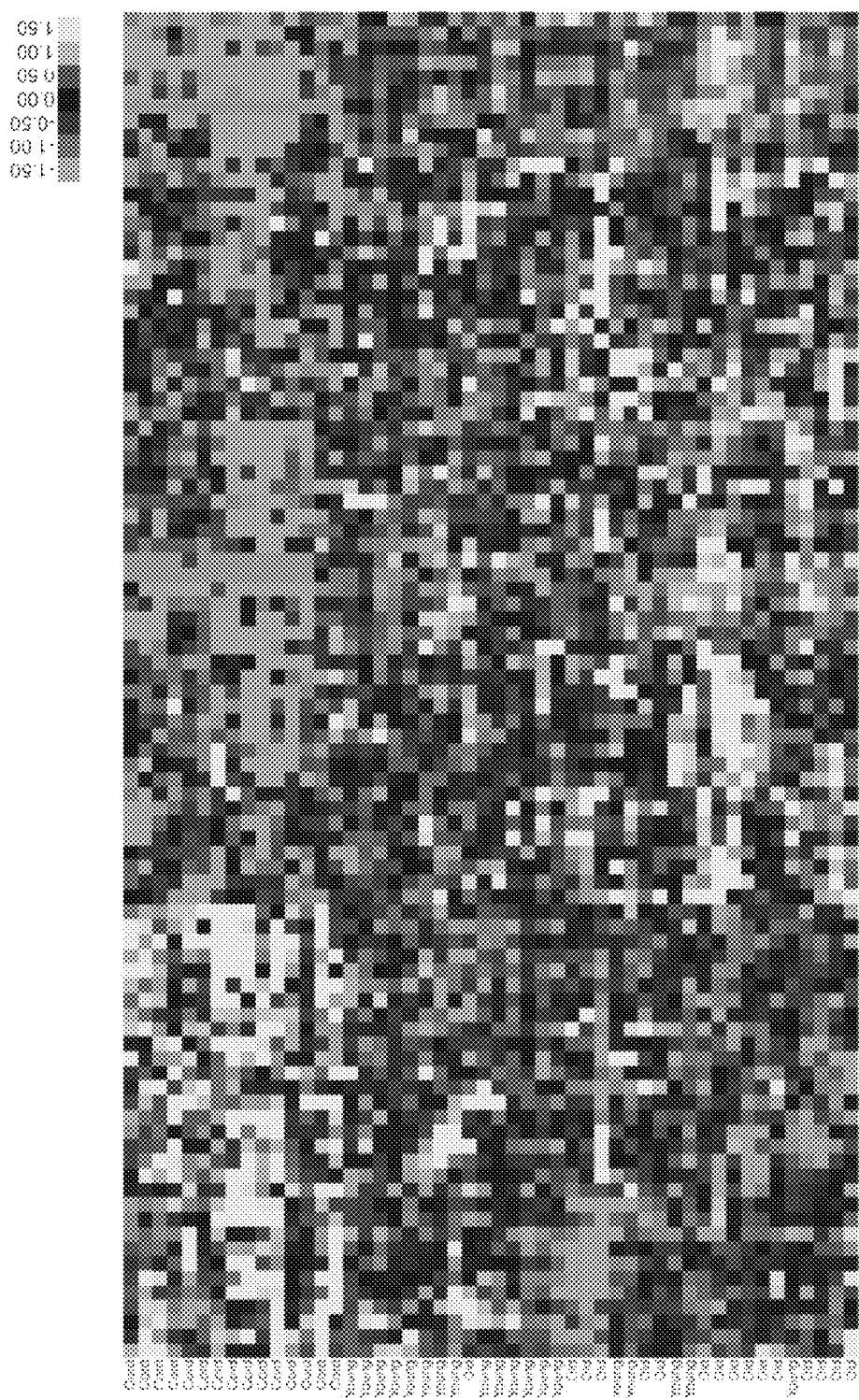
FIG. 17. Heat map demonstrating a high degree of clustering in terms of protein expression by age group among plasma samples taken from human umbilical cord donors (N=15), young donors (N=19), or elderly donors (N=16). Blocks represent individual secreted signaling proteins that are enriched (yellow) or decreased (blue) relative to the levels of expression for that protein among all age groups. Proteins shown are those that were significant after time correlation SAM (q<5%).
Figure 18:
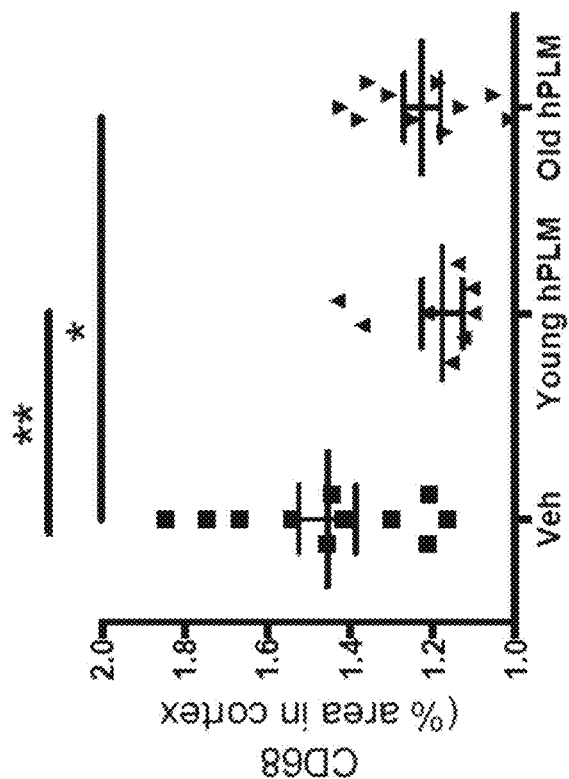
FIG. 18. Injections of human plasma (hPLM) from young or old donors in aged NSG mice revealed changes in the percentage area occupied by CD68 staining in the hippocampus (left) or cortex (right) compared to vehicle-treated NSG mice. (Mean+/−SEM; Student's t test; *P<0.05, **P<0.01.)
Figure 18:
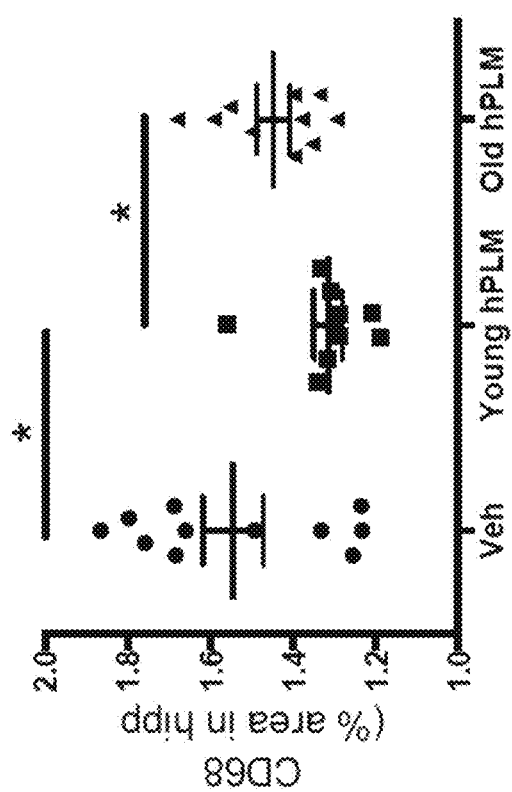
Figure 19:
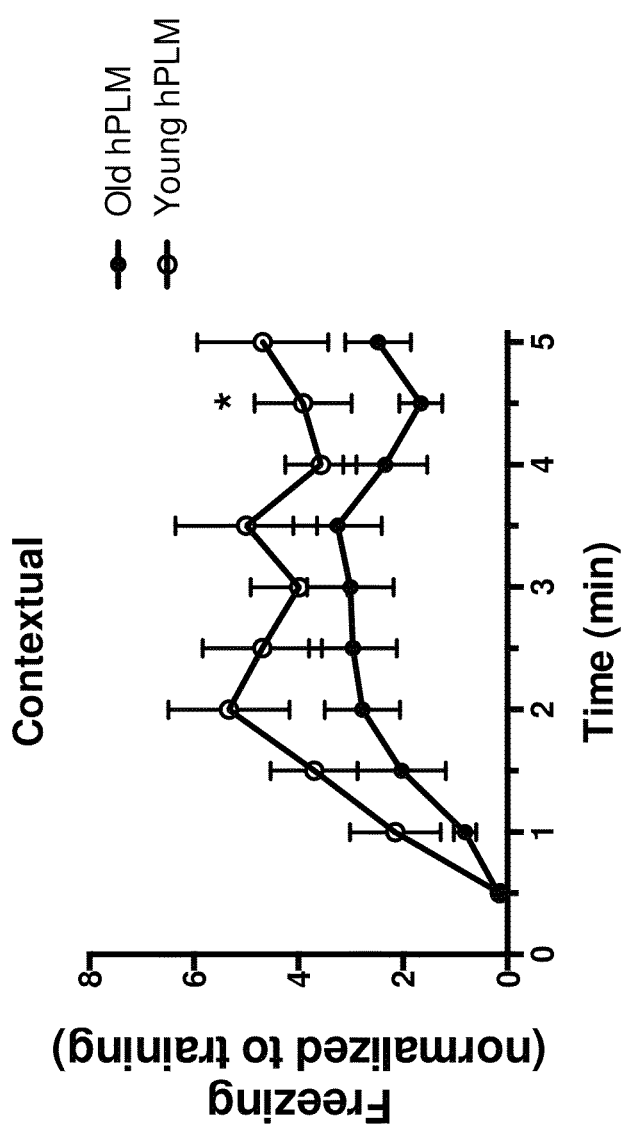
FIG. 19. After normalizing the levels of freezing in the contextual fear conditioning task (day 2) to the freezing observed during training (day 1), young human plasma (hPLM) increases contextual memory at 4.5 minutes compared to aged NSG mice treated with old hPLM. (Mean+/−SEM; Student's t test at the indicated interval; *P<0.05.)

We next sought to assess whether soluble factors present human plasma differ substantially across developmental stages of aging. We isolated blood plasma from umbilical cord plasma donors, as well as young and elderly individuals and analyzed the relative levels of approximately 600 secreted signaling proteins using our in-house protein microarray platform. As shown in FIG. 17, there is clear segregation by the age of human plasma, especially when comparing cord plasma samples to those of young or elderly donors. There is a striking enrichment of many factors present in cord plasma compared to young or elderly samples, revealing a subset of proteins that display an age-dependent decline in expression. We next sought to assess whether injection of human plasma in aged NSG mice would alter neuroinflammation, a reproducible brain aging phenotype. As shown in FIG. 18, we report a subtle, but significant decrease in microgliosis in the hippocampus and cortex of aged NSG mice treated with young human plasma. Old human plasma was not sufficient to alter the level of microgliosis. Mice treated with young human plasma exhibited higher levels of contextual fear conditioning compared to mice treated with old human plasma, revealing that young plasma possesses factors sufficient to enhance cognition (FIG. 19).

Figure 20:
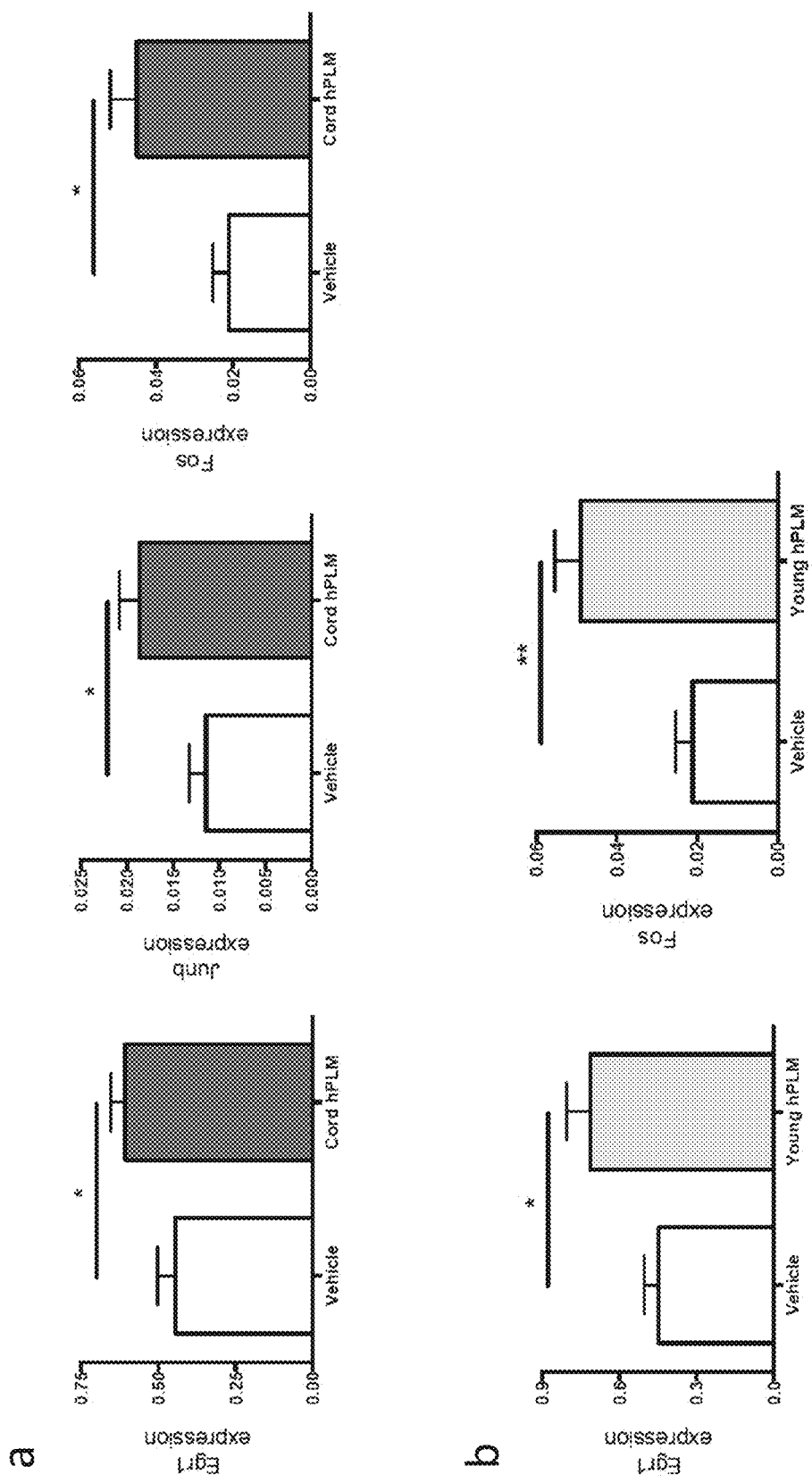
FIG. 20, Panels a-b. Levels of gene expression by qPCR in aged NSG mice treated with human cord or young plasma compared to vehicle-treated mice. Changes in immediate early gene expression (Egr1, Junb, fos) were assessed in brains isolated from aged NSG mice treated intravenously with human plasma or vehicle over 3 weeks. (Mean+/−SEM; Student's t test; *P<0.05.)
Figure 21:
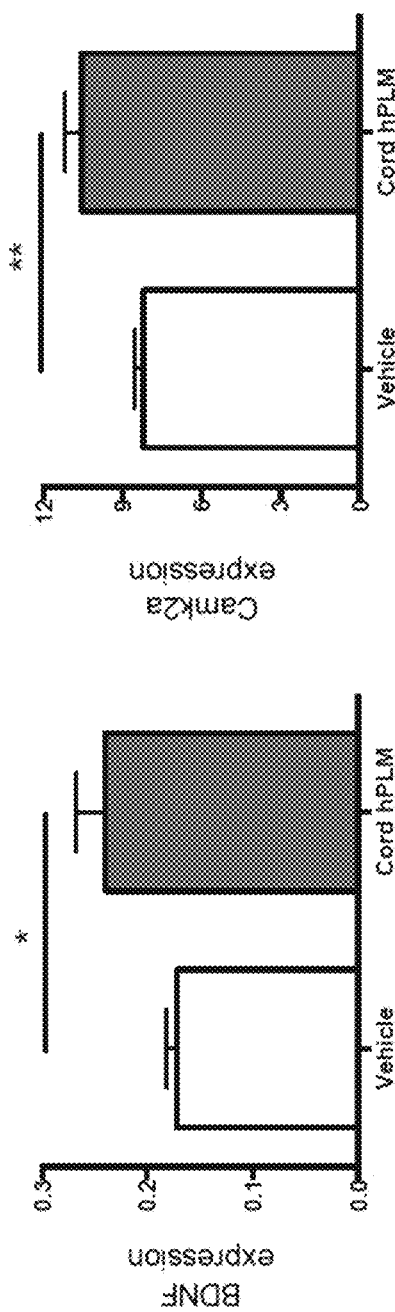
FIG. 21. Additional plasticity-relevant genes BDNF and Camk2a were measured by qPCR in aged NSG mice treated with human cord plasma or vehicle. (Mean+/−SEM; Student's t test; *P<0.05.)
Figure 22:
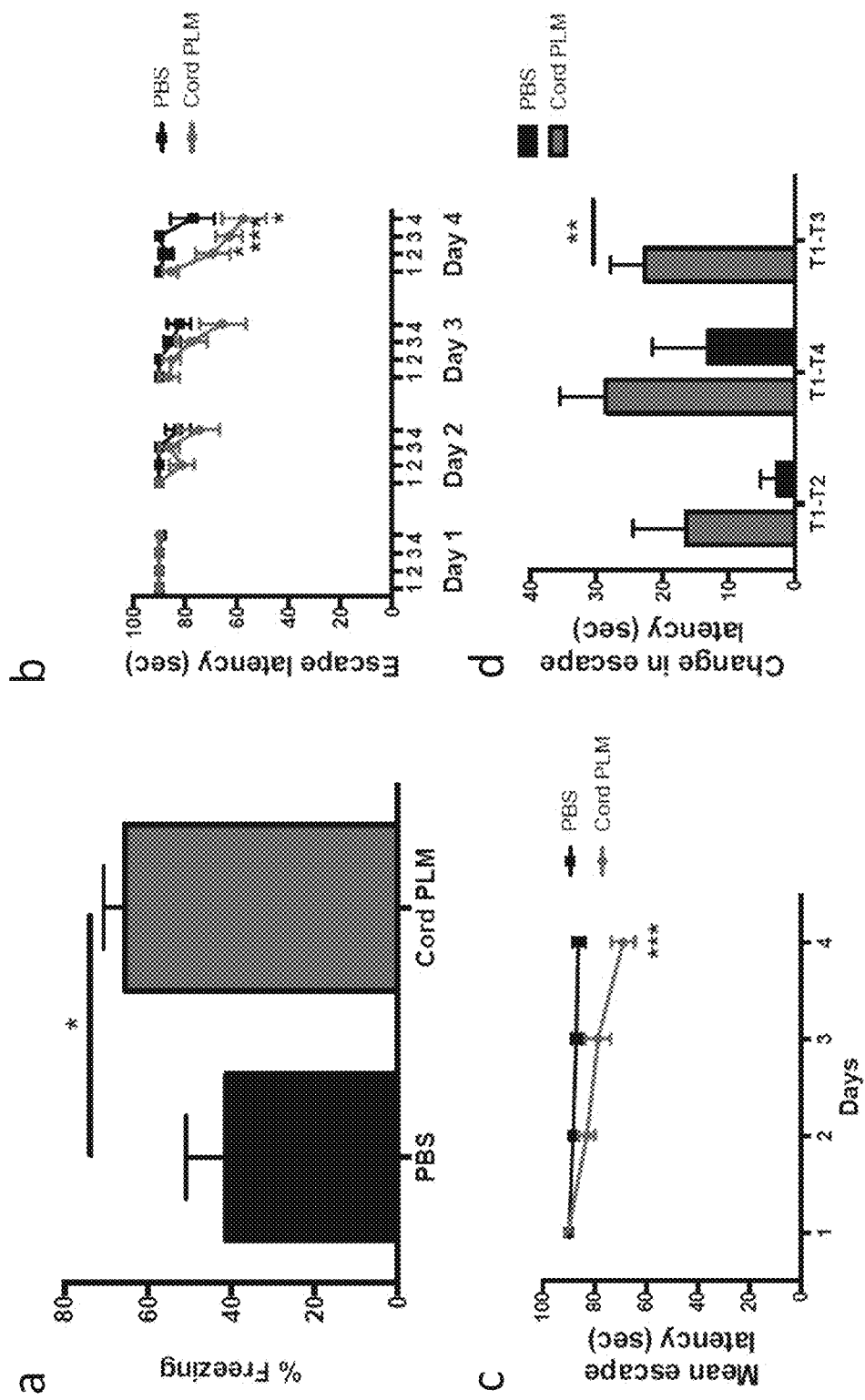
FIG. 22, Panels a-d. (Panel a) Quantification of levels of freezing in aged NSG mice treated with cord plasma or vehicle in the last 90 seconds when exposed to a chamber to which they have been previously trained to associate with fear. (Panel b) Aged NSG mice treated with cord plasma display enhanced learning and memory by day 4 and within trials of the same day in finding the escape hole during the Barnes maze. (Panel c) Cord plasma-treated mice also display improved learning and memory compared to vehicle-treated NSG mice in terms of daily overall performance. (Panel d) The rate of learning, the difference in probe trials from the initial training trial, is significantly higher in cord plasma treated mice compared to vehicle-treated mice for the third probe trial. (Mean+/−SEM; Student's t test for 2-group comparisons and, where appropriate, 2-way repeated-measures ANOVA, followed by Bonferroni's post-hoc test for correction of multiple comparisons; *$P<0.05$, $P<0.01$, *$P<0.001$).

Immediate early gene expression, especially expression of cfos, Junb, and Egr1, is a well-characterized correlate underlying synaptic plasticity (Bailey et al Toward a molecular definition of long-term memory storage. Proc Natl Acad Sci USA 93, 13445-13452 (1996)). We examined levels of immediate early gene expression by qPCR in human plasma-treated NSG mice. We find that both cord and young human plasma are sufficient to enhance expression of the immediate early genes Egr1, Junb, and fos, the gene that encodes cfos protein (FIG. 20) as well as Bdnf and CamK2a (FIG. 21). Overall we find more significant enhancements of plasticity-related genes in cord plasma-treated NSG mice than in mice treated with young or old human plasma. Taken together, our data suggest that factors present in cord plasma may be capable of rejuvenating brain aging phenotypes related to learning and memory. To test whether human cord plasma is capable of reversing age-dependent behavioral deficits, we treated aged NSG mice with vehicle or cord plasma and performed contextual fear conditioning and Barnes maze testing. As shown in FIG. 22, cord plasma significantly enhanced the level of freezing in the contextual fear conditioning task compared to vehicle-treated mice. Exposing the same mice to Barnes maze revealed that cord plasma-treated mice eventually learn to remember where the escape hole is located to a significantly greater extent than mice treated with vehicle. This effect was especially prominent on the final day of testing in the last 3 trials, during which untreated aged NSG mice usually have difficulty performing the task. The rate of learning, as indicated by the difference between subsequent probe trials and the initial training trial on Day 4, was also significantly greater in aged NSG mice treated with cord plasma than in vehicle-treated mice.

Figure 23:
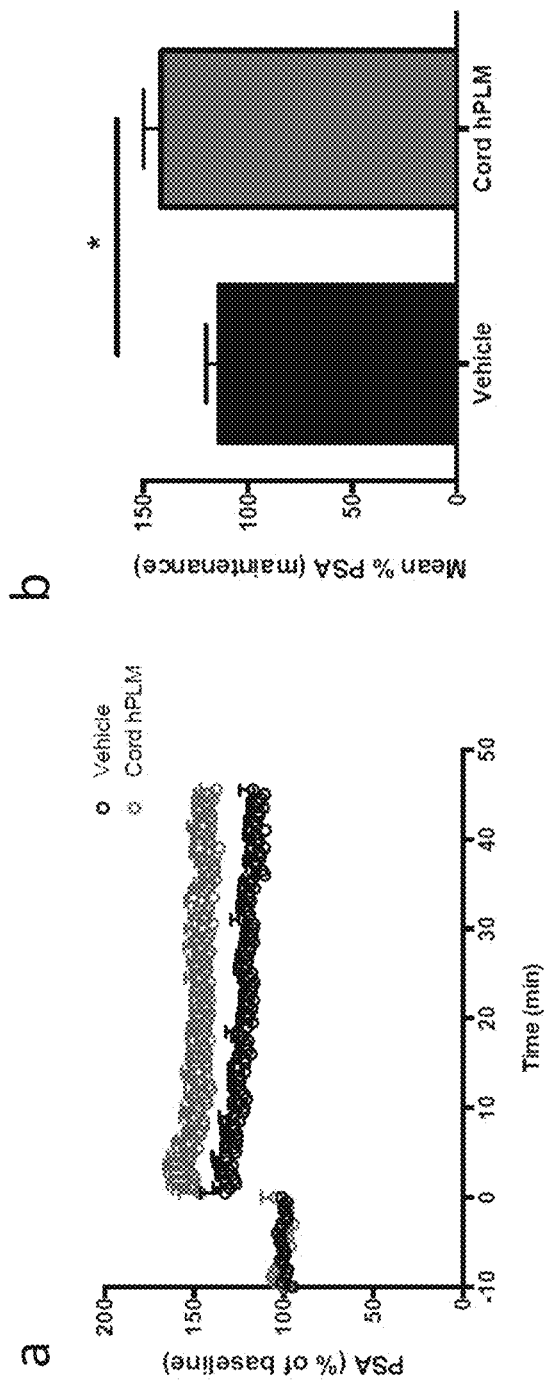
FIG. 23, Panels a-b. (Panel a) Slices taken from brains of cord plasma-treated mice display enhanced long-term potentiation (LTP) as assessed by measuring the population spike amplitudes in dentate gyrus after stimulation in the perforant path of the hippocampus. (Panel b) Quantification of the maintenance phase of the PSA shown in (Panel a). (Mean+/−SEM; Student's t test; *$P<0.05$.)

We examined whether enhancements in long-term potentiation, a cellular and electrophysiological correlate for increased synaptic strength and plasticity (Bliss and Collingridge. A synaptic model of memory: long-term potentiation in the hippocampus. Nature 361, 31-39, (1993)), may underlie the increased learning and memory observed in aged NSG mice treated with cord plasma. As shown in FIG. 23, we observed significantly higher levels of LTP in hippocampal slices from cord plasma-treated mice than in slices from vehicle-treated mice. Taken together, our data indicate a mechanism by which factors present in cord plasma enhance learning and memory in the aged brain, likely by increasing expression of genes involved in learning and memory that ultimately leading to cellular changes that underlie increased LTP.

Figure 24:
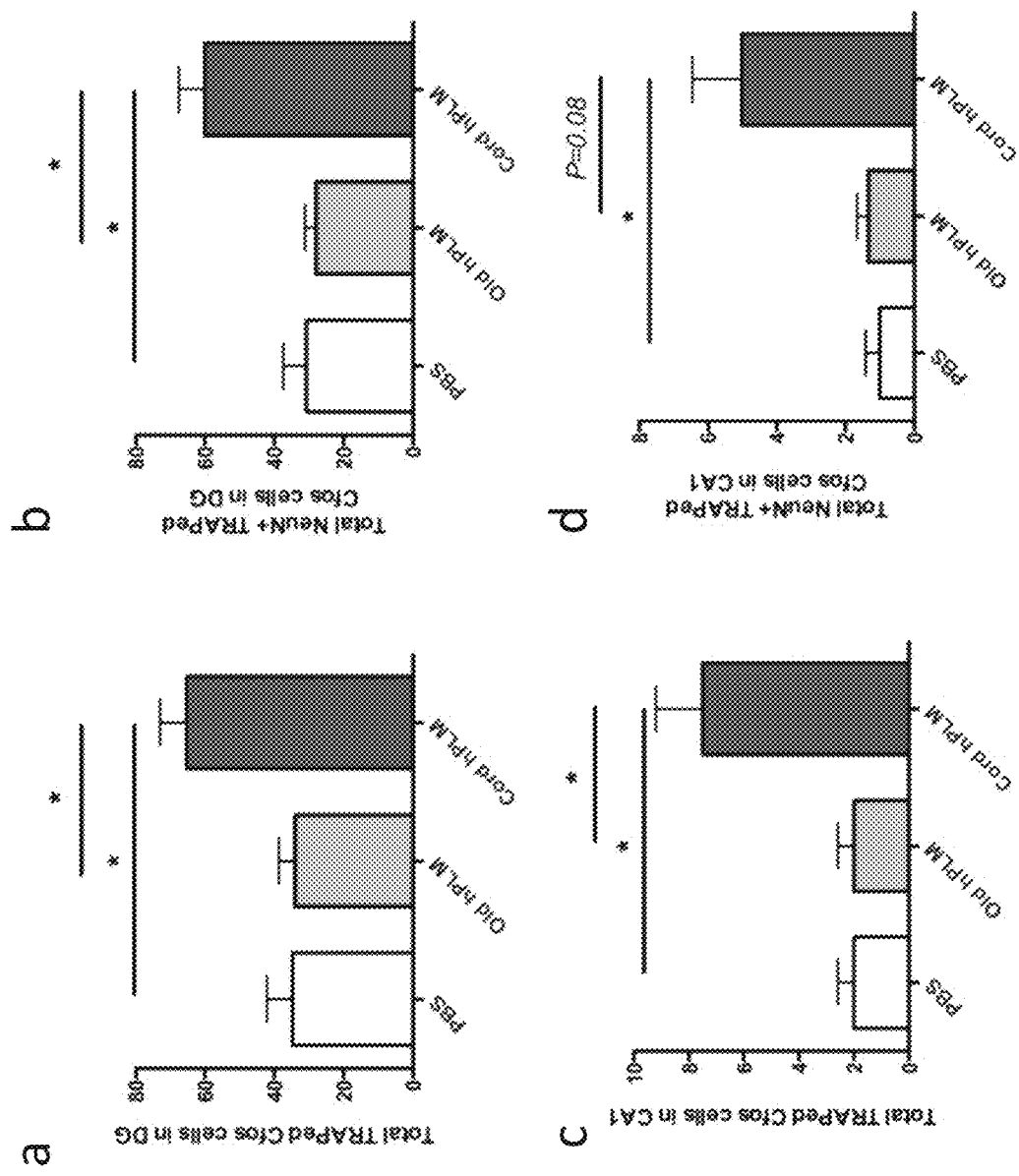
FIG. 24, Panels a-d. (Panel a) Quantification of the number of TRAPed cells driving effector protein expression from cfos in the dentate gyrus (DG) for TRAP-FOS mice treated with vehicle, old human plasma (hPLM), or cord hPLM. (Panel b) Quantification of the number of TRAPed NeuN-positive (neuron) cells driving effector protein expression from cfos in the dentate gyrus (DG) for TRAP-FOS mice treated with vehicle, old hPLM, or cord hPLM. (Panel c) Quantification of the number of TRAPed cells driving effector protein expression from cfos in the CA1 region for TRAP-FOS mice treated with vehicle, old hPLM, or cord hPLM. (Panel d) Quantification of the number of TRAPed NeuN-positive cells driving effector protein expression from cfos in the CA1 region for TRAP-FOS mice treated with vehicle, old hPLM, or cord hPLM. (Mean+/−SEM; 1-way ANOVA, followed by Tukey's post-hoc test for correction of multiple comparisons; *$P<0.05$.)

Our data reveal that human plasma, particularly cord plasma, can rejuvenate aspects of brain aging in NSG mice, including changes in cfos expression in the hippocampus. To assess whether these changes are also observed in the setting of a functional immune system, we utilized the TRAP-FOS mouse model developed by Liqun Luo's laboratory at Stanford University (Guenthner et al. Permanent genetic access to transiently active neurons via TRAP: targeted recombination in active populations. Neuron 78, 773-784 (2013)). Acute manipulations often result in transient changes in immediate early gene expression, including cfos expression, which can be difficult to detect at the time of analysis. In the Targeted Recombination in Active Recombination (TRAP) model, tamoxifen-dependent CreER-T2 can be expressed in a manipulation-dependent manner from the FOS promoter, which results in fluorescent effector protein expression that is permanent once expressed. In this way, we are able to provide an acute treatment with human cord plasma in order to examine rapid changes in cfos expression, while still preventing a significant immune response. After only a single injection, we find that treatment with cord plasma in TRAP-FOS mice resulted in significantly more TRAPed neurons driving fluorescent protein from the cfos promoter in both the dentate gyrus and CA1 of hippocampus compared to TRAP-FOS mice treated with vehicle (FIG. 24). Old human plasma was insufficient to increase such expression. Our results demonstrate clear functional importance for factors present in human plasma in reversing brain aging processes in vivo. Given our results in mice using human plasma factors, fractionated human plasma will target similar biological processes in the human brain, providing clear benefits for patients experiencing age-related cognitive decline.

Example 8

A human patient with mild to moderate Alzheimer's disease is infused intravenously with 200 mls of human plasma from a young blood donor (younger than 30 years of age). This procedure is repeated, e.g. once per week, for 4 weeks, during which time the caregiver records general functions and activities of daily living of the patient. After the treatment is completed the brain of the patient is scanned for resting state brain activity using functional MRI and cognitive function of the patient is assessed with a battery of neuropsychological tests. At all times, the patient, the caregiver, and the physicians administrating the treatments or test are unaware whether the patient has received young blood plasma or saline solution as a control. The measurements obtained after the treatment are then compared to similar measurements obtained in the patient before the treatment was initiated. It is observed that the patients receiving young plasma demonstrate improved general functions and activities of daily living.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

That which is claimed is:

1. A method of treating a subject for a hippocampal mediated aging-associated cognitive impairment comprising:

administering to the subject an effective amount of a young blood plasma product to treat the subject for the hippocampal mediated aging-associated cognitive impairment, wherein the young blood plasma product has been prepared by a process comprising removing proteins having an average molecular weight below 25 kDa from plasma from a donor or donors 40 years old or younger, and younger than the subject.

2. The method according to claim 1, wherein the young blood plasma product is obtained from an umbilical cord.

3. The method according to claim 1, wherein the hippocampal mediated aging-associated cognitive impairment is selected from the group consisting of attention and concentration; learning complex tasks and concepts; memory; information processing; visuospatial function; producing and understanding language; verbal fluency; solving problems; making decisions; and executive functions.

4. The method according to claim 1, wherein the hippocampal mediated aging-associated cognitive impairment is due to a neurodegenerative condition selected from the group consisting of Alzheimer's disease, Parkinson's disease, Huntington disease, frontotemporal dementia, amyotrophic lateral sclerosis, multiple sclerosis, myotonic dystrophy, progressive supranuclear palsy, spinal muscular atrophy, multi-system atrophy, ataxias, and vascular dementia.

5. The method according to claim 1, wherein the method further comprises:

measuring cognitive ability in the subject.

6. The method according to claim 1, wherein the subject is 50 years old or older.

7. The method according to claim 1, wherein the young blood plasma product lacks proteins having an average molecular weight that is 50 kDa or less.

8. The method according to claim 1, wherein the young blood plasma product lacks IgG.

* * * * *